US009265808B2

(12) United States Patent
McCord et al.

(10) Patent No.: US 9,265,808 B2
(45) Date of Patent: *Feb. 23, 2016

(54) COMPOSITIONS FOR ALLEVIATING INFLAMMATION AND OXIDATIVE STRESS IN A MAMMAL

(71) Applicant: Lifeline Nutraceuticals Corporation, Sandy, UT (US)

(72) Inventors: Joe Milton McCord, West Palm Beach, FL (US); Paul R. MyHill, Castle Rock, CO (US)

(73) Assignee: Lifeline Nutraceuticals Corporation, Sandy, UT (US)

( * ) Notice: Subject to any disclaimer, the term of this patent is extended or adjusted under 35 U.S.C. 154(b) by 138 days.

This patent is subject to a terminal disclaimer.

(21) Appl. No.: 13/829,205

(22) Filed: Mar. 14, 2013

(65) Prior Publication Data

US 2014/0271944 A1   Sep. 18, 2014
US 2015/0283193 A9   Oct. 8, 2015

Related U.S. Application Data

(63) Continuation-in-part of application No. 13/492,638, filed on Jun. 8, 2012, now Pat. No. 8,435,574, which is a continuation of application No. 13/039,073, filed on Mar. 2, 2011, now Pat. No. 8,221,805, which is a continuation of application No. 12/546,063, filed on Aug. 24, 2009, now Pat. No. 7,923,045, which is a continuation of application No. 11/216,514, filed on Aug. 31, 2005, now Pat. No. 7,579,026, which is a continuation of application No. 11/088,323, filed on Mar. 23, 2005, now Pat. No. 7,241,461.

(60) Provisional application No. 60/555,802, filed on Mar. 23, 2004, provisional application No. 60/590,528, filed on Jul. 23, 2004, provisional application No. 60/604,638, filed on Aug. 26, 2004, provisional application No. 60/607,648, filed on Sep. 7, 2004, provisional application No. 60/610,749, filed on Sep. 17, 2004, provisional application No. 60/643,754, filed on Jan. 13, 2005, provisional application No. 60/646,707, filed on Jan. 25, 2005.

(51) Int. Cl.

| | |
|---|---|
| *A01N 65/00* | (2009.01) |
| *A61K 36/28* | (2006.01) |
| *A61K 31/12* | (2006.01) |
| *A61K 31/585* | (2006.01) |
| *A61K 31/7048* | (2006.01) |
| *A61K 36/16* | (2006.01) |
| *A61K 36/23* | (2006.01) |
| *A61K 36/81* | (2006.01) |
| *A61K 36/82* | (2006.01) |
| *A61K 36/886* | (2006.01) |
| *A61K 36/9066* | (2006.01) |
| *A61K 36/00* | (2006.01) |
| *G01N 33/50* | (2006.01) |
| *A61K 36/80* | (2006.01) |
| *A61K 31/198* | (2006.01) |
| *A61K 31/353* | (2006.01) |
| *A61K 31/357* | (2006.01) |

(52) U.S. Cl.
CPC .......... *A61K 36/28* (2013.01); *A61K 31/12* (2013.01); *A61K 31/198* (2013.01); *A61K 31/353* (2013.01); *A61K 31/357* (2013.01); *A61K 31/585* (2013.01); *A61K 31/7048* (2013.01); *A61K 36/00* (2013.01); *A61K 36/16* (2013.01); *A61K 36/23* (2013.01); *A61K 36/80* (2013.01); *A61K 36/81* (2013.01); *A61K 36/82* (2013.01); *A61K 36/886* (2013.01); *A61K 36/9066* (2013.01); *G01N 33/502* (2013.01); *G01N 2800/7009* (2013.01)

(58) Field of Classification Search
CPC .................................................... A61K 36/00
USPC .......................................................... 424/725
See application file for complete search history.

(56) References Cited

U.S. PATENT DOCUMENTS

| | | |
|---|---|---|
| 4,522,811 A | 6/1985 | Eppstein et al. |
| 5,494,668 A | 2/1996 | Patwardhan |

(Continued)

FOREIGN PATENT DOCUMENTS

| | | |
|---|---|---|
| EP | 0659402 | 6/1995 |
| JP | 06-02437 | 2/1994 |

(Continued)

OTHER PUBLICATIONS

Anderson, ME. "Determination of glutathione and glutathione disulfide in biological samples." 1985 Methods Enzymol; 113:548-55.

(Continued)

*Primary Examiner* — Michael Meller
(74) *Attorney, Agent, or Firm* — Greenberg Traurig, LLP

(57) ABSTRACT

An antioxidant-promoting composition that increases antioxidant defense potential in a subject is disclosed. The composition contains *Bacopa monnieri* extract comprising a *Bacopa monnieri* active ingredient; a *Silybum marianum* (milk thistle) extract comprising a *Silybum marianum* active ingredient; a *Withania somnifera* (ashwagandha) extract comprising a *Withania somnifera* active ingredient; a *Camellia sinensis* (green tea) extract comprising a *Camellia sinensis* active ingredient; a *Curcuma longa* (turmeric) extract comprising at least one *Curcuma longa* active ingredient, and optionally a *Centella asiatica* (Gotu kola) extract; a *Ginko biloba* extract; an *Aloe vera* extract; and N-acetyl cysteine. The process for quantifying Nrf2 transcription factor activating potential of the botanical extracts comprising the botanical active ingredients is described.

1 Claim, 40 Drawing Sheets

(56) References Cited

U.S. PATENT DOCUMENTS

| | | | |
|---|---|---|---|
| 5,854,287 | A | 12/1998 | Weglicki |
| 5,939,395 | A | 8/1999 | Yu et al. |
| 6,093,404 | A | 7/2000 | Kattan |
| 6,162,438 | A | 12/2000 | Tomer et al. |
| 6,372,265 | B2 | 4/2002 | Saito |
| 6,495,170 | B1 | 12/2002 | Smit et al. |
| 6,646,013 | B1 | 11/2003 | Barker et al. |
| 6,841,177 | B1 | 1/2005 | Quintanilla Almagro et al. |
| 7,241,461 | B2 | 7/2007 | Myhill et al. |
| 7,384,655 | B2 | 6/2008 | Myhill et al. |
| 7,579,026 | B2 | 8/2009 | Myhill et al. |
| 7,923,045 | B2 | 4/2011 | Myhill et al. |
| 8,221,805 | B2 | 7/2012 | Myhill et al. |
| 8,435,574 | B2 | 5/2013 | Myhill et al. |
| 2002/0086067 | A1 | 7/2002 | Choi |
| 2002/0160082 | A1 | 10/2002 | Pola |
| 2003/0072823 | A1 | 4/2003 | Fleischner |
| 2004/0131656 | A1 | 7/2004 | Roufs et al. |

FOREIGN PATENT DOCUMENTS

| | | |
|---|---|---|
| JP | 2002-233332 | 8/2002 |
| JP | 2002-275079 | 9/2002 |
| WO | WO 01/21185 | 3/2001 |
| WO | WO 2005/094862 | 10/2005 |

OTHER PUBLICATIONS

Gutteridge, JM and Quinlan, GJ. "Malondialdehyde formation from lipid peroxides in the thiobarbituric acid test: the role of lipid radicals, iron salts, and metal chelators." 1983 J Appl Biochem 5(4-5)293-9.

Johnson VJ et al. "Physiological responses of a natural antioxidant flavonoid mixture, silymarin, in BALB/c mice: III. Silymarin inhibits T-lymphocyte function at low doses but stimulates inflammatory process at high doses." 2003 Planta Med. 69(1):44-9.

Meerhof, LJ and Roos, D. "An easy, specific and sensitive assay for the determination of the catalase activity of human blood cells." 1980 J Reticuloendothel Soc; 28(5):419-25.

Powell, et al. "Oxygen free radicals: Effect on red cell deformability in sepsis." 1991 Crit Care Med; 19:732.

Pugliese, PT., "The skin, free radicals, and oxidative stress." Dermatol Nurs. Dec. 1995; 7(6): 361-9; quiz 370-1.

Ursini F. et al. "Diversity of glutathione peroxidases." 1995; 252:38-53.

Bradford, MM. "A rapid and sensitive method for the quantitation of microgram quantities of protein utilizing the principle of protein-dye binding," 1976; 72:248-254.

Carrillo, MC. "(−)Deprenyl induces activities of both superoxide dismutase and catalase but not of glutathione peroxidase in the striatum of young male rats." 1991; 48(6):517-521.

Ohkawa, H. et al. "Assay for lipid peroxides in animal tissues by thiobarbituric acid reaction." 1979; 95: 351-358.

Greenwald, B. "C-reactive protein elevation and the risk of colorectal cancer." 2004; 27(5): 246-247.

Kar A et al. "Relative efficacy of three medicinal plant extracts in the alteration of thyroid hormone concentrations in male mice." 2002 J Ethnopharmacol 81(2):281-5.

Malhotra CL et al. "Studies on Withania-ashwagandha, Kaul V. The effect of total alkaloids (ashwagandholine) on the central nervous system." 1965 Indian J Physiol Pharmacol 9(3):127-36.

Walter MF et al. "Serum levels of thiobarbituric acid reactive substances predict cardiovascular events in patients with stable coronary artery disease: a longitudinal analysis of the PREVENT study." Nov. 2004 J Am Coll Cardiol 44(1):1996-2002.

Somer Elizabeth. "Health is beauty when it comes to your complexion." Shape Magazine (1992), pp. 33-35.

PDR for Herbal Medicines (First Edn). Medical Economics Co., 1998, 630-633; 710-711; 729-730; 786-7; 871-873; 1138-1139.

Caramori, G. and Papi, A., "Oxidants and asthma," Thorax, 59(2): 170-173 (2004).

Kanta, J., "The role of hydrogen peroxide and, other reactive oxygen species in wound healing," Acta Medica (Hradec Králové) 54(3): 97-101 (2011).

Heistad, D. D., "Oxidative stress and vascular disease: 2005 Duff lecture," Arterioscler. Thromb. Vasc. Biol., 26(4): 689-695 (2006).

Stephens, J. W. et al., "Increased plasma markers of oxidative stress are associated with coronary heart disease in males with diabetes mellitus and with 10-year risk in a prospective sample of males," Clin. Chem., 52(3): 446-452 (2006).

Ozhan, Y. et al., "Oxidative status in rheumatoid arthritis," Clin. Rheumatol., 26(1):64-68 (2007).

Moreira, P. I. et al., "Oxidative stress and neurodegeneration," Ann. N. Y. Acad. Sci. 1043:545-552 (2005).

Albert MA. The role of C-reactive protein in cardiovascular disease risk. Curr Cardiol Rep 2000; 2(4):274-9.

Chaudhri, G. and Clark, I. A.: J Immunol, vol. 143, 1290-1294, No. 4, 1989.

Baeuerle, P. A. and Baltimore D.: Science, vol. 242, Oct. 1988, pp. 540-546.

Staal, F. J. T, et al.: Proc. Natl. Acad. Sci., USA, vol. 87, pp. 9943-9947, Dec. 1990.

Duh, E. J., et al.: Proc. Natl. Sci. Acad., USA, vol. 86, p. 5974-5978, 1989.

Morrow D, Rifai N, Antman E M, et al. C-reactive protein is a potent predictor of mortality independently of and in combination with troponin T in acute coronary syndromes: a TIMI 11A substudy. Thrombolysis in Myocardial Infarction. J Am Coll Cardiol 1998;31(7):1460-5.

Bogaty P, Poirier P, Simard S, et al. Biological profiles in subjects with recurrent acute coronary events compared with subjects with long-standing stable angina. Circulation 2001;103(25):3062-8.

Koenig W, Sund M, Frohlich M, et al. C-reactive protein, a sensitive marker of inflammation, predicts future risk of coronary heart disease in initially healthy middle-aged men: results from the MONICA (Monitoring Trends and Determinants in Cardiovascular Disease) Augsburg Cohort Study, 1984 to 1992. Circulation 1999; 99(2):237-42.

Moukarbel GV, Arnaout MS, Alam SE. C-reactive protein is a marker for a complex culprit lesion anatomy in unstable angina. Clin Cardiol 2001; 24(7):506-10.

Rifai N, Ridker PM. High-sensitivity C-reactive protein: a novel and promising marker of coronary heart disease. Clin Chem 2001; 47(3):403-11.

Yuan G, Wei J, Zhou, J, Hu H, Zhong T, and Zhang G. Expression of C5aR (CD88) of synoviocytes isolated from patients with rheumatoid arthritis and osteoarthritis. Chin Med J 2003; 116(9):1408-1412.

Steffens S., Inflammation and Atherosclerosis, Herz. Dec. 2004; 29(8):741-748.

Fraser A., Turnover of type II collagen and aggrecan in cartilage matrix at the onset of inflammatory arthritis in humans: relationship to mediators of systemic and local inflammation. Arthritis Rheum. Nov. 2003; 48(11):3085-95.

Dessein P H, Cardiovascular risk in rheumatoid arthritis versus osteoarthritis: acute phase response related decreased insulin sensitivity and high-density lipoprotein cholesterol as well as clustering of metabolic syndrome features in rheumatoid arthritis. Arthritis Res. 2002; 4(5):R5.

Sturmer T., Severity and extent of osteoarthritis and low grade systemic inflammation as assessed by high sensitivity C-reactive protein, Ann Rheum Dis. Feb. 2004; 63(2):200-5.

McKeown, DJ., The relationship between circulating concentrations of C-reactive protein, inflammatory cytokines and cytokine receptors in patients with non-small-cell lung cancer. Br J Cancer. Dec. 13, 2004; 91(12):1993-5.

Mcardle P A The relationship between interleukin-6 and C-reactive protein in patients with benign and malignant prostate disease, Br J Cancer. Nov. 15, 2004; 91(10):1755-7.

Alexandrakis, MG, The relation between bone marrow angiogenesis and the proliferation index Ki-67 in multiple myeloma, J Clin Pathol. Aug. 2004; 57(8):856-60.

Wang Q, Zhu X, Xu Q, Ding X, Chen Ye, Song Q. Effect of C-reactive protein on gene expression in vascular endothelial cells. Am J Physiol Heart Circ Physiol. Apr. 2005;288(4):H1539-45.

(56) References Cited

OTHER PUBLICATIONS

Kline K, Vitamin E and breast cancer, J Nutr. Dec. 2004; 134(12 Suppl):3458S-3462S.
Wright ME, Development of a comprehensive dietary antioxidant index and application to lung cancer risk in a cohort of male smokers. Am J Epidemiol. Jul. 1, 2004; 160(1):68-76.
Anderson K. Differential response of human ovarian cancer cells to induction of apoptosis by vitamin E Succinate and vitamin E analogue, alpha-TEA. Cancer Res. Jun. 15, 2004; 64(12)4263-9.
Al-Shaer MH., C-reactive protein and risk of colon cancer. JAMA. Jun. 16, 2004; 291(23):2819.
Skrzydlewska E, Lipid peroxidation and antioxidant status in colorectal cancer. World J Gastroenterol. Jan. 21, 2005; 11(3):403-6.
Boyd-Kimball D, Rodent Abeta(1-42) exhibits oxidative stress properties similar to those of human Abeta(1-42): Implications for proposed mechanisms of toxicity. J Alzheimer's Dis. Oct. 6, 2004; 6(5):515-25.
Cole NB, Murphy DD, Lebowitz J, Di Noto L, Levine RL, Nussbaum RL. Metal-catalyzed oxidation of alpha-synuclein: helping to define the relationship between oligomers, protofibrils, and filaments. J Biol Chem. Mar. 11, 2005;280(10):9678-90.
Zweier JL, Flaherty JT, Weisfeldt ML. Direct measurement of free radical generation following reperfusion of ischemic myocardium. Proc Natl Acad Sci U S A. Mar. 1987;84(5):1404-7.
Till GO, Guilds LS, Mahrougui M, Friedl HP, Trentz O, Ward PA. Role of xanthine oxidase in thermal injury of skin. Am J Pathol. Jul. 1989;135(1):195-202.
Barbosa DS, Decreased oxidative stress in patients with ulcerative colitis supplemented with fish oil omega-3 fatty acids., Nutrition Oct. 2003; 19(10):837-42.
Fantone JC, Ward PA. Role of oxygen-derived free radicals and metabolites in leukocyte-dependent inflammatory reactions. Am J Pathol. Jun. 1982;107(3):395-418.
Hurd TC, Dasmahapatra KS, Rush BF Jr, Machiedo GW. Red blood cell deformability in human and experimental sepsis. Arch Surg. Feb. 1988;123(2):217-20.
Fischman, C. M., et. al: The Journal of Immunology, vol. 127(6), p. 2257-2262, 1981.
Hamilos DL, Wedner HJ. The role of glutathione in lymphocyte activation. I. Comparison of inhibitory effects of buthionine sulfoximine and 2-cyclohexene-1-one by nuclear size transformation. J Immunol. Oct. 1985;135(4):2740-7.
Kalebic, T., et al.; Proc. Natl. Acad. Sci., USA; 88: 986-80, 1991.
Roederer M, Staal FJ, Raju PA, Ela SW, Herzenberg LA, Herzenberg LA. Cytokine-stimulated human immunodeficiency virus replication is inhibited by N-acetyl-L-cysteine. Proc. Natl Aced Sci U S A. Jun. 1990;87(12):4884-8.
Lipsky PE. Immunosuppression by D-penicillamine in vitro. Inhibition of human T lymphocyte proliferation by copper-or ceruloplasmin-dependent generation of hydrogen peroxide and protection by monocytes. J Clin Invest. Jan. 1984;73(1):53-65.
El-Hag A, Lipsky PE, Bennett M, Clark RA. Immunomodulation by neutrophil myeloperoxidase and hydrogen peroxide: differential susceptibility of human lymphocyte functions. J Immunol. May 1, 1986;136(9):3420-6.
Weiss, S. J.: J. Biol. Chem. 225: 9912-9917, 1980.
Hebbel, R. P., et al.: J. Clin. Invest., vol. 70, p. 1253-1259, 1982.
Vincent et al., Endocr Rev. Aug; 25(4):612-28 (2004).
Pasaoglu et al., Tohoku J Exp Med., July; 203(3):211-8 (2004).
Nomikos et al., Immunol Cell Biol 67:85-87 (1989).
Tabatabaie et al., FEBS Lett, 407:148-152 (1997).
Lenzen et al., Free Radical Biol. Med., 20:463-466 (1996).
Zhang, Q. et al., "A systems biology perspective on Nrf2-mediated antioxidant response," Toxicol Appl. Pharmacol., 244(1): 84-97 (2010).
Jung, K. A. and Kwak, M.-K., "The Nrf2 system as a potential target for the development of indirect antioxidants," Molecules, 15: 7266-7291 (2010).

Buettner, G. R., "Superoxide dismutase in redox biology: the roles of superoxide and hydrogen peroxide," Anticancer Agents Med. Chem., 11(4): 341-346 (2011).
Ma, Q. and He, X., "Molecular basis of electrophilic and oxidative defense: promises and perils of Nrf2," Pharmacological Reviews, 64: 1055-1081 (2012).
Nguyen, T. et al., "Regulatory mechanisms controlling gene expression mediated by the antioxidant response element," Annu Rev. Pharmacol. Toxicol., 43: 233-260 (2003).
Surh, Y.-J. et al., "Nrf2 as a master redox switch in turning on the cellular signaling involved in the induction of cytoprotective genes by some chemopreventive phytochemicals," Planta Med., 74: 1526-1539 (2008).
Griscavage JM, Wilk S, Ignarro LJ., Proc Natl Aced Sci USA., Inhibitors of the proteasome pathway interfere with induction of nitric oxide synthase in macrophages by blocking activation of transcription factor NF-kappa B., Apr. 16, 1996; 93(8):3308-12.
McCord et al., J. Biol. Chem., 244: 6049-6055 (1969).
Liu et al., Anal. Biochem. 245:161-166 (1997).
Li., J., Med Hypotheses. Is hypertension an inflammatory disease? 2005; 64(2):236-240.
Schiffrin E L., Vascular stiffening and arterial compliance: implications for systolic blood pressure. Am J Hypertens. Dec. 2004; 17(12 Pt 2):39S-48S.
Velmurugan, K. et al., "Synergistic induction of oxygenase-1 by the components of the antioxidant supplement Protandim," Free Radical Biology & Medicine, 46: 430-440 (2009).
Alam, J. et al., "Mechanism of heme oxygenase-1 gene activation by cadmium in MCF-7 mammary epithelial cells: role of p38 kinase and Nrf2 transcription factor," J. Biol. Chem. 275:27694-27702; 2000.
Bradford, M. M., "A rapid and sensitive method for the quantitation of microgram quantities of protein utilizing the principles of protein-dye binding," Anal. Biochem. 72:248-254; 1976, Abstract.
Gong, P. et al., Multiple basic-ieucine zipper proteins regulate induction of the mouse heme oxygenase-1 gene by arsenite, Arch. Biochem. Biophys. 405:265-274; 2002.
Hock, T. D. et al., "JunB and JunD regulate human heme oxygenase-1 gene expression in renal epithelial cells," J. Biol. Chem. 282:6875-6886; 2007.
Pugazhenthi, S, Akhov L, Selvaraj G, Wang M, Alam J. Regulation of heme oxygenase-1 expression by demethoxy curcuminoids through Nrf2 by a PI3-kinase/Akt-mediated pathway in mouse beta-cells, Am J Physiol Endocrinol Metab. Sep. 2007;293(3):E645-55.
Chou, T. C., "Theoretical basis, experimental design, and computerized simulation of synergism and antagonism in drug combination studies," Pharmacol. Rev. 58, pp. 621-681 (2006).
Wang, X.J. et al., "Generation of a stable antioxidant response element-driven reporter gene cell line and its use to show redoxdependent activation of Nrf2 by cancer chemotherapeutic agents," Cancer Res. 66, 10983-10994 (2006).
Hybertson, B. M. et al., "Oxidative stress in health and disease: the therapeutic potential of Nrf2 activation," Molecular Aspects of Medicine, 32: 234-246 (2011).
Chapple SJ, Siow RC, Mann GE. Crosstalk between Nrf2 and the proteasome: therapeutic potential of Nrf2 inducers in vascular disease and aging. Int J Biochem Cell Biol. Aug. 2012;44(8):1315-20.
Zhu H, Jia Z, Zhang L, Yamamoto M, Misra HP, Trush MA, Li Y. Antioxidants and phase 2 enzymes in macrophages: regulation by Nrf2 signaling and protection against oxidative and electrophilic stress. Exp Biol Med (Maywood). Apr. 2008;233(4):463-74.
Tabatabaie T, Vasquez-Weldon A, Moore DR and Kotake Y. Free radicals and the pathogenesis of Type 1 Diabetes: .beta cell cytokine-mediated free radical generation via cyclooxygenase-2. Diabetes, 52:1994-1999 (2003).
Lakshmi-Chandra M, Sing BB, Dagenais S. Scentific Basis for the Therapeutic Use of Withania somnifera (Ashwagandha): A Review. Alternative Medicine Review, 5(4):334-346 (2000).
Beers RF and Sizer IW. A Spectrophotometric Method for Measuring the Breakdown of Hydrogen Peroxide by Catalase. J Biol Chem 1952, 195-133-140.
Alam J, Stewart D, Touchard C, Boinapally S, Choi A and Cook J. Nrf2, a Cap'n'Collar Transcription Factor, Regulates Induction of the Heme Oxygenase-1 Gene. J Biol Chem 1999, 274:26071-26078.

(56) References Cited

OTHER PUBLICATIONS

Agyeman A, Chaerkady R, Shaw P, Davidson N, Visvanathan K, Pandey A and Kensler T. Transcriptomic and proteomic profiling of KEAP1 disrupted and sulforaphane treated human breast epithelial cells reveals common expression profiles. Breast Cancer Res Treat Feb. 2012; 132(1):175-187.

Bolibar I., et al. "Short-term prognostic value of lipid measurements in patients with angina pectoris. The ECAT Angina Pectoris Study Group: European Concerted Action on Thrombosis and Disabilities." Thromb Haemost Dec. 2000; 84(6):955-60.

Haverkate, F. et al. "Haemostasis factors in angina pectoris; relation to gender, age and acute-phase reaction. Results of the ECAT Angina Pectoris Study Group." Thromb Haemost Apr. 1995; 73(4):561-7.

Sagar S., et al. "Oxygen free radicals in essential hypertension," Mol Cell Biochem Apr. 1992; 111(1-2):103-8.

Hernandez RH et al. "Calcium antagonists and atherosclerosis protection in hypertension." Am J Ther. Nov.-Dec. 2003; 10(6):409-14.

Dawes PT et al. "Rheumatoid arthritis: treatment which controls the C-reactive protein and erythrocyte sedimentation rate reduces radiological progression." Br J Rheumatol Feb. 1986; 25(1):44-9.

Sowers M. et al. "C-reactive protein as a biomarker of emergent osteoarthritis." Osteoarthritis Cartilage Aug. 2002; 10(8):595-601.

Demopoulos HB. "The basis of free radical pathology." Fed Proc. Aug. 1973; 32(8):1859-61.

Massey KD. and Burton KP "alpha-Tocopherol attenuates myocardial membrane-related alterations resulting from ischemia and reperfusion," Am J Physiol Apr. 1989; 256 (4Pt 2): H1 192-9.

Bose B et al. "Membrane lipid peroxidation by UV-A: mechanism and implications." Biotechnol Appl Biochem Oct. 1990; 12(5):557-61.

Hamanaka et al. "Photoprotective effect of topically applied superoxide dismutase on sunburn reaction in comparison with sunscreen." J Dermatol Oct. 1990; 17(10):595-8.

Fuchs et al. "Impairment of enzymic and nonenzymic antioxidants in skin by UVB irradiation." J Invest Dermatol Dec. 1989; 93(6):769-73.

Pelle E et al. "An in vitro model to test relative antioxidant potential: ultraviolet-induced lipid peroxidation in liposomes." Arch Biochem Biophys Dec. 1990; 283(2):234-40.

Niway Y. "Lipid peroxides and superoxide dismutase (SOD) induction in skin inflammatory disease, and treatment with SOD preparations." 1989; 179 Suppl 1:101-6.

Fagan et al. "Serum levels of C-reactve protein in Crohn's disease and ulcerative colitis." Eur J Clin Invest Aug. 1982; 12(4):351-9.

Baker et al. "Reduced RBC versus plasma microvascular flow due to endotoxin." 1986; 20(2):127-39.

Mekechnie et al. "Modification by oxygen free radical scavengers of the metabolic and cardiovascular effects of endotoxin infusion in conscious rats." 1986 Circ Shock; 19(4):429-39.

Eck et al. "Low concentrations of acid-soluble thiol (cysteine) in the blood plasma of HIV-1-infected patients." 1989 Biol Chem Hoppe Seyler; 370(2):101-8.

Eck et al. "Influence of the extracellular glutamate concentration on the intracellular cystЄine concentration in macrophages and on the capacity to release cysteine." 1989 Biol Chem Hoppe Seyler; 370(2):109-13.

Kraut and Sagone AL Jr. "The effect of oxidant injury on the lymphocyte membrane and functions." J Lab Clin Med. 1981; 98(5):697-703.

Drash AL et al. "Effect of probucol on development of diabetes mellitus in BB rats." 1988 Am J Cardiol. Jul. 25; 62(3):27B-30B.

Rabinovitch A et al. "Human pancreatic islet beta-cell destruction by cytokines involves oxygen free radicals and aldehyde production." 1996; 81(9):3197-202.

Pauling L. "Vitamn C therapy of advanced cancer." 1980 N Engl J Med; 302(12):694-5.

D'Souza P. et al. "Brine shrimp lethality assay of *Bacopa monnieri*" 2002 Phytother Res 16(2):197-8.

Balogun, et al., "Curcumin activats the haem oxygenase-1 gene via regulation of Nrf2 and the antioxidant-responsive element," *Biochem. J.*, 2003; vol. 371: pp.887-895.

Bhattacharya, et al., "Antioxidant Activity of Glycowithanolides from Withania sominfera," *Ind. J. Exper. Biol,*, Mar. 1997; vol. 35: pp. 236-239.

Bhattacharya, et al., "Antioxidant Activity of Bacopa monniera in Rat Frontal Cortex, Striatum and Hippocampus," *Phytother. Res.*, 2000; vol. 14: pp. 174-179.

Blum, et al., "Inactivation of glutathione peroxidase by superoxide radical," *Arch Biochem Biophys*, Aug. 1985; vol. 240, No. 2: pp. 500-508 (abstract only).

Bray, et al., "Reduction and inactivation of superoxide dismutase by hydrogen peroxide," *Biochem. J.*, 1974, vol. 139; pp. 43-48.

Bridi, et al., "the Antioxidant Activity of Standardized Extract of Ginkgo biloba (EGb 761) in Rats," *Phytother. Res.*, 2001; vol. 15: pp. 449-451.

Chen, et al., "Protective effects of silybin and tetrandrine on the outcome of spontaneously hypertensive rats subjected to acute coronary artery occlusion," *International Journal of Cardiology*, 1993: vol. 41: pp. 103-108.

Dwivedi, et al., "Modification of coronary risk factors by medical plants," *Journal of Medicinal and Aromatic Plant Sciences*, 2000; vol. 22: pp. 616-620.

Eckert, et al., "Opposing Action of curcumin and green tea polyphenol in human keratinocytes," *Mol. Nutr. Food Res.*, 2006; vol. 50: pp. 123-129.

Falchi et al., Effects of Silymarin on Platelet Aggregation in Hypercholesterolaemised Rabbits, (1983) *Drugs Exptl. Clin. Res.* IX(6): 419-422.

Hamid, A. A., et al., "Characterisation of antioxidant activities of various extracts of Centella asiatica (L) Urban," *Food Chemistry* 77: 465-469 (2002).

Khafif, et al., "Quantitation of chemopreventive synergism between (−)-epigallocatechin-3-gallate and curcumin in normal, premalignant and malignant human oral epithelial cells," *Caricinogenesis*, 1998; vol. 19, No. 3: pp. 419-424.

Kono, et al., "Superoxide radical inhibits catalase," *Journal of Biological Chemistry*, May 1982; vol. 257, No. 10: pp. 5751-5754.

Larini, et al., "Effect of 4-hydroxynonenal on antioxidant capacity and apoptosis induction in Jurkat T cells," *Free Radic Res.*, May 2004; vol. 38, No. 5: pp. 509-516 (abstact only).

Luczaj, et al., "Green Tea Protection Against Age-Dependent Ethanol-Induced Oxidative Stress," *J. Tox. Envir. H., Part A.*, 2004; vol. 67: pp. 595-606.

Machiedo, et al., "Temporal Relationship of Hepatocellular Dysfunction and Ischemia in Sepsis," *Arch. Surg.*, Apr. 1988; vol. 123: pp. 424-427.

McCord, "Free Radicals and Myocardial Ischemia: Overview and Outlook," *Free Rad. Bio. Med.*, 1988, vol. 4: 9-14.

Mishra, et al., "Scientific basis for the therapeutic use of Withania somnifera (Ashwagandha): a review," *Alternative Medicine Review*, 2000; vol. 5, No. 4: pp. 331-346.

Mukhtar, et al., "Tea polyphenoals: prevention of cancer and optimizing health," *Am J Clin Nutr*, 2000, vol. 71 (suppl), pp. 1698S-1702S.

Naidu, et al., "Protective effect of Gingko biloba extract against doxorubicin-induced cardiotoxicity in mice," *Indian J Exp Biol.*, Aug. 2002, vol. 40, No. 8: pp. 894-900 (abstact only).

Nelson, et al., "The induction of human superoxide dismutase and catalase in vivo: a fundamentally new approach to antioxidant therapy," *Free Radical Biology & Medicine*, 2006; vol. 40: pp. 341-347.

Owuor, et al., "Antioxidants and oxidants regulated signal transduction pathways," *Biochem. Pharmacol.*, 2002; vol. 64: pp. 765-770.

Palasciano, et al., "The effect of silymarin on plasma levels of malondialdehyde in patients receiving long-term treatment with psychotropic drugs," *Current Therapeutic Research*, May 1994; May 1994; vol. 55, No. 5: pp. 537-545.

Panda, S., et al., "Withania somnifera and Bauhinia purpurea in the regulation of circulating thyroid hormone concentrations in female mice," *Journal of Ethnopharmacology*67:233-239 (1999).

(56) References Cited

OTHER PUBLICATIONS

Puapairoj, et al., "Effect of Etahnol on Paraquat Toxicity in F344 Rats," *Fd Chem. Toxic.*, 1994; vol. 32, No. 4: pp. 379-386.

Reddy A. C., et al., "Effect of dietary tumeric (Curcuma longa), on iron-induced lipid peroxidation in the rat liver," *Food and Chemical Toxicology* 32(3):279-283, 1994.

Singh, et al., "Chemomodulatory Action of Aloe vera on the Profiles of Enzymes Associated with Carcinogen Metabolism and Antioxidant Status Regulation in Mice," *Phytomedicine*, 2000: vol. 7, No. 3: pp. 209-219.

Shukla, et al., "Asiatiticoside-induced Elevation of Antioxidant Levels in Healing Wounds," *Phytother. Res.*, 1999; vol. 13: pp. 50-54.

Soto, et al., "Silymarin Increased Antioxidants Enzymec In Alloxan-Induced Diabetes In Rat Pancreas," *Comp. Biochem. Phys.*, 2003; Part C, vol. 136: pp. 205-212.

Swei, et al., "Mechanisms of Oxygen Free Radical Formation in Experimental Forms of Hypertension," On-line *Proceedings of the 5th Internet World Congresss on Biomedical Sciences '98* at McMaster University, Canada, Presentation No. SAswei0837, 1998.

Tripathi et al., "Bacopa monniera Linn. as an antioxidant: Mechanism of action," Jun. 1996, *Indian Journal of Experimental Biology*, 34:523-526

Ungvari, et al., "Vascular Inflammation in Aging," *Herz*, 2004; vol. 29, No. 8: pp. 733-740.

Wu, et al., "Upregulation of heme oxygenase-1 by Epigallocatechin-3-gallate via the phosphatidylinositol 3-kinase/Akt and ERK pathways," *Life Sciences*, 2006; vol. 78: pp. 2889-2897.

Observations by a third party concerning the patentability of the invention, dated Apr. 21, 2010 and received in the European Patent Office on May 10, 2010, filed in the European Patent Application No. 05734279.2 with Exhibits 1-8.

Ex. 1: Brhat Nighantu Ratnakara (Saligramanighahtubhusanam)—Compiled by Gangavisnu ssrikrsna Dasa, translated by Sri Dattarama Sriksnalala Mathura; vol. 4, (Part VII), edn. 197. Kemaraja Sriksrnadas Prakasana, Mumbai-4, p. 349.; Formulation ID: RS/4749, Formulation Name: Brhmigunaah 2.

Ex. 2: Kaiyadevanighntau (Pathyapathyavibodhakah), by Kaiyadeva, edited and translated by P.V. Sharma, et al., Chaukhambha Orientalia, Varanasi, Edn. $1^{st}$, 1979, p. 193; Formulation ID: RS6/376, Formulation Name: Aswagandha Guna.

Ex. 3: Al-Jaam'e-li-Mufradnat-al-Advia-wal-Aghzia, vol. IV, by Ziya Al-Din Abdullah Ibn Al-Baitar ($13^{th}$ century AD), Matba Amra, Cairo, Egypt, 1874 AD, p. 87; Formulation ID: MH2/128, Formulation Name: Kankar/Harshat'.

Ex. 4: Therayar Sekatuppu by Therayar, Pub: CCRAS Publications, Chennai (1979), pp. 27-32; Formulation ID: GP01/24, Formulation Name: Vaseekarika Kumari.

Ex. 5: Rasaratnasamuccayah by Vagbhattah, translated by Indra deva Tripathi, et al., Ed. $2^{nd}$ 2000, pp. 498-499; Formulation ID: RS1/1456, Formulation Name: Rasayane Raskalpa(76).

Ex. 6: Athmarakshaamirtham by Kandasamy Mudaliar, Pub: Hakkana Achagam, Chennai (1879), pp. 549-550; Formulation ID: AM05/2181, Formulation Name: Vipurathi Enni—1.

Chikithsa Rathna Deepam by Kannusamy Pillai, Pub: Rathna Nayakar & sons, Thirmagal Achagam, Chennai (1956) pp. 169-170; Formulation ID: SK03/157, Formulation NameL Santhaana Illagam.

Ex. 8: Muheet-e-Azam by Mohammad Azam Khan, vol. IV (Part I) ($19^{th}$ century AD), Matba Nizami, Kanpur, 1899 AD, p. 175; Formulation ID: FA1/328E1, Formulation Name: Nuskha-e-zulal.

International Search Report and Written Opinion, dated Aug. 31, 2005, from co-owned International Application No. PCT/US2005/009783.

Extended European Search and Opinion, dated Nov. 30, 2010, from co-owned European Patent Application No. 10179008.7.

Observations by a third party concerning the patentability of the invention, dated Feb. 22, 2011, and received in the European Patent Office on Mar. 1, 2011, filed in related European Patent Application No. 10179008.7, with Exhibits 1-9.

Ex. 1: Mohammad Kabiruddin, Bayaaz-e-Kabir, vol. II (Compiled), Daftar-al-Maseeh, Karol Bagh, New Delhi, 1938 AD, p. 142; Formulation ID: MA3/528; Formulation Name: Kusta Gau Danti.

Ex. 2: Bhavamisra, Bhavaprakasa, Edited and translated by Brahmashankara Misra & RupaLalaji Vaisya, Part 1: Chankhambha Sanskrit Sansathan, Varansi, Edn. $9^{th}$, 1999[Time of origin $16^{th}$ century], p. 461; Formulation ID: RS/3318A; Formulation Name: Brahmi.

Ex. 3: Mohammad Najmul Ghani Khan, Khazaain-al-Advia, vol. II($20^{th}$ century AD), Nadeem Yunus Printer / Sheikh Mohd Basheer & Sons, Lahore, 1911 AD, p. 784; Formulation ID: NA2/504H; Formulation Name: Dawa Barae Amraaz-e—Dimagh Wa Junoon.

Ex. 4: Mohammad Najmul Ghani Khan, Khazaain-al-Advia, vol. II($20^{th}$ century AD), Nadeem Yunus Printer / Sheikh Mohd Basheer & Sons, Lahore, 1911 AD, pp. 342-343; Formulation ID: AN2/324; Formulation Name: Chal.

Ex. 5: Ziya Al-Din Abdullah Ibn Al-Baitar, Al-Jaam'e-li-Mufradaat-al-Advia-wal-Aghzia, vol. IV ($13^{th}$ century AD), Matba Amra, Cairo, Egypt, 1874 AD, p. 87; Formulation ID: MH2/128; Formulation Name: Kankar/Harshaf.

Ex. 6: Brhat Nighantu Ratnakara (Saligramanighantubhusanam)—Compiled by Gangavisnu Srikrsna Dasa, Translated by Sri Duttarama Srikrsnalala; vol. 4 (Part VII), edn, 1997, Khemaraja Sriksrnadas Prakasana, Mumbai-4 [This book contains back references from 1000 BC to $20^{th}$ century], p. 349; Formulation ID RS/4749; Formulation Name: Brhmigunaah 2.

Ex. 7: Mohammad Azam Khan; Muheet-e-Azam, vol. III ($19^{th}$ century AD), Matba Nizami, Kanpur, 1887 AD, p. 166; Formulation ID: JA7/319W; Formulation Name: Dawa-e-deegar.

Ex. 8: Mohammad Azam Khan; Muheet-e-Azam, vol. IV (Part I)($19^{th}$ century AD), Matba Nizami, Kanpur, 1899 AD, p. 175; Formulation ID: FA1/328E1: Formulation Name: Nuskha-e-zulal.

Ex. 9: Lankapatiravana, Arkaprakasah—edited and translation by Indradeva Tripathi; Krishnadas Academy, Varanasi, edn, $1^{st}$ 1995, p. 44; Formulation ID: AK14/51B; Formulation Name: Haridra Arka Gunah.

Office Action dated May 31, 2011, from co-owned Japanese Patent Application No. 2007-505160.

SEQUENCE LISTING

```
<160> NUMBER OF SEQ ID NOS: 6

<210> SEQ ID NO 1
<211> LENGTH: 19
<212> TYPE: DNA
<213> ORGANISM: Mus musculus

<400> SEQUENCE: 1
gtgatggagc gtccacagc                                              19

<210> SEQ ID NO 2
<211> LENGTH: 18
<212> TYPE: DNA
<213> ORGANISM: Mus musculus

<400> SEQUENCE: 2
tggtggcctc cttcaagg                                               18

<210> SEQ ID NO 3
<211> LENGTH: 19
<212> TYPE: DNA
<213> ORGANISM: Homo sapiens

<400> SEQUENCE: 3
aggccaagac tgcgttcct                                              19

<210> SEQ ID NO 4
<211> LENGTH: 20
<212> TYPE: DNA
<213> ORGANISM: Homo sapiens
```

```
<400> SEQUENCE: 4
ggtgtcatgg gtcagcagct                                               20

<210> SEQ ID NO 5
<211> LENGTH: 24
<212> TYPE: DNA
<213> ORGANISM: Artificial Sequence
<220> FEATURE:
<223> OTHER INFORMATION: probe

<400> SEQUENCE: 5
cgacagcatg ccccaggatt tgtc                                          24

<210> SEQ ID NO 6
<211> LENGTH: 29
<212> TYPE: DNA
<213> ORGANISM: Artificial Sequence
<220> FEATURE:
<223> OTHER INFORMATION: probe

<400> SEQUENCE: 6
tcaacatcca gctctttgag gagttgcag                                     29
```

COMPOSITIONS FOR ALLEVIATING INFLAMMATION AND OXIDATIVE STRESS IN A MAMMAL

CROSS-REFERENCE TO RELATED APPLICATIONS

This application is a continuation in part of U.S. patent application Ser. No. 13/492,638, filed Jun. 8, 2012, entitled "COMPOSITIONS FOR ALLEVIATING INFLAMMATION AND OXIDATIVE STRESS IN A MAMMAL," now U.S. Pat. No. 8,435.574, which is a continuation of U.S. patent application Ser. No. 13/039,073, filed Mar. 2, 2011, entitled "COMPOSITIONS FOR ALLEVIATING INFLAMMATION AND OXIDATIVE STRESS IN A MAMMAL;" now U.S. Pat. No. 8,221,805, which is a continuation of U.S. patent application Ser. No. 12/546,063, filed Aug. 24, 2009, entitled "COMPOSITIONS FOR ALLEVIATING INFLAMMATION AND OXIDATIVE STRESS IN A MAMMAL;" now U.S. Pat. No. 7,923,045, which is a continuation of U.S. patent application Ser. No. 11/216,514, entitled "METHODS FOR ENHANCING ANTIOXIDANT ENZYME ACTIVITY AND REDUCING C-REACTIVE PROTEIN LEVELS," filed Aug. 31, 2005, now U.S. Pat. No. 7,579,026; which is a continuation of U.S. patent application Ser. No. 11/088,323, entitled "COMPOSITIONS FOR ALLEVIATING INFLAMMATION AND OXIDATIVE STRESS IN A MAMMAL," filed Mar. 23, 2005, now U.S. Pat. No. 7,241,461; U.S. Pat. No. 7,241,461 claims the benefit of priority under 35 U.S.C. §120 from U.S. Patent Application No. 60/555,80, filed on Mar. 23, 2004, U.S. Patent Application No. 60/590,528, filed on Jul. 23, 2004, U.S. Patent Application No. 60/604,638, filed on Aug. 26, 2004, U.S. Patent Application No. 60/607,648, filed on Sep. 7, 2004, U.S. Patent Application No. 60/610,749, filed on Sep. 17, 2004, U.S. Patent Application No. 60/643,754, filed on Jan. 13, 2005, and U.S. Patent Application No. 60/646,707, filed on Jan. 25, 2005, the contents of which are incorporated herein by reference in their entireties.

FIELD OF THE INVENTION

The present invention relates to compositions for alleviating inflammation and oxidative stress in a subject. Specifically, the present invention is directed to the field of natural remedies and the development of compositions to increase the antioxidant potential of a subject by inducing the subject's natural cellular defenses.

DESCRIPTION OF THE INVENTION

Free Radicals and Oxidative Stress

Over the past few decades, free and bound reactive radicals, highly reactive and thereby destructive molecules, have come to be appreciated increasingly for their importance to human health and disease. Many common and life-threatening human diseases, including atherosclerosis, cancer, and aging, have radical-based pathological reactions as an underlying mechanism of injury.

A radical, or a free radical, is a molecule with one or more unpaired electrons in its outer orbital shell. Free radicals are highly chemically reactive and usually short-lived molecular fragments. Because it needs to extract a second electron from a neighboring molecule to pair its single electron, a free radical often reacts with other molecules, which initiates the formation of many more free radical species in a self-propagating chain reaction. This ability to be self-propagating makes free radicals highly toxic to living organisms, and oxidative injury may lead to widespread biochemical damage within the cell. The molecular mechanisms responsible for this damage are complex. For example, free radicals may damage intracellular macromolecules, such as nucleic acids (e.g., DNA and RNA), proteins, and lipids. Free radical damage to cellular proteins may lead to loss of enzymatic function and cell death. Free radical damage to DNA may cause problems in replication or transcription, leading to cell death or uncontrolled cell growth. Free radical damage to cell membrane lipids may cause the damaged membranes to lose their ability to transport oxygen, nutrients or water to cells.

Some of the most common types of free radicals are those derived from oxygen, i.e., monoxides and other oxygen containing compounds, collectively known as reactive oxygen species (ROS). ROS comprising oxygen derived small molecules such as oxygen radicals: superoxide, hydroxyl, peroxyl, and alkoxyl; or the nonradicals: hypochlorous acid, ozone, singlet oxygen, and hydrogen peroxide, are highly unstable molecules that tend to react rapidly with adjacent molecules, donating, abstracting, or even sharing their outer orbital electron(s). This reaction not only changes the adjacent, target molecule sometimes in profound and beneficial ways, but it can also damage it, or, alternatively, the unpaired electron can be passed along to the target, i.e., as in a free radical, generating a second unwanted ROS, which can then go on to react positively or detrimentally with a new target. Oxygen ($O_2$) has two unpaired electrons in separate orbitals in its outer shell. Sequential reduction of molecular oxygen (equivalent to sequential addition of electrons) leads to the formation of a group of reactive oxygen species: superoxide anion ($O_2^{\cdot-}$), peroxide ($O_2^{\cdot-2}$) and hydroxyl radical ($\cdot OH$). The superoxide radical, although unreactive compared with many other radicals, may be converted by biological systems into other more reactive species, such as peroxyl ($ROO^-$), alkoxyl ($RO^-$) and hydroxyl ($OH^-$) radicals. Another radical derived from oxygen is singlet oxygen ($^1O_2$), an excited form of oxygen in which one of the electrons is present in a higher energy level upon absorption of energy. In fact, much of the high reactivity of ROS is due to their generation of such molecular chain reactions, effectively amplifying their effects many fold. At low concentrations, ROS serve as a second messenger in cell signaling. However, at higher concentrations and long-term exposure, ROS can damage cellular macromolecules such as DNA, proteins, and lipids in the form of lipid peroxidation, protein amino acid side-chain oxidation, and DNA single- and double-stranded breaks, which may lead to necrotic and apoptotic cell death. Antioxidants afford protection because they can scavenge ROS and free radicals before they cause damage to the various biological molecules, or prevent oxidative damage from spreading, e.g., by interrupting the radical chain reaction of lipid peroxidation. The reactivity of radicals in the body, and the burden on the body that results in eventual pathological conditions, is known as oxidative stress.

Oxidative stress results from the imbalance of free radicals generated during normal cellular metabolism and free radical or oxidant scavenging capacity of endogenous antioxidant enzymes. Many common and life-threatening diseases, including inflammatory conditions, wound healing, skin conditions, vascular and heart disease, atherosclerosis, diabetes, asthma, rheumatoid arthritis, cancer, neurodegeneration, and aging, have free radical reactions as an underlying mechanism of injury. (Caramori, G. and Papi, A., "Oxidants and asthma," Thorax, 59(2): 170-173 (2004); Kanta, J., "The role of hydrogen peroxide and other reactive oxygen species in wound healing," Acta Medica (Hradec Králové) 54(3):

97-101 (2011); Pugliese, P. T., "The skin, free radicals, and oxidative stress," Dermatol. Nurs., 7(6): 361-369; quiz 370-371 (1995); Heistad, D. D., "Oxidative stress and vascular disease: 2005 Duff lecture," Arterioscler. Thromb. Vasc. Biol., 26(4): 689-695 (2006); Stephens, J. W. et al., "Increased plasma markers of oxidative stress are associated with coronary heart disease in males with diabetes mellitus and with 10-year risk in a prospective sample of males," Clin. Chem., 52(3): 446-452 (2006); Ozkan, Y. et al., "Oxidative status in rheumatoid arthritis," Clin. Rheumatol., 26(1):64-68 (2007); Moreira, P. I. et al., "Oxidative stress and neurodegeneration," Ann. N.Y. Acad. Sci. 1043:545-552 (2005)).

It has been observed that the prime targets of both free radicals and ROS are polyunsaturated fats in the membrane lipids of cells. The oxidative deterioration of polyunsaturated fats is known as lipid peroxidation. Lipid peroxidation severely impairs membrane function, which is believed to lead to the disorganization of cell structure and function. Products of lipid peroxidation such as malondialdehyde, a known mutagen reactive with proteins and amino acids, are a good measure of the amount of oxidative stress on the body. Lipofuscin, another byproduct of lipid peroxidation, accumulates in the body with age, and it is believed that cytosolic buildup of this byproduct compromises brain function.

Due to environmental agents such as pollution, and lifestyle factors such as smoking or exercising, cellular exposure to free radicals is increased. Such increase may bring the body out of balance, especially where the mechanisms that produce antioxidants or remove ROS are insufficient to counter oxidative stress. A powerful combatant against the free radicals and ROS, however, is the body's own self defense system of naturally produced chemicals called antioxidants. These antioxidants act to terminate the propagation of free and bound radicals on ROS either by giving an electron to the free radical or ROS or by hindering their formation. However, the body's antioxidant defense system(s) can be impaired by the aging process and/or compromised, for example, by inflammation, microbial infection, viral infection, the progression of cancer or neurological disorders, and many other disorders characterized by, or caused in part by or exacerbated by, oxidative stress. The resulting damage can range from disruption of biological processes, killing of cells, and mutation of genetic material, which may lead to the occurrence of cancer.

ROS and Human Health

Our bodies are continuously exposed to free radicals and other ROS, from both external sources (sunlight, other forms of radiation, pollution) and generated endogenously; oxidative stress and ROS-mediated tissue injury is a final common pathway for a number of pathological processes. Oxidative stress results in increased immune system activity, which leads to inflammation, recruitment of more immune cells, and release of cytokines and acute phase proteins that further exacerbate the stress on the body.

Cytokines

It is postulated that in conditions where there is excessive free radical production or infection (e.g., AIDS), there is a severe alteration of interleukin-2 (IL-2) production, which secondarily occurs due to glutathione (GSH) depletion. IL-2 is a glycoprotein, which is produced in response to mitogens and antigenic stimuli; it and other cytokines show a multiplicity of functions. Glutathione levels regulate the alpha chain, the larger of the two IL-2 receptors. Decreasing GSH levels would decrease the affinity of IL-2 to its corresponding receptors; consequently there would be a compromise in the function of IL-2. It is postulated that maintenance of GSH levels by the use of the compositions of the present invention would allow IL-2 and its receptors to elicit the normal immunological response for this particular interleukin.

Excessive oxidative stress results in amplified production of TNF-alpha and IL-6. IL-6 initiates and encourages the production of acute phase proteins such as c reactive protein, serum amyloid A protein, fibrinogen, and mannan-binding lectin. IL-1, IL-6, and TNF-alpha stimulate, for example, CRP synthesis by inducing hepatic gene expression, which triggers a variety of inflammatory responses and associated pathologies (see, Albert Mass. The role of C-reactive protein in cardiovascular disease risk. Curr Cardiol Rep 2000; 2(4): 274-9). CRP is also a mediator of the complement system, part of the innate immune response (see, Yuan G, Expression of C5aR(CD88) of synoviocytes isolated from patients with rheumatoid arthritis and osteoarthritis. Chin Med J (Engl). 2003 September; 116(9):1408-12). The complement system provides further stimulus of TH1 and TH2 adaptive immune responses, which adds to the inflammatory response.

Production of tumor necrosis factor-alpha (TNF-alpha) by macrophages is stimulated by free radicals or oxidants (Chaudhri, G. and Clark, I. A.: J Immunol, vol. 143, 1990-1294, No. 4, 1989). TNF-alpha induces oxidant production by stimulating leukocytes, releasing arachidonic acid from leukocytes and releasing lysosomes. Therefore, enhancing plasma levels of antioxidants by administering the compounds of the present invention would decrease the production of TNF-alpha. It follows that, the maintenance/increase in antioxidant potential by administering the compositions of the present invention to a subject as described can prevent or treat cytokine-mediated tissue injury.

Inflammation

Inflammation can arise from infective agents (e.g., virion), trauma, chemical agents, immune reactions, metallic agents, and ionizing or thermal agents. The sine qua non of inflammation is heat, redness, edema, pain and loss of function (e.g., of the surrounding tissue). In any type of inflammation, characteristic inflammatory cells can be found, for example leukocytes, eosinophils, and macrophages/macrocytes. Each of these cell types produce radicals as part of a programmed response. Also as part of that "programmed" response are the production of inflammatory cytokines, such as TNF-alpha, CM-CSF and IL-2 and IL-6. These particular cytokines promote the production of oxidants such as nitric oxide and other reactive compounds. Oxidants are also generated as a byproduct of prostaglandin (PG) production, which is part of the propagation and amplification of the inflammatory process. Platelets are also involved in the inflammatory process by virtue of their ability to act as a plug (as in a clot); but also due to their liberation of platelet activating factor (PAF). PAF liberates arachidonic acid from leukocytes.

The production of prostaglandins is dependent upon the free radical tone (or concentration) of the microenvironment and metabolite synthesis. By decreasing the free radical tone and PG free radical intermediate metabolites, it is postulated that the pathological production of prostaglandins would be reduced, the amplification effect that PGs have as a role in the inflammatory process could be limited. Theoretically, either the lipooxygenase limb or the cyclooxygenase limb of the prostaglandin pathway could be affected by increased cellular antioxidants.

Free radicals or oxidants also have a plethora of different effects on the tissue in which it occurs, e.g., membrane damage, platelet adhesion, blood vessel intimal damage, etc. By increasing the antioxidant levels in areas where inflammation is occurring, it is postulated that the propagatory effect, tissue damage and pathologic physiologic reactions would be curtailed as well. The NF-KB transcription protein regulates the expression of a number of genes for proteins and cytokines involved in the inflammatory process (Baeuerle, P. A. and Baltimore, D.: Science, vol. 242, October, 1988). The activity and affinity that the NF-KB protein has for DNA is also regulated by GSH level (Staal, F. J. T, et al.: Proc. Natl. Acad. Sci., USA, vol. 87, pp 9943-9947, December 1990; Duh, E. J., et al.: Proc. Natl. Sci. Acad., USA, vol. 86, p 5974-5978, 1989). Enhancing levels of GSH decreases the activity and binding of NF-KB to DNA. By enhancing GSH levels, those cytokines and proteins involved in the inflammatory process would be decreased. The maintenance/increase of antioxidant potential by administering the compositions of the invention to a subject can, therefore, prevent or treat inflammation-mediated injury.

One important marker for inflammation is c reactive protein (CRP), a major acute phase response protein synthesized in the liver in response to the elaboration of acute phase response cytokines, such as interleukin-1 (IL-1), interleukin-6 (IL-6), and tumor necrosis factor alpha (TNF-alpha). Other associated acute phase proteins include serum amyloid A protein, fibrinogen, and mannan-binding lectin.

CRP concentrations are elevated in almost all inflammatory, infectious, and neoplastic diseases. Specific conditions include rheumatologic diseases (e.g., systemic lupus erythematosus, Sjogren's syndrome, rheumatoid arthritis), vasculitides (e.g., Wegener's granulomatosis), and chronic infections (e.g., tuberculosis, endocarditis). Certain malignant neoplasms, such as solid tumors, also may be associated with an elevated CRP level. Because CRP has a long half-life, CRP levels correlate well to its synthesis induced by persistent inflammation. Elevated levels of CRP are also associated with cardiovascular diseases such as endocarditis, angina pectoris, and myocardial infarction (see, http://www.americanheart.org/presenterjhtml?identifier=4648 and http://www.americanheart.org/presenterjhtml?identifier=3006541). Certain pathogens have been linked to atherogenesis and the development of clinically relevant coronary atherosclerosis. For example, cytomegalovirus (CMV), Herpes simplex virus (HSV) *Chlamydia pneumoniae*, and *Helicobacter pylori* have been associated with coronary artery disease (CAD), through inducement of vascular inflammation in addition to other mechanisms. This finding suggests that CMV contributes to atherogenesis by provoking an inflammatory response. CRP levels correlate with the clinical severity of CAD and with coronary events in both the acute and subacute phases of myocardial ischemia. Patients who are hospitalized for the treatment of unstable angina and have CRP concentrations above 0.3 mg/dL have significantly more ischemic episodes in the hospital than patients with lower CRP levels (see, Morrow D, Rifai N, Antman E M, et al. C-reactive protein is a potent predictor of mortality independently of and in combination with troponin T in acute coronary syndromes: a TIMI 11A substudy. Thrombolysis in Myocardial Infarction. J Am Coll Cardiol 1998; 31(7):1460-5). CRP concentrations are significantly lower in patients with stable angina pectoris than in those with unstable angina pectoris or an acute coronary syndrome. Patients with chronic stable angina who have stable, low CRP levels over time have fewer subsequent cardiovascular events during follow-up (see, Bogaty P, Poirier P, Simard S, et al. Biological profiles in subjects with recurrent acute coronary events compared with subjects with long-standing stable angina. Circulation 2001; 103(25):3062-8). On the other hand, in patients with unstable angina pectoris, elevated CRP levels are strong predictors of plaque instability.

Many trials have confirmed the association between high levels of CRP and the risk of future coronary events such as MI and sudden cardiac death. In the European Concerted Action on Thrombosis and Disabilities study (Bolibar I, von Eckardstein A, Assmann G, et al. Short-term prognostic value of lipid measurements in patients with angina pectoris. The ECAT Angina Pectoris Study Group: European Concerted Action on Thrombosis and Disabilities. Thromb Haemost 2000; 84(6):955-60), elevation of mean CRP levels by 20% or more was found in patients after an MI. CRP levels are higher in survivors of MI with or without a demonstrable coronary lesion and increase further if other sites, such as peripheral vasculature, also are involved. Hence, CRP levels may serve to represent the inflammatory burden.

In the Monitoring Trends and Determinants in Cardiovascular Disease trial (Koenig W, Sund M, Fröhlich M, et al. C-reactive protein, a sensitive marker of inflammation, predicts future risk of coronary heart disease in initially healthy middle-aged men: results from the MONICA (Monitoring Trends and Determinants in Cardiovascular Disease) Augsburg Cohort Study, 1984 to 1992. Circulation 1999; 99(2): 237-42), a long-term prospective study of cardiovascular risk, patients with the highest CRP levels had 2.6 times the risk of MI. In another study (Haverkate F, Thompson S G, Duckert F. Haemostasis factors in angina pectoris; relation to gender, age and acute-phase reaction. Results of the ECAT Angina Pectoris Study Group. Thromb Haemost 1995; 73(4):561-7), postinfarction angina occurred in only 14% of patients with a normal CRP level. By comparison, 64% of patients admitted with high CRP levels had evidence of postinfarction angina; nearly 42% required revascularization, and 21% had recurrent MI.

In patients with MI, increased CRP concentration is associated with the presence of complex angiographic lesions and the need for revascularization (Moukarbel G V, Arnaout M S, Alam S E. C-reactive protein is a marker for a complex culprit lesion anatomy in unstable angina. Clin Cardiol 2001; 24(7): 506-10). Elevated CRP levels also may represent a biomarker for patients who are most susceptible to reocclusion. In patients with stable CAD who underwent stent implantation following angioplasty, CRP levels increased over 96 hours in those with restenosis; in patients without restenosis, CRP levels peaked at 48 hours and then declined.

The normal serum concentration of CRP ranges from 3 mg/dL (90th percentile of the general US population) to more than 200 mg/dL. Generally, the American Heart Association has suggested that if hs-CRP level is lower than 1.0 mg/L, a person has a low risk of developing cardiovascular disease; if hs-CRP is between 1.0 and 3.0 mg/L, a person has an average risk, and if hs-CRP is higher than 3.0 mg/L, a person is at high risk for cardiovascular disease.

Because these ranges are not sensitive for the values required to determine cardiovascular risk in otherwise healthy persons, investigators have developed new, modified techniques to measure high-sensitivity CRP. The high-sensitivity CRP assay has been shown to detect concentrations below 0.2 mg/mL and uses labeled monoclonal or polyclonal anti-CRP antibodies in an enzyme-linked immunosorbent assay (ELISA) or an immunofluorescent assay (see, Rifai N, Ridker P M. High-sensitivity C-reactive protein: a novel and promising marker of coronary heart disease. Clin Chem 2001; 47(3):403-11).

Many conditions, activities, and medications affect levels of C-reactive protein. Increased levels are seen following allografts and graft occlusion, in connective tissue diseases (e.g., lupus erythematosus, Wegener's granulomatosis), arthritis, coronary artery disease, obesity, sepsis, in smokers, etc. Decreased levels of CRP are seen in response to inhibitory cytokines, exercise, and therapeutic doses of aspirin or 3-hydroxy-3-methylglutaryl-coenzyme A reductase inhibitors ("statins"). Accordingly, the compositions of the present invention, when administered to a subject having inflammation or the related/resultant disorders listed, can reduce CRP levels thereby reducing the inflammation and the severity of the related/resultant disorders. Administration of these compositions along with aspirin, naproxen, nambutome, other NSAID's or with statins appears to have a synergistic or additive effect on controlling inflammation and disease, depending on the particular combination.

Atherosclerosis

Atherosclerosis remains the major cause of death and premature disability in developed societies. Moreover, current predictions estimate that by the year 2020 cardiovascular diseases, notably atherosclerosis will become the leading global cause of total disease burden, defined as the years subtracted from healthy life by disability or premature death. Atherosclerosis is an inflammatory vascular disease characterized by endothelial activation, cellular influx, and production of mediators and cytokines This process leads to the formation of foamy macrophages and atheromatous plaques and, finally, to atherothrombotic disease. Atherosclerosis is associated with high morbidity and mortality.

Atherosclerosis is a complex process that leads to heart attack, stroke, and limb loss by the plugging of the arteries with atherosclerotic plaque. This plaque is a form of oxidized fat. It is now generally recognized that atherosclerosis is a chronic inflammatory disease, characterized by overrecruitment of leukocytes (monocytes and T-cells) to the site of inflammation. Vascular injury in response to cardiovascular risk factors promotes endothelial dysfunction, resulting in enhanced adhesion molecule expression and secretion of pro-inflammatory cytokines and chemokines. This, in turn, leads to adherence, migration and accumulation of leukocytes within atherosclerotic lesions. The recent findings on inflammatory processes involved in atherosclerosis development provide important links between risk factors and the mechanisms of atherogenesis. Thus, research interest has increasingly focused on inflammatory biomarkers as means of predicting the risk of future clinical events. Indeed, elevated plasma levels of molecules such as soluble intercellular adhesion molecule-1, interleukin-6 or C-reactive protein (CRP) have been shown to represent inflammatory markers of future cardiovascular risk. Among these, CRP has emerged as the most powerful and accessible for clinical use (see, Steffens S., Inflammation and Atherosclerosis, Herz. 2004 December; 29(8):741-748).

CRP is a member of the pentraxin protein family, which is so named because these proteins possess five identical subunits. CRP, which is elaborated dramatically during acute inflammation, augments the immune response to certain antigens, activates complement, and increases the monocytic production of tissue factors. CRP binds to phosphoryl choline on bacterial surfaces, acting as an opsonin and playing a pivotal role in host defense. Interestingly, CRP also appears to bind low-density lipoprotein cholesterol (LDL-C) in vitro, which suggests a direct interaction with the atherogenic lipids.

Inflammation in the vessels leads to the release of reactive oxides and radicals from the immune cells. When radicals react with lipids, the consequence is lipid peroxidation. While a number of factors influence the development and severity of atherosclerosis, a major factor is the ROS-mediated peroxidation of serum low-density lipoproteins (LDLs). The dietary approach to the prevention of heart disease and stroke is based partially on adding dietary antioxidants to limit LDL oxidation, as well as decreasing the intake of fat itself. These approaches already have made significant inroads into the mortality from heart disease, but the compositions of the present invention may offer a safe pharmacological prevention in the future that is not as dependent upon willpower as are diet and exercise. The maintenance/increase of antioxidant potential by administering the compositions of the present invention to a subject, therefore, can prevent or treat cardiovascular disease, e.g., atherosclerosis.

Hypertension

The link between the elevation of the arterial blood pressure and the production of vascular lesions remains an area of inquiry. Recent evidence in the spontaneously hypertensive rat and the salt dependent Dahl hypertensive strains indicate that there is an excessive production of superoxide anion in microvascular endothelium and in circulating leukocytes (Swei et al., Mechanisms of Oxygen Free Radical Formation in Experimental Forms of Hypertension, On-line Proceedings of the 5th Internet World Congress on Biomedical Sciences '98 at McMaster University, Canada, Presentation #SAswei0837, 1998). These studies examining the role of the endothelial xanthine oxidase as a source for the oxidative stress in the SHR and Dahl forms of hypertension and their normotensive controls indicated that both models of hypertension exhibit significantly elevated levels of XD and XO and enhanced oxidative stress in both the arterial and venular segments of the microcirculation compared with their respective normotensive controls. The elevation of the oxidative stress and blood pressures could be reduced significantly by blockade of XD and XO. Similarly, the maintenance/increase of antioxidant potential by administering the compositions of the present invention to a subject, therefore, can prevent or treat cardiovascular disease, e.g., hypertension.

Membrane abnormalities in essential hypertensives (EH) are known. The respiratory burst enzyme, NADPH oxidase is located in the cell membrane of the neutrophil (PMNLs) and its activity is important in generation of oxygen derived free radical (ROS). As noted above, ROS have been implicated in vascular changes in variety of conditions. Sagar and coworkers studied the status of ROS and antioxidants in EH (Sagar et al., Mol Cell Biochem. 1992 April; 111(1-2):103-8).

Sagar and coworkers studied ten, age and sex-matched, healthy controls (GpI) and 26 untreated EH (Gp IIA mild-8, Gp IIB Moderate-8, Gp IIC Severe-10). After clinical examination and basic laboratory evaluation of subjects, neutrophils isolated from their blood were studied. Chemiluminescence (CL) emitted by PMNLs after stimulation was measured (counts/min) in a luminometer and was taken as measure of OFR production and thereby of NADPH oxidase activity. The levels of antioxidants, superoxide dismutase (SOD) and reduced glutathione (GSH), were also estimated. Chemiluminescence was increased significantly (p less than 0.01) in Gp IIC (243.04+/−24.9×10(3) counts per minute) as compared to Gp IIA (2.80+/−1.87), Gp IIB (34.54+/−30.24) and Gp I (0.52+/−0.15) and SOD was reduced significantly (p less than 0.05) in all EH (Gp IIA 3.9+/−0.3 units per mg protein, Gp IIB 3.5+/−0.3 and Gp IIC 3.12+/−0.3) as compared to controls (4.1+/−0.2). Similarly GSH was reduced (p less than 0.05) in EH (Gp IIA 11.2+/−1.7 mg per gm protein, Gp IIB 8.5+/−1.1 and Gp IIC 6.6+/−0.3) as compared to Gp I (13.5+/−2.5).

In addition, there is significant evidence that indicates blood vessels thicken as a result of oxidative stress. Calcium antagonists, especially the highly lipophilic amlodipine, lacidipine and nisoldipine, are shown to possess antioxidant properties. These drugs reduce the oxidation of LDL and its influx into the arterial wall, and reduce atherosclerotic lesions in animals. Platelet production of malondialdehyde, a marker of oxygen free radical formation, is suppressed by amlodipine, lacidipine or nifedipine in hypertensive patients. In the Regression Growth Evaluation Statin Study (REGRESS), co-administration of calcium antagonist, amlodipine or nifedipine with pravasatin caused a significant reduction in the appearance of new angiographic lesions. In the Verapamil in Hypertension and Atherosclerosis Study (VHAS), verapamil was more effective than chlorthalidone in promoting regression of thicker carotid lesions in parallel with a reduction in the incidence of cardiovascular events. In the Prospective Randomized Evaluation of the Vascular Effects of Norvasc Trial (PREVENT), amlodipine slowed the progression of early coronary atherosclerosis in patients with coronary artery disease. In a subprotocol of the Intervention as a Goal in the Hypertension Treatment (INSIGHT) study, nifedipine GITS significantly decreased intima-media thickness as compared to co-amilozide (hydrochlorothiazide+amiloride). Preliminary results of the European Lacidipine Study on Atherosclerosis (ELSA) show that lacidipine reduced the intima-media thickness progression rate as compared to atenolol. Thus, selective calcium antagonists treat hypertension and are potential antiatherosclerotic agents. (see, Hernandez, R. H., Calcium antagonists and atherosclerosis protection in hypertension, Am J. Ther. 2003 November-December; 10(6): 409-14). Likewise, the maintenance/increase of antioxidant potential by administering the compositions of the present invention to a subject, alone or in conjunction with calcium channel antagonists therefore, can prevent or treat cardiovascular disease, e.g., atherosclerosis, arterial lesions, intima-media thickening, and hypertension. This is illustrated further in the examples below.

Arthritis

Rheumatoid arthritis (RA) is a chronic multisystem disease of unknown etiology. Although there are a variety of systemic manifestations, the characteristic feature of RA is persistent inflammatory synovitis, usually involving peripheral joints in a symmetric distribution. The potential of the synovial inflammation to cause cartilage destruction and bone erosions and subsequent changes in joint integrity is the hallmark of the disease.

Direct correlation between the increases in TNF-alpha and MMP-1 production and collagen degradation seen in the RA patient suggests that collagenase cleavage of cartilage collagen is related to the activities of TNF-alpha and MMP-1. The reduction in cartilage type II collagen synthesis in early RA may contribute to the developing pathology, since a lack of synthesis of this molecule would inhibit maintenance of cartilage matrix. (see, Fraser A., Turnover of type II collagen and aggrecan in cartilage matrix at the onset of inflammatory arthritis in humans: relationship to mediators of systemic and local inflammation. Arthritis Rheum. 2003 November; 48(11):3085-95).

Deterioration of the joint is less likely to occur when the patient CRP levels are consistently controlled (see, Dawes, P. T., Rheumatoid arthritis: treatment which controls the C-reactive protein and erythrocyte sedimentation rate reduces radiological progression. The British Journal of Rheumatology, Vol 25, 44-49). CRP levels may also be helpful in following response to therapy in rheumatic disorders, and may help to differentiate rheumatoid arthritis (high levels of C-reactive protein) from uncomplicated lupus (low levels of C-reactive protein). When used to evaluate patients with arthritis, serum is the preferred specimen; there is no reason to examine synovial fluid for C-reactive protein. CRP levels, insulin sensitivity, HDL cholesterol, triglycerides and hypertension are inter-related in RA patients, who typically experience a markedly increased frequency of cardiovascular disease (see, Dessein P H, Cardiovascular risk in rheumatoid arthritis versus osteoarthritis: acute phase response related decreased insulin sensitivity and high-density lipoprotein cholesterol as well as clustering of metabolic syndrome features in rheumatoid arthritis. Arthritis Res. 2002; 4(5):R5).

Generally, the first line of medical management of RA is the use of nonsteroidal anti-inflammatory drugs (NSAIDs) and simple analgesics to control the symptoms and signs of the local inflammatory process. These agents are rapidly effective at mitigating signs and symptoms, but they appear to exert minimal effect on the progression of the disease. NSAIDs block the activity of the Cox enzymes and therefore the production of prostaglandins, prostacyclin, and thromboxanes. As a result, they have analgesic, anti-inflammatory, and antipyretic properties. In addition, the agents may exert other anti-inflammatory effects. Since these agents are all associated with a wide spectrum of undesirable and even toxic side-effects, the natural dietary supplement compositions of the present invention provide a non-toxic alternative to NSAIDs.

Although osteoarthritis (OA) is thought to derive from defective chondrocyte metabolism and thus inherently lack the large scale systemic response of rheumatoid arthritis, there is increasing interest in the acute phase proteins in OA (see, Sowers M., C-reactive protein as a biomarker of emergent osteoarthritis. Osteoarthritis Cartilage. 2002 August; 10(8):595-601). Severity of pain, is associated with hsCRP levels in patients with advanced OA (see, Sturmer T., Severity and extent of osteoarthritis and low grade systemic inflammation as assessed by high sensitivity C-reactive protein, Ann Rheum Dis. 2004 February; 63(2):200-5).

Accordingly, the maintenance/increase of antioxidant potential in a mammal provides a method of ameliorating or decreasing tissue degradation and inflammation seen in arthritis (RA and OA). By administering the compositions of the present invention to a subject as described above, the compositions can therefore, prevent or treat OA and RA. The compositions may be given with other pharmaceutical agents, e.g., Relafen and other NSAID's or glucocorticoids (cortisone, dexamethasone, etc.) to achieve a greater anti-inflammatory effect.

Cancer and Other Malignancies

Cancer and other malignancies all entail unconstrained cell growth and proliferation based upon changes in the cell's genetic information. In most cases, for example, one or more genes that normally constrain cell growth and replication is/are mutated, or otherwise inactivated. These genetic deficiencies correspond directly with deletions and sequence changes in the genetic code, resident in the cell's DNA. A frequently seen final common cause of such DNA damage is free radical injury. Of the myriad injuries sustained by our DNA on a daily basis, most are repaired by normal DNA repair mechanisms within the cell, while some result in cell death. Since such injuries are sporadic and distributed somewhat randomly across the genome, most lethal DNA injuries are clinically inconsequential, resulting in the loss of a few cells among millions. However, when a single cell sustains an injury that impairs growth regulation, it can proliferate disproportionately and grow rapidly to dominate the cell population by positive natural selection. The result is a tumor, frequently a malignant one, where the constraint of growth and proliferation is particularly deficient. Therefore, free radical injury to the genetic material is a major final common pathway for carcinogenesis.

An approach to creating anti-tumor therapeutics that appears to have early success is aimed at preventing tumor induced angiogenesis, thereby reducing blood supply to the tumor to prevent growth and to kill the proliferating cells by starving them of nutrients and oxygen. While most candidate therapeutics are direct inhibitors of angiogenesis, other treatments are designed to prevent initiation of the angiogenesis response. Tumor formation is associated with localized inflammation, and increases of C-reactive proteins (CRP), which are well known prognostic indicators of patient survival (see, McKeown, D J., The relationship between circulating concentrations of C-reactive protein, inflammatory cytokines and cytokine receptors in patients with non-small-cell lung cancer. Br J. Cancer. 2004 Dec. 13; 91(12):1993-5). Elevated CRP levels are seen in many types of cancer, see for example, McArdle P A The relationship between interleukin-6 and C-reactive protein in patients with benign and malignant prostate disease, Br J. Cancer. 2004 Nov. 15; 91(10):1755-7; Saddler, D., C-reactive protein elevation and the risk of colorectal cancer, Gastroenterol Nurs. 2004 September-October; 27(5):246-7; and Alexandrakis, M G, The relation between bone marrow angiogenesis and the proliferation index Ki-67 in multiple myeloma, J Clin Pathol. 2004 August; 57(8):856-60.

CRP can significantly influence gene expression in the vascular endothelium. CRP is upregulated by IL-6, and increases expression of IL-8, ZF9, Activin A, MCP-1, EXT1, Cited2, PAI-1, Fibronectin-1, Gravin, Connexin-43, and SORL-1, and decreases expression of MAT2A, WRB, RCN1, TEB4, DNCL1 and Annexin A1 (see, Wang, Q., Effect of C-Reactive Protein on Gene Expression in Vascular Endothelial Cells, Am J Physiol Heart Circ Physiol. 2004 Dec. 9). Thus, CRP-responsive genes may have a broad functional role in cell growth and differentiation, vascular remodeling and solid tumor development Inhibiting CRP would provide an additional approach to current cancer therapies and may provide a prophylactic anticancer effect by inhibiting inflammation and angiogenesis.

By administering the compositions of the present invention to a subject as described above, the compositions can therefore, prevent or treat cancers that respond to antioxidant treatments. Such cancers include for example but not limited to, breast cancer (see, Kline K, Vitamin E and breast cancer, J. Nutr. 2004 December; 134(12 Suppl):34585-34625); lung cancer (see, Wright M E, Development of a comprehensive dietary antioxidant index and application to lung cancer risk in a cohort of male smokers. Am J. Epidemiol. 2004 Jul. 1; 160(1):68-76); ovarian cancer (see, Anderson K, Differential response of human ovarian cancer cells to induction of apoptosis by vitamin E Succinate and vitamin E analogue, alpha-TEA. Cancer Res. 2004 Jun. 15; 64(12):4263-9); and colon cancer (see, Al-Shaer M H., C-reactive protein and risk of colon cancer. JAMA. 2004 Jun. 16; 291(23):2819). In fact, colorectal carcinogenesis is associated with serious oxidative stress gradual advancement of oxidative-antioxidative disorders is followed by progression of colorectal cancer (see, Skrzydlewska E, Lipid peroxidation and antioxidant status in colorectal cancer. World J. Gastroenterol. 2005 Jan. 21; 11(3):403-6).

The compositions may be given with other pharmaceutical agents, e.g., glucocorticoids, camptothecins, mustard agents, and other chemotherapy drugs, to achieve a greater anti-tumor response and to control inflammation.

Radiation Injury

Radiation injury represents an important cause of ROS-mediated disease. With respect to commonly encountered levels of radiation, depending upon the situation, about two-thirds of the sustained injury is mediated not by the radiation itself, but by the ROS generated secondarily. This applies not only to the acutely toxic forms of radiation injury, but the long-term, mutagenic (and hence carcinogenic) effects as well.

An important clinical application of this principle is encountered regularly in the treatment of cancer by radiation therapy. Large tumors often outgrow their blood supplies and tumor cells die within the center, despite being well oxygenated at the periphery. Between these two regions is an area of tumor that is poorly oxygenated, yet remains viable. Radiation therapy of such tumors is particularly effective at the periphery, where an abundant concentration of oxygen is available to form tumorcidal ROS. The poorly oxygenated center is injured to a significantly smaller degree. While the dead cells in the center don't survive anyway, the poorly oxygenated, yet viable, cells between these two areas can survive a safe dose of radiation therapy, and thereby seed a later local recurrence of the tumor. This is a major reason why many large tumors are treated by a combination of radiation therapy (to kill the tumor at its advancing edges) and surgical removal of the bulk of the tumor, including these particularly dangerous remaining cells.

ROS can be generated within the cell not only by external sources of radiation, but also within the body as a by-product of normal metabolic processes. An important source of endogenous free radicals is the metabolism of some drugs, pollutants, and other chemicals and toxins, collectively termed xenobiotics. While some of these are directly toxic, many others generate massive free radical fluxes via the very metabolic processes that the body uses to detoxify them. One example is the metabolism of the herbicide paraquat. At one time, drug enforcement authorities used this herbicide to kill marijuana plants. Growers realized they could harvest the sprayed crop before it wilted, and still sell the paraquat-laced product. Many who smoked this product subsequently died of a fulminate lung injury. Fortunately, this approach has been abandoned as a particularly inhumane way to solve the drug problem.

While the paraquat story is a particularly striking example of a metabolic mechanism of free radical toxicity, many commonly encountered xenobiotics, including cigarette smoke, air pollutants, and even alcohol are toxic, and often carcinogenic to a large degree by virtue of the free radicals generated by their catabolism within our bodies. Moreover, there is accumulating evidence that a diet rich in fruits and vegetables, which are high in natural antioxidants, and low in saturated fat (a particularly vulnerable target for damage by ROS), reduces the risk of atherosclerosis and cancer. The maintenance/increase of antioxidant potential by administering the compositions of the present invention, therefore, can prevent or treat atherosclerosis and cancer.

The maintenance/increase of antioxidant potential by administering the compositions of the present invention to a subject, therefore, can prevent or treat radiation-mediated injury.

Neurological and Neurodegenerative Diseases

Neurological and neurodegenerative diseases affect millions of Americans. These include depression, obsessive-compulsive disorder, Alzheimer's, allergies, anorexia, schizophrenia, as well as other neurological conditions resulting from improper modulation of neurotransmitter levels or improper modulation of immune system functions, as well as behavioral disorders such as ADD (Attention Deficit Disorder) and ADHD (Attention Deficit Hyperactivity Disorder). Oxidative stress links diverse neuropathological conditions that include stroke, Parkinson's Disease, and Alzheimer's Disease and has been modelled in vitro with various paradigms that lead to neuronal cell death following the increased accumulation of reactive oxygen species. For example, immortalized neurons and immature primary cortical neurons undergo cell death in response to depletion of the anti-oxidant glutathione, which can be elicited by administration of glutamate at high concentrations.

A number of these diseases appear to have ROS toxicity as a central component of their underlying mechanism of nerve cell destruction, including, but not limited to, amyotrophic lateral sclerosis (ALS, or Lou Gehrig's disease), Parkinson's disease, and Alzheimer's disease. For example, Alzheimer's disease is a neurodegenerative disorder associated with aging and cognitive decline. Amyloid beta peptide (1-42) is a primary constituent of senile plaques-a hallmark of Alzheimer's disease—and has been implicated in the pathogenesis of the disease. Studies have shown that methionine residue 35 of beta(1-42) may play a critical role in Abeta(1-42)-mediated oxidative stress and neurotoxicity (see, Boyd-Kimball D, Rodent Abeta(1-42) exhibits oxidative stress properties similar to those of human Abeta(1-42): Implications for proposed mechanisms of toxicity. J Alzheimer's Dis. 2004 October; 6(5):515-25).

Additionally, oxidative stress is associated with the selective loss of dopaminergic neurons of the substantia nigra in Parkinson's disease. The role of alpha synuclein as a potential target of intracellular oxidants has been demonstrated by identification of posttranslational modifications of synuclein within intracellular aggregates that accumulate in PD brains, as well as the ability of a number of oxidative insults to induce synuclein oligomerization (see, Cole N B., Metal-catalyzed oxidation of alpha synuclein: helping to define the relationship between oligomers, protofilaments and filaments. J Biol. Chem. 2004 Dec. 21).

Accordingly, the maintenance/increase of antioxidant potential by administering the compositions of the present invention to a subject, therefore, can prevent or treat neurological and neurodegenerative diseases that have inflammation and oxidative stress as causative or complicating factors.

Ischemia/Reperfusion Injury

When an organ is deprived of its blood supply (ischemia) it is injured, not just by the temporary loss of oxygen, but also by the ROS that are generated by reaction with the oxygen that is reintroduced at reperfusion, when the blood supply is restored. In some clinical situations, this injury can prevented by giving antioxidants, sometimes even after the period of ischemia, but just prior to reperfusion. For example, the preservation of kidneys, livers, and other organs in solutions that contain antioxidants, as well as other agents, is now routine prior to their transplantation. Another example is the use of drugs that block the function of free radical generating enzymes prior to stopping the heart for cardiac surgery. These drugs help prevent reperfusion injury when the heart is restarted and flow is restored. This reperfusion injury mechanism also has been found to play an important role in patients suffering from multiple organ failure after trauma, massive surgery, or shock. Multiple organ failure is now the leading cause of death in intensive care units, and extensive efforts are under way to understand better how ROS contribute to this syndrome.

Ischemia, which is low tissue oxygen saturation of a given tissue, can occur in any organ system. All organs require a blood supply in order to remain viable. The intact organ whose arterial supply is compromised (either by partial or total occlusion) is rendered ischemic (e.g., coronary artery occlusion, organs awaiting transplantation, cerebral vascular accident, compartment syndrome, etc.). There are reversible and irreversible histological, physiological and biochemical changes which occur as a result of ischemic injury to tissue. End stage ischemia is universal and demonstrates necrosis. Demopoulos et al. (Fed. Proc. 32:1859-1861, 1973b) theorized that the necrosis observed in ischemic tissue was due to oxidants generated by the uncoupling of the oxidative phosphorylation chain in mitochondria. Zweir, et al., provided direct evidence that free radical production resulted from ischemia using electron spin resonance spectroscopy (Proc. Natl. Acad. Sci. USA, vol. 84, pp: 1404-1407). In reperfusion studies Zweir showed the alteration of one of the free radicals with the use of superoxide dismutase (which eliminated superoxide). In ischemic cardiac myocyte a depletion of ATP induces the release of arachidonic acid and palmitic acid. Vitamin E (Massey, K. D. and Burton, K. P.: Am. J. Physiol. 256 (Heart Circ. Physiol. 25): H1192-H1199, 1989), vitamin E acetate and selenium selenite have been used to protect tissue against free radicals, which have occurred in ischemia. It is postulated that enhancement of tissue antioxidants would eliminate the superoxide free radical, as well as other oxidants that are not double produced as a result of ischemia and prostaglandin metabolite production. The maintenance/increase of antioxidant potential by administering the compositions of the present invention to a subject, therefore, can prevent or treat ischemia/reperfusion injury, e.g., brain ischemia and heart ischemia (i.e., myocardial infarction).

Aging

Aging is a remarkably complex process that has managed to remain relatively opaque to scientific understanding. There is now evidence that aging is a series of processes, i.e., a series of controlled mechanisms, and not just the passive accumulation of wear and tear over the years. If aging is a series of processes, some of these processes are potentially controllable, or at least modifiable. One of the most important of these processes is comprised of an accumulation of the molecular injuries that are mediated by free radicals and other ROS. Recent studies indicate that the therapeutic manipulation of ROS metabolism can actually extend the total life span of mice to a significant degree. The maintenance/increase of antioxidant potential by administering the compositions of the present invention to a subject can, therefore, prevent or treat age-mediate injury.

Burns/Wound Healing

Burn wounds to skin and other organs can occur by ultraviolet radiation (UV), chemical agents, conductive or convective heat, electrocution, etc. Burns can occur in lung parenchyma by the inhalation of smoke or caustic gases (see section on tissue injury). Burn wounds to the skin are graded as first, second, and third degree burns (the most severe). It is postulated that any burn wound produces tissue damage, largely by the production of oxidants (Till, G. 0.: Am J. Pathol. July; 1325(1): 195-202, 1989). Liposomes (artificial membranes) when exposed to UV undergo peroxidation (Bose, B: Biotechnol Appl. Biochem, October, 12 (5): 557-61, 1990). It has been postulated that similar peroxidation occurs in skin when it is exposed to UV radiation (Somer, E.:Shape Magazine, p 33-35, November 1992; Hamanka, H.: J. Dermatol, October 17(10):595-8, 1990). Exposure of skin to UV varies in intensity and length of exposure. Daily exposure to UV (e.g., sunlight) has been postulated to result in skin wrinkling Depending on the intensity and/or length of skin exposure to UV light, first, second or third degree burns can result.

Hairless mice exposed to a single exposure of UV resulted in a broad range decrease of antioxidants: glutathione, beta-carotene, alpha-tocopherol. The enzyme activity of catalase and glutathione reductase was also decrease (Fuchs, J.: J. Invest Dermatol, December, 93(6): 769-73, 1989). These decreases in the concentration of antioxidants and enzyme activity in skin due to UV exposure supports the concept of the occurrence of free radicals in skin. It is postulated that lipid peroxidation could be inhibited by an enhancement of antioxidants in skin. Lipid peroxidation in liposomes exposed to UV can be inhibited by placement of beta-carotene or alpha-tocopherol in liposomes (Pelle, E.: Arch. Biochem. Biophys. December 283 (2): 234-40, 1990).

Excessive free radical production has been cited as a factor in delayed wound healing (Yukie, N.: Dermatolgica, 179 (suppl 1): 101-106, 1989). The maintenance/increase of antioxidant potential by administering the compositions of the present invention to a subject of antioxidants would, therefore, ameliorate the effects of pathologic oxidants and prostaglandin production as well as promote wound healing in various skin injuries.

Tissue Injury and Degeneration

Tissue injury occurs as a result of an inflammatory focus occurring in the area of a cell or an organ. For example plasma oxidative stress occurs in patients with ulcerative colitis, and omega-3 fatty acids are under study as free radical scavengers for protecting the patients against the overall effect of oxidative stress (see, Barbosa D S, Decreased oxidative stress in patients with ulcerative colitis supplemented with fish oil omega-3 fatty acids., Nutrition. 2003 October; 19(10):837-42). C-reactive protein levels corresponded closely with clinical and pathological indices of relapse, remission and response to therapy in patients with Crohn's disease. Assay of serum C-reactive protein provides an objective criterion of inflammatory activity, which may be useful in the assessment, management and study of Crohn's disease (see, Fagan, E. A., Serum levels of C-reactive protein in Crohn's disease and ulcerative colitis. Eur J Clin Invest. 1982 August; 12(4):351-9). Accordingly, CRP levels may also be helpful in following response to therapy for tissue injuries, and may help to differentiate in Crohn's disease (high C-reactive protein) from ulcerative colitis (low C-reactive protein).

Inflammation can occur due to a local inducement (e.g., hepatitis) or due to an injury occurring to one organ in a remote location and another discontiguous organ, which also sustains an injury (e.g., severe burns occurring to skin (the first organ) with subsequent injury to the lungs (the second organ)). In either case, local or remote tissue injury is believed to be mediated by activated leukocytes, which release oxidants. Oxidants released from leukocytes react with cellular (organ) membranes (Fantone, J. C. and Ward, P. A.: Am. J. of Path., vol. 107(3), P. 397-418, 1982). Repeated cellular membrane exposure to oxidants decreases antioxidant levels, which increases their susceptibility to damage. Increasing the levels of antioxidants in the extracellular and/or intracellular, and/or the lipid-aqueous interface is postulated to thwart oxidant damage to vital cellular structures. The maintenance/increase of antioxidant potential by administering the compositions of the invention to a subject can, therefore, prevent or treat ROS-mediated tissue injury or other types of inflammatory tissue degeneration.

Sepsis

Sepsis is characterized as a systemic infection by a microorganism. Frequently it is fatal and if not fatal increases the morbidity of the patient. In sepsis, red blood cells become sticky and deformed (Baker, C. H., et al.: Circ. Shock 20:127-139, 1986; Powell, J., et al.: Critical Care Med., vol 19 (5), 1991), which can lead to occlusion of the microvasculature. Cardiac output is increased, but in the kidney, liver, and musculature blood flow is decreased (Hurd, T. C., et al.: Archives of Surg., vol. 123, 1988). Evidence of free radical damage has been demonstrated in in vitro and in vivo studies involving shock induced by endotoxins (McKechnie, K., et al.: Circ. Shock 19: 429-439, 1986). Findings include increased vascular permeability, damaged mitochondria, disruption of calcium transport by the sarcoplasmic reticulum, and the activation of the complement system (particularly C5a). In septic infections, serum levels of acute phase proteins, particularly CRP, are elevated, which increases activation of the complement response as well as other cell mediated responses.

The maintenance/increase of antioxidant potential by administration of the compositions of the present invention to a subject can, therefore, prevent or treat sepsis-mediated inflammatory cellular damage.

GSH Deficiency

Artificial depletion of glutathione interferes with normal T cell function, particularly within the first 30-60 minutes of activation (Fischman, C. M., et. al: The Journal of Immunology, vol. 127(6), p 2257-2262, 1981; Hamilos, D. L. and Wedner, H. H.: Journal of Immunology, vol. 135 (4), 1985). Glutathione deficient T cells showed a decrease in thymidine incorporation and blast transformation. The greater the depletion of glutathione the longer it took cells to recover to normal levels. If cellular GSH depletion was severe enough the cells never recovered to normal GSH levels. Increased glutamate levels, which are found in AIDS patients (Eck, H.-P. and Droge, W.: Bio. Chem. Hoppe-Seyler, vol. 370, pp 109-113), appear to inhibit the transport of cystine into macrophages. Under normal circumstances cysteine is reduced to cysteine by the macrophages. Cysteine is exported into the microenvironment for the use of T cells for the ultimate conversion to intracellular glutathione. T cells cannot utilize cystine. In AIDS patients glutathione is depleted (Eck, H.-P, et al.: Biol. Chem. Hoppe-Seyler, vol. 370, pp 101-108), which is postulated to adversely affect T cell function. This scenario is believed to be similar to the experimental studies, which demonstrated abnormal T cell function as a result of artificial GSH depletion. The maintenance/increase of antioxidant potential by administering the compositions of the present invention to a subject can, therefore, prevent or treat GSH deficiency.

AIDS

There is considerable evidence which indicates that HIV infection and subsequently ARC/AIDS is by in large a free radically mediated disease. This analysis can be made indirectly as judged by the antioxidant levels in humans and their consequences on the immune system. One of those antioxidants, glutathione (GSH), is decreased as a result of HIV infecting the host. The GSH levels continue to decrease as the disease progresses through ARC and finally to AIDS. Micromolar changes in GSH levels have an untoward effect on the function of T lymphocytes (which can be viewed as the pivotal leader of the immune system). GSH shows a multiplicity of uses in the immune system. Thiol concentrations (e.g., GSH) regulate the replication of HIV genomic expression (Kalebic, T., et al.: Proc. Natl. Acad. Sci., USA; 88: 986-90, 1991; Roeder, M., et al.,: Porc. Natl. Acad. Sci., USA, vol. 87, p 4884-4888). Increasing the concentrations of thiols (GSH, NAC, GSE (glutathione ester)) in culture medium of U1 cell line (promonocytes) results in suppression of viral assembly, HIV reverse transcriptase production and viral replication. The maintenance of antioxidant potential by administering the compositions of the invention to a subject can, therefore, prevent or treat HIV-mediated injury.

Immunomodulation

There are numerous activators of leukocytes (e.g., exposure to ingestible particles, certain soluble factors such as complement, lectins, phorbol esters, etc.). A consequence of leukocyte activation is the release of the MPO system ($H_2O_2$+halide+myleoperoxidase) and other oxidants. The more potent the stimulus of activation of leukocytes is, the greater the release of oxidants and the greater the suppression of T lymphocytic function. When activated leukocytes were combined with T lymphocytes and catalase, there was no suppression of lymphocytic function; monocytes (which contain enzymatic antioxidants: glutathione peroxidase, catalase, myeloperoxidase) were used in lieu of catalase, again there was no suppression (Lipsky, P. E.: J. Clin. Invest. 73:53, 1984). Antibody production by B lymphocytes showed a similar susceptibility to free radical damage as did lymphocytes (E1-Hag, A., et al.: J. of Immunol., vol. 136 (9), 1986). A following is a rank order for various lymphocytic functions to free radical attack: immunoglobulin secreting cells were the most sensitive (particularly to the MPO system); Natural Killer cell activity, DNA synthetic responses to PHA and Con A were intermediate; and the DNA response to PWM was the least susceptible. Monocytes/macrophages have approximately 15-20 times higher catalase content in comparison to lymphocytes (Meerhof, L. J. and Roos, D.: J. Reticulendothel. Soc. 28: 419) and would therefore be much less susceptible to oxidative damage. Lymphocytes exposed to a free radical generating system demonstrate changes in membrane characteristics: 63% decrease in E rosette formation, 44% decrease in surface immunoglobulins and 90% decrease in cap formation (Kraut, E. H. and Sagone, A. L.: J. of Lab. Clin. Med., November 1981, p 697-703). The maintenance/increase of antioxidant potential by administering the compositions of the invention to a subject can, therefore, prevent or treat immune damage by ROS.

Sickle Cell Anemia

Sickle cell anemia is a genetically determined disease. Analysis of sickle cell patients RBC (HbS) demonstrates a number of peculiarities of the membrane: frozen spectrin shell of irreversibly sickled RBC, an abnormal orientation of the lipid bilayer phospholipids, deficient calcium-ATPase, a propensity for HbS RBCs to adhere to vascular endothelium, and oxidized thiol groups on the HbS molecule. It is the characteristic of the tendency of adherence to the vascular endothelium, which is the likely primary pathogenesis of the disease, which is occlusion of the microvasculature. Consequently, ischemic injury occurs to organs (see section on ischemia). Additional evidence of free radical damage to HbS is a deficiency of alpha-tocopherol, increased amounts of malondialdehyde, and abnormal group cross linking by malonadehyde. Superoxide anion can enter into erthrocytes via anion channels, resulting in the formation of methemoglobin and the ultimate lysis of erythrocytes (Weiss, S. J.: J. Biol. Chem. 225: 9912-9917, 1980). Sickle RBCs spontaneously generate sixty percent greater quantities of superoxide and approximately 75% more hydrogen peroxide when compared with controls (Hebbel, R. P., et al.: J. Clin. Invest., vol. 70, p. 1253-1259, 1982). Superoxide dismutase is increased by about 50%, glutathione peroxidase and catalase were decreased by approximately 50% and 29% respectively. Glutathione and vitamin E levels were significantly reduced. It is postulated that by increasing both bone narrow and serum antioxidant levels that free radicals produced by sickled RBCs would be markedly reduced. Accordingly, maintenance/increase of antioxidant potential by administering the compositions of the present invention is useful to prevent or treat anemia-mediated injury.

Diabetes

Diabetes mellitus (DM) is a common disease affecting over 124 million individuals worldwide. DM is associated with high risk of atherosclerosis and renal, neural, and ocular damage. Oxidative stress results from a cell or tissue failing to detoxify the free radicals that are produced during metabolic activity. Diabetes is characterized by chronic hyperglycemia that produces dysregulation of cellular metabolism. Vincent and coworkers have suggested that diabetes overloads glucose metabolic pathways, resulting in excess free radical production and oxidative stress (Vincent et al., Endocr Rev. August; 25(4):612-28 (2004). Vincent and coworkers have presented evidence to support the idea that both chronic and acute hyperglycemia cause oxidative stress in the peripheral nervous system that can promote the development of diabetic neuropathy. Proteins that are damaged by oxidative stress have decreased biological activity leading to loss of energy metabolism, cell signaling, transport, and, ultimately, to cell death. Examination of the data from animal and cell culture models of diabetes, as well as clinical trials of antioxidants, strongly implicates hyperglycemia-induced oxidative stress in diabetic neuropathy. Vincent et al., concluded that superior antioxidative therapies remains essential for the prevention of neuropathy in diabetic patients (Vincent et al., Endocr Rev., August; 25(4):612-28 (2004). The maintenance/increase of antioxidant potential by administering the compositions of the invention to a subject can, therefore, prevent or treat diabetes-related, ROS-mediated tissue damage.

Pasaoglu and coworkers, investigated lipid peroxidation, resistance of plasma and red blood cells to oxidation, and antioxidant defense system in erythrocytes and sera in patients with type 2 diabetes mellitus (Pasaoglu et al., Tohoku J Exp Med., July; 203(3):211-8 (2004). One group included newly diagnosed 20 patients and the other included 20 patients treated with oral antidiabetic agents (OAD). Twenty healthy subjects served as controls. Serum and red blood cell malondialdehyde (MDA), glutathione (GSH), resistance to oxidation, and plasma thiol (total —SH) levels were measured. In addition, glycated hemoglobin, serum fructosamine, uric acid, total protein, total cholesterol, triglyceride and glucose levels were determined. Although newly diagnosed patients had higher serum and erythrocyte MDA levels than those of controls, the highest levels of MDA were determined in patients treated with OAD. MDA levels after exposing to oxidation increased in OAD group more than in newly diagnosed patients. Total —SH and erythrocyte GSH levels of the both diabetic groups were lower than controls. These results showed that serum and erythrocyte lipid peroxidation was increased in diabetic patients. The sera of the patients showed a decreased resistance against oxidation. Pasaoglu and coworkers proposed that the effect of increased free radicals may be prevented by antioxidant systems in early stages of type 2 diabetes but in advanced stages this relationship is impaired owing to decreased antioxidant activity. Decreased red blood cell GSH and serum total —SH levels may be due to a compensation mechanism of the antioxidants. The maintenance/increase of antioxidant potential by administering the compositions of the invention to a subject can, therefore, prevent or treat diabetes-related (e.g., diabetes type-2), ROS-mediated tissue damage.

Administration of the antioxidant enzymes superoxide dismutase (SOD) and catalase prevented destruction of islet allografts in NOD mice (Nomikos et al., Immunol Cell Biol 67:85-87 (1989)). Furthermore, the antioxidant probucol was shown to reduce the diabetes incidence and to delay diabetes onset in the BB rats (Drash A L et al., Am J Cardiol, 62:27 B-30B (1988)). Tabatabaie and coworkers have demonstrated that chronic administration of the free radical scavenger phenyl-N-tert-butylnitrone (PBN) inhibits STZ-induced diabetes in mice (Tabatabaie et al., FEBS Lett, 407:148-152 (1997)). The low level of antioxidant enzymes such as SOD, catalase, and glutathione peroxidase in the islets is another indication that .beta.-cells are exceptionally vulnerable to oxidative damage (Lenzen et al., Free Radical Biol. Med., 20:463-466 (1996)).

ROS generation, evidenced by the formation of lipid peroxidation products, is believed to be the ultimate cause of cytokine-mediated death of .beta.-cells in isolated islets (Rabinovitch et al., J. Clin. Endocrinol. Metab., 81:3197-3202 (1996)). Tabatabaie and coworkers recently demonstrate the formation of free radicals in the pancreatic islets as a result of cytokine treatment using EPR spectroscopy (Tabatabaie et al., Diabetes, August (2003)). Based on their studies, Tabatabaie and coworkers concluded that free radicals have a role in the pathogenesis of type 1 diabetes through .beta.-cell cytokine-mediated free radical generation in the pancreatic Islets (Tabatabaie et al., Diabetes, August (2003)). The maintenance/increase of antioxidant potential by administering the compositions of the invention to a subject can, therefore, prevent or treat diabetes-related (e.g., diabetes type-1), ROS-mediated tissue damage.

As the products of normal cell respiration and metabolism, ROS are generally regulated by cellular defense systems present in the body, which reduce the amount of damage that free and reactive species radicals may cause by scavenging free radicals or enzymatically converting the free radicals to less toxic chemical species, thereby serving a physiological role as antioxidants.

The mitochondrial respiratory chain and enzymatic reactions catalyzed by NAD(P)H oxidase, xanthine oxidase, cyclooxygenases, and lipoxygensase, are endogenous sources of ROS. Besides being produced by oxidative respiration in mitochondria, ROS also arise as intermediates in many other metabolic processes in the cell that include but are not limited to β-oxidation of fatty acids in the peroxisome, cytochrome P450 enzyme-catalyzed metabolic reactions in the endoplasmic reticulum, and prostaglandin synthesis from arachidonic acid at the cell membrane, as part of cellular defense against invaded pathogens, etc. Leakage of ROS from the innate immune response may unnecessarily subject the host cells to high concentrations of the bactericidal reactive species, leading to undesirable toxicity. (Zhang, Q. et al., "A systems biology perspective on Nrf2-mediated antioxidant response," Toxicol Appl. Pharmacol., 244(1): 84-97 (2010); (Jung, K. A. and Kwak, M.-K., "The Nrf2 system as a potential target for the development of indirect antioxidants," Molecules, 15: 7266-7291 (2010)).

Cellular Defenses Against Oxidative Stress

To restrict the potential toxicity of ROS, most species have developed elaborate strategies to cope with oxidative stress constituting a cellular antioxidant system that contains a suite of antioxidant small molecules (such as glutathione (GSH) and thioredoxin (Txn)) that neutralize ROS by direct interactions with them and detoxifying enzymes that can quickly remove or detoxify reactive species, such as superoxide dismutase (SOD), catalase (CAT), glutathione peroxidase (GPx), and peroxiredoxins (Prdx). (Zhang, Q. et al., "A systems biology perspective on Nrf2-mediated antioxidant response," Toxicol Appl. Pharmacol., 244(1): 84-97 (2010); (Jung, K. A. and Kwak, M.-K., "The Nrf2 system as a potential target for the development of indirect antioxidants," Molecules, 15: 7266-7291 (2010)). Studies conducted have indicated that these antioxidants can work synergistically as the reactions they catalyze are metabolically sequential, beginning first with SOD followed by the actions of CAT and GPX.

Superoxide Dismutases (SODs)

SODs are a group of ubiquitous antioxidant enzymes containing redox-active metal ions such as copper, manganese or iron at the active sites. SODs are a class of enzymes that catalyze reactions similar to: $O^{2-}+O^{2-}+2H^+ \rightarrow H_2O_2+O_2$.

SOD is found in the body, primarily in three forms: (1) in the cytoplasm as Cu—Zn SOD; (2) in the mitochondrion as Mn-SOD; (3) and in an extracellular environment as CuSOD. Accordingly, the body is dependent upon the presence of zinc, copper, and manganese for the manufacture of SOD. The role of SOD in the defense system is to remove superoxide radicals. During the removal of superoxide radicals by SOD, both hydroxyl and oxygen radicals are produced, which are catalyzed by CAT and GPX respectively.

The major flow of electrons in normal cell metabolism is through mitochondrial electron transport chain (ETC) constituting a high flux circuit, which causes reduction of oxygen to water producing energy that is harvested as adenosine triphosphate (ATP). Less than 1% of the oxygen is diverted via a one-electron reduction of dioxygen to produce the superoxide radical ($O_2^{\cdot-}$) constituting a low flux circuit that plays a role in regulation of metabolism and initiation of cell signaling. This low flux circuit is controlled in part by the SODs. The superoxide ion ($O_2^{\cdot-}$) can be an oxidant, a reductant, or both depending on the coordination environment of the metal at the SOD active site. Superoxide reacts with the metal-containing active site of SODs alternately as reductant and then as oxidant, yielding oxygen and $H_2O_2$. The steady state level of superoxide ($O_2^{\cdot-}$) is inversely proportional to the intracellular level of SOD. (Buettner, G. R., "Superoxide dismutase in redox biology: the roles of superoxide and hydrogen peroxide," Anticancer Agents Med. Chem., 11(4): 341-346 (2011)).

Catalase

Catalase (CAT) is present in the peroxisomes of nearly all aerobic cells, and serves to protect the cell from the toxic effects of hydrogen peroxide by catalyzing its decomposition into molecular oxygen and water without the production of free radicals.

The overall reaction is as follows: $2H_2O_2 \rightarrow 2H_2O+O_2$.

The protein exists as a dumbbell-shaped tetramer of four identical subunits (220,000 to 350,000 kDa). Each monomer contains a heme prosthetic group at the catalytic center. CAT monomers from certain species (e.g., cow) also contain one tightly bound NADP per subunit. This NADP may serve to protect the enzyme from oxidation by its $H_2O_2$ substrate. The body's production of CAT is dependent upon the availability of iron.

Glutathione Peroxidases (GPXs)

Glutathione peroxidases (GPXs) are a large class of diverse enzymes which catalyze the reduction of hydrogen peroxide ($H_2O_2$), organic hydroperoxides and lipid hydroperoxides to the corresponding alcohol using glutathione (GSH; glutamyl-cysteinylglycine) as the electron donor (Ursini et al., 1995).

The GPX enzymes catalyze the reduction of $H_2O_2$ to water and organic peroxides (R—O—O—H) to the corresponding stable alcohols (R—O—H) using glutathione (GSH) as a source of reducing equivalents: $2\ GSH \rightarrow ROH+GSSG+H_2O$.

GPXs are important in helping to protect cells against oxidative damage, particularly lipid peroxidation. In mammals, the cytosolic (c) GPX family as well as a family of phospholipid hydroperoxide (PH) GPXs possess a selenocysteine residue at their active site. With the exception of phospholipid-hydroperoxide GPX, a monomer, all of the GPX enzymes are comprised of four identical subunits (monomer Mr 22-23 kDa). Each subunit contains a molecule of selenocysteine in the enzyme active site. The selenocysteine is thought to participate directly in electron donation to the peroxide substrate and to become oxidized in the process. The enzyme then uses glutathione as an electron donor to regenerate the reduced form of the selenocysteine. The GPX enzymes accept a wide variety of organic peroxides as substrates. The body's ability to produce GPX is in part dependent upon the adequate supply of selenium, of glutathione, a tripeptide that the body produces from the amino acids cysteine, glutamic acid, and glycine. Mammals contain plasma (p) GPXs, which are nonselenium containing enzymes in which cysteine replaces selenocysteine at their active site. However, with the exception of phospholipid hydroperoxide GPX and perhaps pl.cndot.GPX, the enzymes exhibit a strong preference for glutathione as a source of reducing equivalents.

Non-Enzymatic Antioxidants

Glutathione (GSH) and thioredoxin (Txn) serve as substrates for glutathione peroxidase (GPx), and peroxiredoxins (Prdx). GSH is highly abundant (at millimolar concentrations) cellular tripeptide L-γ-glutamyl-L-cysteinyl-glycine. Because of its high reactivity with free radicals, GSH is easily oxidized. The ratio of GSH to oxidized GSH (GSSG) has been used as a marker of cellular redox status. Thioredoxin (Txn) is located in the inner mitochondrial membrane and is involved in the reduction of hydrogen peroxide, lipid peroxide, and proteins with oxidatively modified sulfhydryl residues. (Jung, K. A. and Kwak, M.-K., "The Nrf2 system as a potential target for the development of indirect antioxidants," Molecules, 15: 7266-7291 (2010)).

Phase 2 Detoxifying Enymes

Phase 2 detoxifying enzymes, originally recognized as xenobiotic metabolizing enzymes, are also referred to as drug metabolizing enzymes (DMEs). Xenobiotics, which include various environmental chemicals, carcinogens, and drugs, undergo sequential two-step metabolism. Phase 1 enzymes initially catalyze the introduction of functional groups into hydrophobic organic molecules through the action of cytochrome P450 enzymes. Phase 2 enzymes are then responsible for the elimination of xenobiotics by forming conjugated metabolites using hydrophilic molecules such as GSH and glucuronic acid. (Jung, K. A. and Kwak, M.-K., "The Nrf2 system as a potential target for the development of indirect antioxidants," Molecules, 15: 7266-7291 (2010)).

Phase 2 reactions can be classified into four different categories that include: (1) a nucleophilic trapping reaction between an electrophilic substrate and GSH through glutathione transferase (GST); (2) a nucleophilic reaction between an epoxide and water via epoxide hydrolase; (3) a conjugation reaction between UDP-glucuronosyl-transferase (UGT) and sulfotransferase that converts lipophilic chemicals to water soluble glucuronide and sulfate conjugates to facilitate excretion through bile and urine, and (4) a reduction reaction, such as the obligatory two-electron reduction of quinones and quinonoids by NAD(P)H:quinone oxidoreductase 1 (NQO1). (Ma, Q. and He, X., "Molecular basis of electrophilic and oxidative defense: promises and perils of Nrf2," Pharmacological Reviews, 64: 1055-1081 (2012)).

Phase 2 enzymes can also be classified into four different categories: (i) classical conjugating enzymes, such as glutathione-S-transferases (GSTs) and UDP-glucuronosyl-transferases (UGTs); (ii) enzymes contributing to the biosynthesis and recycling of thiols such as γ-glutamate cysteine ligase (GCL), which is involved in the biosynthesis of GSH, GSH reductase, and Txn reductase; (iii) enzymes involved in the reduction of reactive intermediates, such as NAD(P)H: quinone oxidoreductases (NQOs) and epoxide hydrolase (EH); and (iv) stress-response proteins such as heme oxygenase-1 (HO-1) and ferritin. Due to their role in maintaining redox balance, thiol homeostasis, and excretion of reactive metabolites (e.g., peroxides, epoxides, aldehydes, quinones), phase 2 enzymes are now considered antioxidant enzymes. (Jung, K. A. and Kwak, M.-K., "The Nrf2 system as a potential target for the development of indirect antioxidants," Molecules, 15: 7266-7291 (2010)).

GSTs are ubiquitous, multifunctional enzymes that detoxify endogenous and exogenous electrophiles, including epoxides, aldehydes and peroxides. There are seven distinct classes of GSTs based on amino acid sequence similarities, physical structure of the genes and immunological cross reactivity: alpha (α), mu (μ), omega (ω), pi (π), sigma (σ), theta (θ), and zeta (ζ). UGTs catalyze the glucuronic acid conjugation reaction that mediates the major excretory pathway for pollutants and drugs, as well as endogenous compounds such as bilirubin, steroids, and hormones. A number of studies have confirmed the protective role of UGTs against environmental chemicals and carcinogens. NQO1 (also known as DT-diaphorase or quinone reductase type 1), a key enzyme belonging to the family of homodimeric flavoproteins, facilitates quinone excretion by catalyzing the reduction of quinones to hydroquinones through a single-step two-electron reduction reaction. Since the alternative one-electron reduction of quinone can form semihydroquinone, which is capable of generating ROS through redox-cycling, NQO1 functions to prevent oxidative DNA damage by environmental stressors. (Jung, K. A. and Kwak, M.-K., "The Nrf2 system as a potential target for the development of indirect antioxidants," Molecules, 15: 7266-7291 (2010)).

Nuclear Factor-Erythroid-2-Related Factor 2 (Nrf2) and Antioxidant Response Element (ARE) Signaling The antioxidant response element (ARE) is a cis-acting enhancer sequence containing enhancer regions E1 and E2 that mediate transcriptional activation of genes in cells exposed to oxidative stress including a broad spectrum of circumstances (such as an increased production of free radical species within the cell or by pro-oxidant xenobiotics) that are thiol reactive and mimic an oxidative insult. The genes regulated by the ARE encode proteins that help control the cellular redox status and defend the cell against oxidative damage. For example, proteins that are encoded by the ARE gene battery include, but are not limited to, enzymes associated with glutathione biosynthesis, redox proteins with active sulfhydryl moieties, and drug metabolizing enzymes. (Nguyen, T. et al., "Regulatory mechanisms controlling gene expression mediated by the antioxidant response element," Annu Rev. Pharmacol. Toxicol., 43: 233-260 (2003)).

Nuclear factor-erythroid-2-related factor 2 (Nrf2), a member of the NF-E2 family of the basic leucine zipper transcription factors, is essential for the coordinated induction of genes encoding many stress-responsive or cytoptotective enzymes and related proteins, such as NAD(P)H:quinone oxidoreductase-1 (NQO1), superoxide dismutase (SOD), glutathione 5-transferase (GST), glutathione peroxidase (GPx), heme oxygenase-1 (HO-1), glutamate cysteine ligase (GCL), catalase, and thioredoxin. In resting cells, Nrf2 resides in the cytoplasm by forming an inactive complex with the repressor Kelch-like ECH-associated protein 1 (Keap1), which is anchored to the actin cytoskeleton. Keap1 is a cysteine-rich homodimeric, multi-domain zinc metalloprotein. This tight interaction presents Nrf2 for ubiquinination followed by proteasomal degradation. Keap1 associates with Cullin 3 (Cu13) and Rbx1 to form a functional E3 ubiquitin ligase complex that targets multiple lysine residues located in the N-terminal Neh2 domain of Nrf2 for ubiquitination. Thus, Keap1 functions as a substrate adaptor protein for a Cul3-dependent E3 ubiquitin ligase complex and thereby regulates steady-state levels of Nrf2. Under oxidative or electrophilic stress, Nrf2 is stabilized and translocated to the nucleus, where it transactivates ARE-regulated genes. (Surh, Y.-J. et al., "Nrf2 as a master redox switch in turning on the cellular signaling involved in the induction of cytoprotective genes by some chemopreventive phytochemicals," Planta Med., 74: 1526-1539 (2008)).

It is generally believed that the mechanisms underlying nuclear translocation of Nrf2 and subsequent transactivation of ARE-regulated genes include (a) stabilization of cytoplasmic Nrf2 through blockade of its ubiquitination and proteasomal degradation by Keap1-Cul3 complex, and (b) dissociation of Nrf2 from Keap1 via phosphorylation of serine or threonine residues of Nrf2 by activation of protein kinases such as .mitogen-activated protein (MAP) kinases, phosphatidylinositol 3-kinase (PI3K)/Akt, protein kinase C(PKC), and casein kinase-2 (CK2). After migration to the nucleus, Nrf2 undergoes heterodimeric combinations with other transcription factors, such as small Maf protein and binds to the 5'-upstream cis-acting antioxidant regulatory sequence ARE or electrophile response elements (EpRE), located in the promoter region of genes encoding various antioxidant/detoxifying enzymes. (Surh, Y.-J. et al., "Nrf2 as a master redox switch in turning on the cellular signaling involved in the induction of cytoprotective genes by some chemopreventive phytochemicals," Planta Med., 74: 1526-1539 (2008)).

Antioxidant Compositions for Protection Against Oxidative Stress

The use of antioxidant containing dietary supplements for protection against the effects of oxidative stress and the progression of degenerative diseases and aging has been the subject of an increasing number of studies during the past four decades, see for example, Pauling L., N Engl J. Med., Vitamin C therapy of advanced cancer, Mar. 20, 1980; 302(12):694-5. Vitamins such as vitamin C and vitamin E, both of which are found in foods and available as supplements, help the body reduce effects of oxidative stress.

Non-enzymatic antioxidants can react with free radicals directly and become self-oxidized (therefore no longer available to quench free radicals); or one antioxidant may act as a reducing agent and another antioxidant oxidized in cyclical fashion (e.g., the interaction of ascorbic acid and alpha-tocopherol). Some non-enzymatic free radical scavengers have been used experimentally with varying results (e.g., mannitol, PBS, etc.); their clinical use is severely limited due to their toxicities. Some synthetic antioxidants, e.g., BHA (butylated hydroxy anisole), BHT (butylated hydroxy toluene) and NDGA (nordihydro guaiaretic acid), may cause allergic reactions and contribute to oncogenesis due to their strong toxicity in the body, and can be easily disrupted by heat due to temperature sensitivity.

A number of dietary phytochemicals that have the ability to activate Nrf2-ARE signaling have been described, including for example, sulforaphase [1-isothiocyanato-(4R,S)-(methylsulfinyl)butane], a representative isothiocyanate present in broccoli and other cruciferous vegetables, curcuminoids (diferuloylmethanes derived from the rhizomes of turmeric), epigallocatechin gallate (EGCG, the major catechin component of green tea), allyl sulfides (such as diallyl sulfide (DAS), diallyl disulfide (DADS) and diallyl trisulfide (DATS) derived from garlic oil), resveratrol (trans-3,5,4'-trihydroxystilbene, found in grapes and other plant species), vanilloids such as capsaicin (trans-8-methyl-N-vanillyl-6-nonenamide, the major pungent ingredient in hot chilli pepper *Capsicum annuum* L., Solanaceae) and (10)-shogaol (the pungent ingredient in ginger *Zingiber officianale* Roscoe, Zingiberaceae), and lycopene (found in tomato products). (Surh, Y.-J. et al., "Nrf2 as a master redox switch in turning on the cellular signaling involved in the induction of cytoprotective genes by some chemopreventive phytochemicals," Planta Med., 74: 1526-1539 (2008)).

Table 1 lists exemplary phytochemicals that can activate the Nrf2-ARE signaling system.

TABLE 1

Exemplary phytochemicals that activate Nrf2-ARE signaling

| Phytochemical | Structure |
| --- | --- |
| Sulforaphane | [structure] |
| Curcumin | [structure] Curcumin |
| Diallyl sulfide | [structure] |
| Diallyl trisulfide | [structure] |
| S-Allyl cysteine | [structure] |

TABLE 1-continued
Exemplary phytochemicals that activate Nrf2-ARE signaling
| Phytochemical | Structure |
| --- | --- |
| Capsaicin | 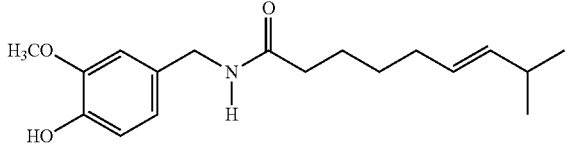 [SMILES: COc1cc(CNC(=O)CCCC/C=C/C(C)C)ccc1O] |
| 10-Shogaol | 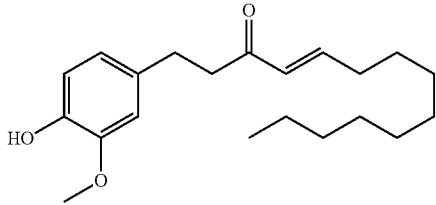 [SMILES: CCCCCCCCC/C=C/C(=O)CCc1ccc(O)c(OC)c1] |
| Piperine | 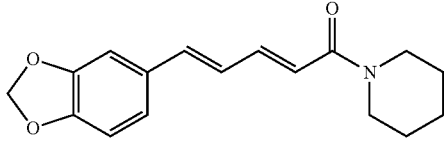 [SMILES: O=C(/C=C/C=C/c1ccc2c(c1)OCO2)N1CCCCC1] |
| Cinnamaldehyde | 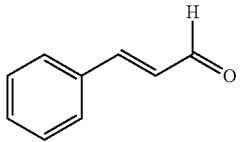 |
| Resveratrol | 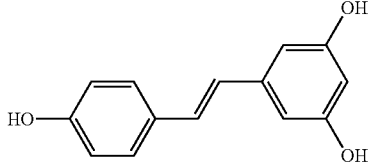 [SMILES: Oc1ccc(/C=C/c2cc(O)cc(O)c2)cc1] |
| Lycopene | 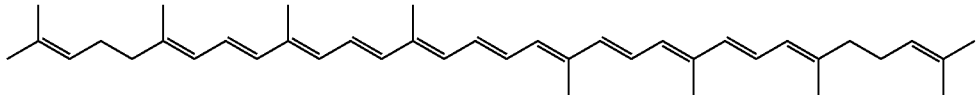 [SMILES: CC(C)=CCC/C(C)=C/C=C/C(C)=C/C=C/C(C)=C/C=C/C=C(C)/C=C/C=C(C)/C=C/C=C(\C)CCC=C(C)C] |
| Cafestol | 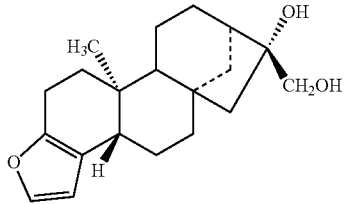 |
| Kahweol | 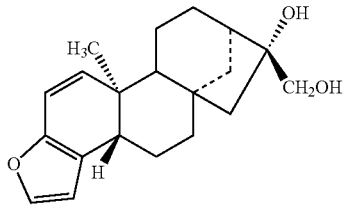 |

TABLE 1-continued

Exemplary phytochemicals that activate Nrf2-ARE signaling

| Phytochemical | Structure |
| --- | --- |
| Carnosol | 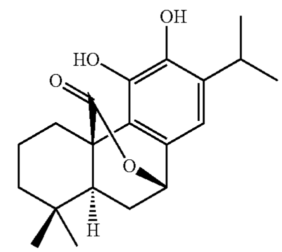 |
| Zerumbone | 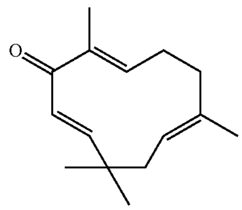 [SMILES: C/C1=C\CC(C)(C)/C=C/C(=O)/C(C)=C/CC1] |
| Xanthohumol | 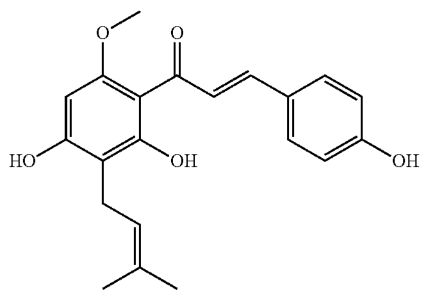 [SMILES: COc1cc(O)c(CC=C(C)C)c(O)c1C(=O)/C=C/c1ccc(O)cc1] |
| Isoliquiritigenin | 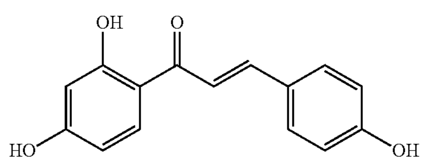 [SMILES: O=C(/C=C/c1ccc(O)cc1)c1ccc(O)cc1O] |
| Epigallocatechin-3-gallate | 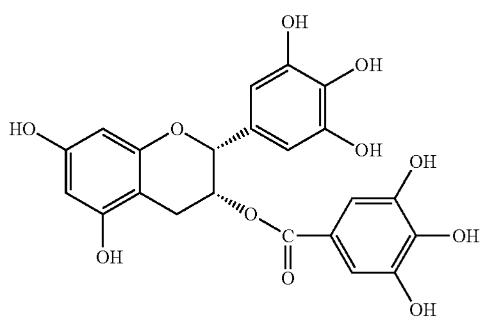 [SMILES: O=C(O[C@@H]1Cc2c(O)cc(O)cc2O[C@@H]1c1cc(O)c(O)c(O)c1)c1cc(O)c(O)c(O)c1] |
| Quercetin | 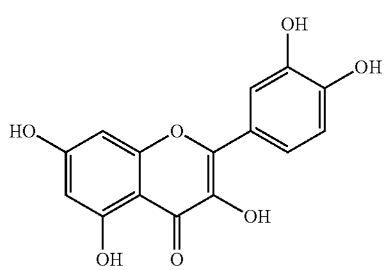 [SMILES: O=c1c(O)c(-c2ccc(O)c(O)c2)oc2cc(O)cc(O)c12] |

TABLE 1-continued

Exemplary phytochemicals that activate Nrf2-ARE signaling

| Phytochemical | Structure |
|---|---|
| Isoorientin | 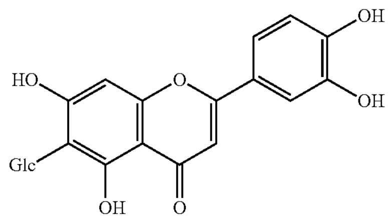 |
| Eupatilin | 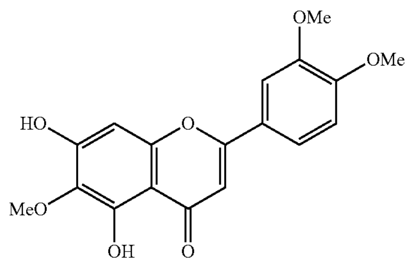 [SMILES: COc1ccc(-c2cc(=O)c3c(O)c(OC)c(O)cc3o2)cc1OC] |
| Brazilin | 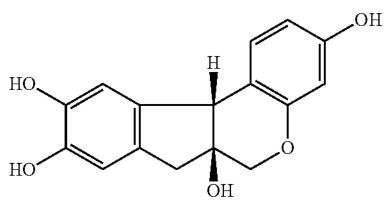 [SMILES: Oc1ccc2c(c1)OC[C@]1(O)Cc3cc(O)c(O)cc3[C@H]21] |
| Chlorophyllin | 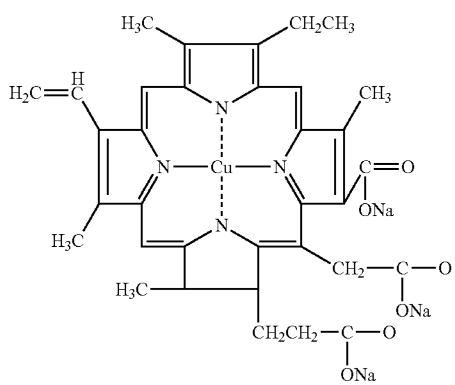 |
| 3-O-caffeol-1-methylquinic acid | 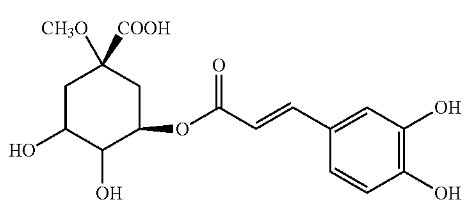 |

Although enzymatic antioxidants (e.g., SOD, CAT and GPX) are not consumed in the reactions with free radicals, they can be damaged under pathological conditions and consequently rendered non-functional, leaving the local cellular environment compromised and subject to free radical attack. The disadvantage of administering enzymatic antioxidants to humans however is (1) the possibility of allergic reactions (in the case of a bacterial or fungal derived enzyme) of varying degrees of severity; (2) the cost of harvesting these enzymes; (3) the limited quantities of enzymatic antioxidants that can be administered at a given time (theoretically to avoid side-effects such as serum sickness or other immune reaction to the recombinant protein); (4) they serve a singular purpose (i.e., they react with only one type of oxidant); and (5) they do not quench all radicals, which may be important for beneficial metabolic pathways, e.g., nitric oxide induced vasodilation and immune system support (see, e.g., Griscavage J M, Wilk S, Ignarro U J., Proc Natl Acad Sci USA, Inhibitors of the proteasome pathway interfere with induction of nitric oxide synthase in macrophages by blocking activation of transcription factor NF-kappa B., Apr. 16, 1996; 93(8):3308-12.

The efficacy of direct oral administration of SOD, CAT, or GPX has been limited by the sensitivity of these enzymes to the milieu of the digestive system and/or lack of bioavailability. For example, research has indicated that the digestive system destroyed SOD, and that neither CAT nor GPX was absorbed via the digestive tract.

Since administration by direct ingestion of antioxidants showed disappointing results, efforts have been directed to provide the body with the so-called "building blocks" to increase the activities of SOD, CAT, and GPX in the body. Accordingly, supplements have been formulated to increase levels of the body's zinc, copper, and manganese, to assist the body's production of SOD. Similarly, iron, selenium, and glutathione related supplements have been developed to increase CAT and GPX. These compounds have toxic effects in large quantities.

A natural dietary supplement that induces production of SOD, CAT and GPX should ideally reduce the concentration of free radicals and ROS in the body and result in decreased rates of lipid peroxidation. However, it has been observed that some formulations of dietary supplements that induce antioxidant production may contemporaneously cause an increase in the concentration of ROS leading to increased rates of lipid peroxidation. In other words, while some supplements may achieve an increase in the body's production of SOD, CAT, and GPX but they result in an overall net increase in oxidative stress as measured by an increase in the ROS levels. Accordingly, choosing an active agent based simply on its ability to cause the induction of antioxidant production, per se, may not be adequate to achieve the overall desired goal of alleviating oxidative stress.

Plant extracts, which are typically the ingredients of natural dietary supplements, may also have undesirable side-effects, which also need to be properly balanced in an overall formulation. For example, research has indicated that an ethanol extract of *Bacopa monnieri* produces toxicity in the brine shrimp lethality assay at about 300 mg/L (D'Souza et al. Phytotherapy Res. 2002, vol 16, 197-8) and enhances thyroid function, which may be an undesirable side effect (Kar et al. J. Ethnopharmacol. 2002, vol 81, 281-5).

There remains a need to formulate improved compositions that increase antioxidant levels in a mammal that can be more effective, have fewer side-effects and a lowered toxicity without causing an overall net increase in oxidative stress. The foregoing problems, among others, have been resolved by the described invention, which provides compositions capable of treating oxidative stress. The compositions increase antioxidant potential in the subject by increasing the activity of at least one antioxidant enzyme, e.g., SOD, CAT, and GPX, thereby decreasing the tissue level of pathologic free radical species, and provides for an overall net decrease in oxidative stress with minimal undesirable side-effects. The composition provides fewer side effects than may be associated with each of the individual active agents in the composition.

SUMMARY OF THE INVENTION

According to one aspect, the described invention provides a composition for treating oxidative stress in a subject in need thereof, the composition comprising at least two botanical extracts, each botanical extract containing a therapeutic amount of a botanical active ingredient, wherein the botanical extract is selected from the group consisting of: (a) a *Bacopa monnieri* extract comprising at least one *Bacopa monnieri* active ingredient; (b) a *Silybum marianum* (milk thistle) extract comprising at least one *Silybum marianum* active ingredient; (c) a *Withania somnifera* (ashwagandha) extract comprising at least one *Withania somnifera* active ingredient; (d) a *Camellia sinensis* (green tea) extract comprising at least one *Camellia sinensis* active ingredient; and (e) a *Curcuma longa* (turmeric) extract comprising at least one *Curcuma longa* active ingredient; wherein the therapeutic amount of the botanical active ingredient is effective to: (i) increase a level of enzyme activity of at least one antioxidant enzyme selected from the group consisting of a superoxide dismutase (SOD), a catalase (CAT), a glutathione peroxidase (GPX); (ii) decrease a level of reactive oxygen species (ROS); (iii) synergistically increase expression of a phase 2 gene by activating a Nuclear factor-erythroid-2-related factor 2 (Nrf2) transcription factor-dependent transcription activity of an antioxidant response element (ARE); or a combination thereof, without significant side effects thereby treating the oxidative stress. According to one embodiment, the phase 2 gene is selected from the group consisting of a NAD(P)H: quinone oxidoreductase-1 (NQO1) gene, a superoxide dismutase (SOD) gene, a glutathione S-transferase (GST) gene, a glutathione peroxidase (GPx) gene, a heme oxygenase-1 (HO-1) gene, a glutamate cysteine ligase (GCL) gene, a catalase gene, a thioredoxin gene, or a combination thereof. According to another embodiment, the increase in expression of the phase 2 gene is an increase in promoter activity of the phase 2 gene, an increase in a level of messenger RNA (mRNA) of the phase 2 gene, an increase in a level of phase 2 protein expressed from the phase 2 gene, or a combination thereof. According to another embodiment, the Nuclear factor-erythroid-2-related factor 2 (Nrf2) transcription factor activating potential is quantified by a process comprising: (1) contacting a first sample of AREc32 cells with the botanical extract and a second sample of AREc32 cells with a buffer control; (2) incubating the first sample of AREc32 cells with the botanical extract and the second sample of AREc32 cells with the buffer control for at least 18 hours at 37° C.; (3) washing the first and second samples of AREc32 cells from step (2); (4) lysing the first and second samples of washed AREc32 cells from step (3); (5) incubating the lysate from the first and second samples of lysed AREc32 cells from step (4) with D-luciferin; and (6) measuring luminescence of the first and second samples of incubated AREc32 cells from step (5). According to another embodiment, the Nrf2 activating potential of each botanical extract is standardized against Nuclear factor-erythroid-2-related factor 2 (Nrf2) transcription factor activating potential of a substantially pure active ingredient. According to another embodiment, the composition is formulated as an oral dosage form. According to another embodiment, the oral dosage form is selected from the group consisting of: a tablet; capsule; and caplet. According to another embodiment, the composition further comprises one or more excipients selected from the group consisting of calcium carbonate; croscarmellose sodium; dicalcium phosphate; magnesium stearate; microcrystalline cellulose; modified cellulose; silica; and stearic acid. According to another embodiment, the *Bacopa monnieri* active ingredient is a bacoside selected from the group consisting of bacoside A, bacoside B, bacoposide III, bacopaside IV, bacopaside V, or a combination thereof. According to another embodiment, the *Silybum marianum* active ingredient is silymarin. According to another embodiment, the *Withania somnifera* active ingredient is withaferin A. According to another embodiment, the *Camellia sinensis* active ingredient is epigallocatechin gallate (EGCG). According to another embodiment, the *Cur-*

*cuma longa* active ingredient is curcumin. According to another embodiment, the composition further comprises at least one botanical extract containing a therapeutic amount of a botanical active ingredient, wherein the botanical extract is selected from the group consisting of: (f) a *Centella asiatica* (Gotu kola) extract comprising at least one *Centella asiatica* active ingredient; (g) an *Aloe vera* extract comprising at least one *Aloe vera* active ingredient; (h) a *Gingko biloba* extract comprising at least one *Gingko biloba* active ingredient; and (i) N-acetyl cysteine. According to another embodiment, at least one of the botanical extracts is in the form of a powder, a liquid solution, a suspension, a dispersion, an emulsion, a tablet, a pill, or a capsule.

According to another aspect, the described invention provides a method of quantifying a Nuclear factor-erythroid-2-related factor 2 (Nrf2) transcription factor activating potential of a botanical extract comprising a botanical active ingredient, comprising: (1) contacting a first sample of AREc32 cells with the botanical extract and a second sample of AREc32 cells with a buffer control; (2) incubating the first sample of AREc32 cells with the botanical extract and the second sample of AREc32 cells with the buffer control for at least 18 hours at 37° C.; (3) washing the first and second samples of AREc32 cells from step (2); (4) lysing the first and second samples of washed AREc32 cells from step (3); (5) incubating the lysate from the first and second samples of lysed AREc32 cells from step (4) with D-luciferin; and (6) measuring luminescence of the first and second samples of incubated AREc32 cells from step (5). According to one embodiment, the botanical extract is selected from the group consisting of: (a) a *Bacopa monnieri* extract comprising at least one *Bacopa monnieri* active ingredient; (b) a *Silybum marianum* (milk thistle) extract comprising at least one *Silybum marianum* active ingredient; (c) a *Withania somnifera* (ashwagandha) extract comprising at least one *Withania somnifera* active ingredient; (d) a *Camellia sinensis* (green tea) extract comprising at least one *Camellia sinensis* active ingredient; (e) a *Curcuma longa* (turmeric) extract comprising at least one *Curcuma longa* active ingredient; (f) a *Centella asiatica* (Gotu kola) extract comprising at least one *Centella asiatica* active ingredient; (g) an *Aloe vera* extract comprising at least one *Aloe vera* active ingredient; (h) a *Gingko biloba* extract comprising at least one *Gingko biloba* active ingredient; or a combination thereof. According to another embodiment, the Nrf2 activating potential of the botanical extract is standardized against Nuclear factor-erythroid-2-related factor 2 (Nrf2) transcription factor activating potential of a substantially pure active ingredient. According to another embodiment, the *Bacopa monnieri* active ingredient is a bacoside selected from the group consisting of bacoside A, bacoside B, bacoposide III, bacopaside IV, bacopaside V, or a combination thereof. According to another embodiment, the *Silybum marianum* active ingredient is silymarin. According to another embodiment, the *Withania somnifera* active ingredient is withaferin A. According to another embodiment, the *Camellia sinensis* active ingredient is epigallocatechin gallate (EGCG). According to another embodiment, the *Curcuma longa* active ingredient is curcumin.

BRIEF DESCRIPTION OF THE DRAWINGS

FIG. 29A shows the HO-1 driven expression of the reporter gene at three concentrations of a 95% ethanol extract of Protandim®. The abscissa reflects the amount of Protandim® extracted per ml of culture medium, and the values are in the range of expected values for humans dosed orally with Protandim® at one 675 mg caplet per day. The presence of synergy is suggested by simple inspection of the plot, as evidenced by the upward curvature, and a greater-than-linear response to increases in concentration.

DETAILED DESCRIPTION OF THE INVENTION

Glossary

Figure 1:
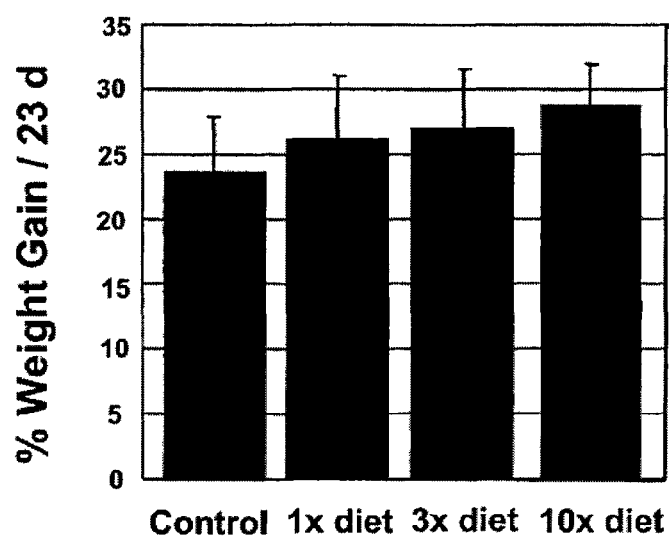
FIG. 1 is a graph illustrating effect of Protandim®-I dietary supplementation on percent weight gain of mice after 23 days.

The terms "active constituent", "active ingredient" or "active agent" are used herein to mean the chemical constituent in a botanical raw material that is responsible for the intended therapeutic effect.

The term "additive effect", as used herein, refers to a combined effect of two chemicals that is equal to the sum of the effect of each agent given alone.

The term "administering" as used herein includes in vivo administration, as well as administration directly to tissue ex vivo. Generally, compositions may be administered either orally, or parenterally.

The term "anti-oxidant agent" as used herein refers to a substance that inhibits oxidation or reactions promoted by oxygen or peroxides. Non-limiting examples of anti-oxidants that are usable in the context of the described invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the tradename Trolox®), gallic acid and its alkyl esters (for example, propyl gallate), uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

The term "antioxidant activity" as used herein refers to ability of a substance to reduce oxidative stress. Without being limited by theory, the mechanism of reducing oxidative stress can be by either decreasing the level of reactive oxygen species (ROS), or decreasing the enzyme activity of at least one antioxidant enzyme for example a superoxide dismutase (SOD), a catalase (CAT), a glutathione peroxidase (GPX), or a combination thereof.

The term "binder" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2% to about 20% by weight of the composition, more preferably from about 3% to about 10% by weight, even more preferably from about 3% to about 6% by weight.

The term "botanical composition" as used herein refers to a material formed of at least two or more botanical extracts.

The terms "botanical extract", and "herbal extract" are used interchangeably to refer to a product prepared by separating, by chemical or physical process, medicinally active portions of a plan from the inactive or inert components. According to one embodiment, the botanical extracts prepared according to the present invention are obtained by means of a solvent, optionally under pressure and/or heat.

The term "botanical ingredient" refers to a component that originates from a botanical raw material.

The term "botanical product" refers to a finished, labeled product that contains vegetable matter, which may include plant materials, algae, macroscopic fungi, or combinations thereof. Depending in part on its intended use, a botanical product may be a food, drug, medical device or cosmetic.

The term "botanical raw material" as used herein refers to a fresh or processed (e.g. cleaned, frozen, dried, sliced, dissolved, or liquefied) part of a single species of plant or a fresh or processed alga or macroscopic fungus.

The terms "buccal", "buccally" or "buccal administration" are used interchangeably to refer to administration of a medicinal formulation between the cheek and gums.

The terms "buffer" or "buffering agent" are used interchangeably to mean an excipient that stabilizes pH of a composition, such as a pharmaceutical composition. Exemplary buffers include but are not limited to borate buffers, histidine buffers, citrate buffers, succinate buffers, acetate buffers, tartrate buffers, phosphate buffers, Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "capsule" refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1% to about 5% by weight of the composition, preferably from about 0.1% to about 1%.

The term "composition" as used herein refers to a material formed of two or more substances.

The term "condition", as used herein, refers to a variety of health states and is meant to include disorders or diseases caused by any underlying mechanism or disorder, injury, and the promotion of healthy tissues and organs.

The terms "dietary supplement" and "nutritional supplement" are used interchangeably herein to mean (1) a product intended to supplement the diet that bears or contains one or more of the following dietary ingredients: [A] a vitamin, [B] a mineral, [C] an herb or other botanical, [D] an amino acid, [E] a dietary substance for use by man to supplement the diet by increasing the total dietary intake; or (F) a concentrate, metabolite, constituent, extract, or combination of any ingredient described in clause (A), (B), (C), (D), or (E); and (2) a product that (A)(i) is intended for ingestion; (B) is not represented for use as a conventional food or as a sole item of a meal or the diet; and (C) is labeled as a dietary supplement. For purposes of the present invention, this definition includes tobacco.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "diluent" refers to substances that usually make up the major portion of the composition or dosage form. Exemplary diluents include, but are not limited to, sugars such as lactose, sucrose, mannitol and sorbitol; starches derived from wheat, corn, rice and potato; and celluloses such as microcrystalline cellulose. The amount of diluent in the composition can range from about 10% to about 90% by weight of the total composition, preferably from about 25% to about 75%, more preferably from about 30% to about 60% by weight, even more preferably from about 12% to about 60%.

The term "disease" or "disorder", as used herein, refers to an impairment of health or a condition of abnormal functioning.

The term "dispersion", as used herein, refers to a two-phase system, in which one phase is distributed as particles or droplets in the second, or continuous phase. In these systems, the dispersed phase frequently is referred to as the discontinuous or internal phase, and the continuous phase is called the external phase or dispersion medium. For example, in course dispersions, the particle size is 0.5 µm. In colloidal dispersions, size of the dispersed particle is in the range of approximately 1 nm to 0.5 µm. Molecular dispersion is a dispersion, in which the dispersed phase consists of individual molecules; if the molecules are less than colloidal size, the result is a true solution.

The term "effective amount" refers to the amount necessary or sufficient to realize a desired biologic effect.

The term "emulsion" as used herein refers to a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "essentially free" means less than about 10% of the amount found in unprocessed material.

The term "extracting" as used herein refers to the process of drawing out, withdrawing, distilling or otherwise separating one substance from another by a chemical or physical process.

The term "formulation" as used herein refers to a mixture prepared according to a formula, recipe or procedure. As used herein, the terms "formulation" and "composition" are used interchangeably.

The term "fractionate" and its various grammatical forms as used herein refers to separating or dividing into component parts, fragments, or divisions.

The term "hydrogel" as used herein refers to a substance resulting in a solid, semisolid, pseudoplastic, or plastic structure containing a necessary aqueous component to produce a gelatinous or jelly-like mass.

The term "inhibiting" as used herein refers to reducing or modulating the chemical or biological activity of a substance or compound.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses. The classic signs of inflammation are pain (dolor), heat (calor), redness (rubor), swelling (tumor), and loss of function (functio laesa). Histologically, inflammation involves a complex series of events, including dilatation of arterioles, capillaries, and venules, with increased permeability and blood flow; exudation of fluids, including plasma proteins; and leukocytic migration into the inflammatory focus. The term "acute inflammation" as used herein, refers to inflammation, usually of sudden onset, characterized by the classical signs, with predominance of the vascular and exudative processes. The term "chronic inflammation" as used herein refers to inflammation of slow progress and marked chiefly by the formation of new connective tissue; it may be a continuation of an acute form or a prolonged low-grade form, and usually causes permanent tissue damage.

The term "injection", as used herein, refers to introduction into subcutaneous tissue, or muscular tissue, a vein, an artery, or other canals or cavities in the body by force.

The term "isolated molecule" as used herein refers to a molecule that is substantially free of other substances with which it is ordinarily found in nature or in vivo systems to an extent practical and appropriate for its intended use.

The term "lubricant" refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2% to about 5% by weight of the composition, preferably from about 0.5% to about 2%, more preferably from about 0.3% to about 1.5% by weight.

The term "modify" as used herein means to change, vary, adjust, temper, alter, affect or regulate to a certain measure or proportion in one or more particulars.

The term "modifying agent" as used herein refers to a substance, composition, extract, botanical ingredient, botanical extract, botanical constituent, therapeutic component, active constituent, therapeutic agent, drug, metabolite, active agent, protein, non-therapeutic component, non-active constituent, non-therapeutic agent, or non-active agent that reduces, lessens in degree or extent, or moderates the form, symptoms, signs, qualities, character or properties of a condition, state, disorder, disease, symptom or syndrome.

The term "modulate" as used herein means to regulate, alter, adapt, or adjust to a certain measure or proportion.

The term "Nuclear factor-erythroid-2-related factor 2 (Nrf2) transcription factor activating potential" as used herein refers to the extent of turning on or increasing Nrf2-dependent transcription activity of an antioxidant response element (ARE).

The term "non-oral administration" represents any method of administration in which a composition is not provided in a solid or liquid oral dosage form, wherein such solid or liquid oral dosage form is traditionally intended to substantially release and or deliver the drug in the gastrointestinal tract beyond the mouth and/or buccal cavity.

As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually).

The term "oxidative stress" as used herein refers to a redox imbalance within the cell usually due to increased reactive oxygen species (ROS) and decreased antioxidants.

The term "parenteral" as used herein refers to introduction into the body by way of an injection (i.e., administration by injection) outside the gastrointestinal tract, including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The terms "particles" or "microparticles", as used herein, refer to extremely small constituents, e.g., nanoparticles or microparticles) that may contain in whole or in part at least one active constituent or botanical ingredient or botanical extract as described herein.

The term "pharmaceutically acceptable carrier" as used herein refers to one or more compatible solid or liquid filler, diluents or encapsulating substances which are suitable for administration to a human or other vertebrate animal. The term "carrier" as used herein refers to an organic or inorganic ingredient, natural or synthetic, with which the active ingredient is combined to facilitate the application that does not cause significant irritation to an organism and does not abrogate the biological activity and properties of the active compound of the composition of the described invention. The components of the pharmaceutical compositions also are capable of being commingled in a manner such that there is no interaction which would substantially impair the desired pharmaceutical efficiency. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "pharmaceutical composition" is used herein to refer to a composition that is employed to prevent, reduce in intensity, cure or otherwise treat a target condition or disease.

The term "pharmacologic effect", as used herein, refers to a result or consequence of exposure to an active ingredient.

The term "powder" as used herein refers to a solid substance reduced a state of fine, loose particles by crushing, grinding, disintegration, etc.

The phrase "recommended daily dose" as used herein refers to the dietary intake level that is sufficient to meet the nutrient requirement of nearly all (97% to 98%) healthy individuals in a particular life stage and gender group.

The terms "rectal" or "rectally" are used interchangeably to refer to introduction into the body through the rectum where absorption occurs through the walls of the rectum.

The term "reduce" or "reducing" as used herein refers to a diminution, a decrease, an attenuation, limitation or abatement of the degree, intensity, extent, size, amount, density, number or occurrence of disorder in individuals at risk of developing the disorder.

The term "side effect" as used herein refers to toxicity in the combination relative to the toxicity of each active agent when administered alone.

The terms "soluble" and "solubility" refer to the property of being susceptible to being dissolved in a specified fluid (solvent). The term "insoluble," as used herein refers to the property of a material that has minimal or limited solubility in a specified solvent.

The terms "stabilizing agent" and "stabilizer" are used interchangeably to mean a chemical or a compound that is added to a solution, mixture, suspension, or composition to maintain it in a stable or unchanging state.

The term "standardize" as used herein refers to the act of testing or comparing with a well-accepted exemplary measure.

The term "sublingual" as used herein refers to administration of a medicinal formulation under the tongue such that the active ingredient(s) can diffuse into the blood through the tissues under the tongue.

The terms "subject" or "individual" or "patient" are used interchangeably to refer to a member of an animal species of mammalian origin, including humans.

The term "subject in need thereof" as used herein refers to a subject showing signs and symptoms of or susceptible to oxidative stress.

The term "substantially pure", as used herein, refers to a condition of an agent such that it has been substantially separated from the substances with which it may be associated in living systems or during synthesis. According to some embodiments, a substantially pure therapeutic agent is at least 70% pure, at least 75% pure, at least 80% pure, at least 85% pure, at least 90% pure, at least 95% pure, at least 96% pure, at least 97% pure, at least 98% pure, or at least 99% pure.

The term "suspension" as used herein refers to a state in which particles of a substance are mixed but are undissolved.

The term "sustained release" (also referred to as "extended release") as used herein refers to a drug formulation that provides for gradual release of a drug over an extended period of time, and that preferably, although not necessarily, results in substantially constant blood levels of a drug over an extended time period.

The terms "sweetening agent" or "sweetener" as used herein refer to a substance used to sweeten food or drink other than sugar, for example saccharin sodium, dipotassium glycyrrhizate, aspartame and the like.

The term "syndrome," as used herein, refers to a pattern of symptoms indicative of some disease or condition.

The term "synergistic effect", as used herein, refers to a combined effect of two chemicals, which is greater than the sum of the effects of each agent given alone.

The phrase "systemic administration", as used herein, refers to administration of an agent to have a pharmacologic effect on the entire body. Systemic administration includes enteral administration (e.g. oral) through the gastrointestinal tract and parenteral administration (e.g. intravenous, intramuscular, etc.) outside the gastrointestinal tract.

The term "tablet" refers to a compressed or molded solid dosage form containing the active ingredients with suitable diluents. The tablet can be prepared by compression of mixtures or granulations obtained by wet granulation, dry granulation or by compaction.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The terms "therapeutic amount", "therapeutically effective amount" or an "amount effective" of one or more active agent(s) as used herein refer to an amount that is sufficient to provide the intended benefit of treatment. Dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. It is preferred generally that a maximum dose be used, that is, the highest safe dose according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein.

The term "thiobarbituric acid reactive (TBAR)" as used herein refers to a chemical species used as a measure of lipid peroxidation that is directly proportional to the level of free radical including ROS in a sample. An antioxidant agent capable of reducing the concentration of ROS has the effect of reducing TBARs.

The term "topical" refers to administration of a composition at, or immediately beneath, the point of application. The phrase "topically applying" describes application onto one or more surfaces(s) including epithelial surfaces. Topical administration, in contrast to transdermal administration, generally provides a local rather than a systemic effect.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

COMPOSITIONS OF THE INVENTION

According to one aspect, the described invention provides a composition for treating oxidative stress in a subject in need thereof, the composition comprising at least two botanical extracts, each botanical extract containing a therapeutic amount of a botanical active ingredient, wherein the botanical extract is selected from the group consisting of:
(a) a *Bacopa monnieri* extract comprising at least one *Bacopa monnieri* active ingredient;
(b) a *Silybum marianum* (milk thistle) extract comprising at least one *Silybum marianum* active ingredient;
(c) a *Withania somnifera* (ashwagandha) extract comprising at least one *Withania somnifera* active ingredient;

(d) a *Camellia sinensis* (green tea) extract comprising at least one *Camellia sinensis* active ingredient;

(e) a *Curcuma longa* (turmeric) extract comprising at least one *Curcuma longa* active ingredient;

wherein the therapeutic amount of the botanical active ingredient is effective to:
(i) increase a level of enzyme activity of at least one antioxidant enzyme selected from the group consisting of a superoxide dismutase (SOD), a catalase (CAT), a glutathione peroxidase (GPX);
(ii) decrease a level of reactive oxygen species (ROS);
(iii) synergistically increase expression of a phase 2 gene by activating a Nuclear factor-erythroid-2-related factor 2 (Nrf2) transcription factor-dependent transcription activity of an antioxidant response element (ARE);
or a combination thereof,
without significant side effects thereby treating the oxidative stress.

According to one embodiment, the composition further comprises at least one botanical extract containing a therapeutic amount of a botanical active ingredient, wherein the botanical extract is selected from the group consisting of:

(f) a *Centella asiatica* (Gotu kola) extract comprising at least one *Centella asiatica* active ingredient;

(g) an *Aloe vera* extract consisting comprising at least one *Aloe vera* active ingredient;

(h) a *Gingko biloba* extract comprising at least one *Gingko biloba* active ingredient; and (i) N-acetyl cysteine.

According to one embodiment, the level of reactive oxygen species (ROS) corresponds to a level of lipid peroxidation as measured by a plasma concentration level of a thiobarbituric acid reactive (TBAR) chemical species.

According to some embodiments, the phase 2 gene is selected from the group consisting of a NAD(P)H:quinone oxidoreductase-1 (NQO1) gene, a superoxide dismutase (SOD) gene, a glutathione S-transferase (GST) gene, a glutathione peroxidase (GPx) gene, a heme oxygenase-1 (HO-1) gene, a glutamate cysteine ligase (GCL) gene, a catalase gene, a thioredoxin gene, or a combination thereof. According to one embodiment, the phase 2 gene is a NAD(P)H:quinone oxidoreductase-1 (NQO1) gene. According to one embodiment, the phase 2 gene is a superoxide dismutase (SOD) gene. According to one embodiment, the phase 2 gene is a glutathione S-transferase (GST) gene. According to one embodiment, the phase 2 gene is a glutathione peroxidase (GPx) gene. According to one embodiment, the phase 2 gene is a heme oxygenase-1 (HO-1) gene. According to one embodiment, the phase 2 gene is a glutamate cysteine ligase (GCL) gene. According to one embodiment, the phase 2 gene is a catalase gene. According to one embodiment, the phase 2 gene is a thioredoxin gene.

According to some embodiments, the increase in expression of the phase 2 gene is an increase in promoter activity of the phase 2 gene, an increase in a level of messenger RNA (mRNA) of the phase 2 gene, an increase in a level of phase 2 protein expressed from the phase 2 gene, or a combination thereof. According to one embodiment, the increase in expression of the phase 2 gene is an increase in promoter activity of the phase 2 gene. According to another embodiment, the increase in expression of the phase 2 gene is an increase in a level of messenger RNA (mRNA) of the phase 2 gene. According to another embodiment, the increase in expression of the phase 2 gene is an increase in a level of phase 2 protein expressed from the phase 2 gene.

According to another embodiment, the botanical active ingredient of the botanical extract has a Nuclear factor-erythroid-2-related factor 2 (Nrf2) transcription factor-activating potential quantified by a process comprising:
(1) contacting a first sample of AREc32 cells with the botanical extract and a second sample of AREc32 cells with a buffer control;
(2) incubating the first sample of AREc32 cells with the botanical extract and the second sample of AREc32 cells with the buffer control for at least 18 hours at 37° C.;
(3) washing the first and second samples of AREc32 cells from step (2);
(4) lysing the first and second samples of washed AREc32 cells from step (3);
(5) incubating the lysate from the first and second samples of lysed AREc32 cells from step (4) with D-luciferin; and
(6) measuring luminescence of the first and second samples of incubated AREc32 cells from step (5).

According to another embodiment, the *Bacopa monnieri* active ingredient of the *Bacopa monnieri* extract has a Nuclear factor-erythroid-2-related factor 2 (Nrf2) transcription factor-activating potential. According to another embodiment, the *Silybum marianum* active ingredient of the *Silybum marianum* extract has a Nuclear factor-erythroid-2-related factor 2 (Nrf2) transcription factor-activating potential. According to another embodiment, the *Withania somnifera* active ingredient of the *Withania somnifera* extract has a Nuclear factor-erythroid-2-related factor 2 (Nrf2) transcription factor-activating potential. According to another embodiment, the *Camellia sinensis* active ingredient of the *Camellia sinensis* extract has a Nuclear factor-erythroid-2-related factor 2 (Nrf2) transcription factor-activating potential. According to another embodiment, the *Curcuma longa* active ingredient of the *Curcuma longa* extract has a Nuclear factor-erythroid-2-related factor 2 (Nrf2) transcription factor-activating potential.

According to another embodiment, the botanical active ingredient has at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 90 fold, at least 95 fold, at least 100 fold, at least 110 fold, at least 120 fold, at least 130 fold, at least 140 fold at least 150 fold, or at least 200 fold Nuclear factor-erythroid-2-related factor 2 (Nrf2) transcription factor-activating potential as compared to an untreated control.

According to some embodiments, the botanical extract is in a form of a powder, a liquid solution, a suspension, a dispersion, an emulsion, a tablet, a pill, or a capsule. According to one embodiment, the botanical extract is in a form of a powder. According to another embodiment, the botanical extract is in a form of a liquid solution. According to another embodiment, the botanical extract is in a form of a suspension. According to another embodiment, the botanical extract is in a form of a dispersion. According to another embodiment, the botanical extract is in a form of an emulsion. According to another embodiment, the botanical extract is in a form of a tablet. According to another embodiment, the botanical extract is in a form of a pill. According to another embodiment, the botanical extract is in a form of a capsule.

According to some embodiments, the botanical extract is a root extract, a leaf extract, a flower extract, a bark extract, a fruit extract, or a seed extract. According to one embodiment, the botanical extract is a root extract. According to another embodiment, the botanical extract is a leaf extract. According to another embodiment, the botanical extract is a flower extract. According to another embodiment, the botanical extract is a bark extract. According to another embodiment, the botanical extract is a fruit extract. According to another embodiment, the botanical extract is a seed extract.

Bacopa monnieri

Bacopa monnieri (common names: water hyssop and Brahmi) is a creeping perennial that thrives in warmer temperate climates. The genus Bacopa includes over 100 species of aquatic herbs distributed throughout the warmer regions of the world. The plant is a profusely branched herb, rooting at the nodes and forming dense mats. B. monnieri extract (Bacopin®) is a commercially available extract prepared from the leaves of the B. monnieri plant (Sabinsa Corporation, Piscataway, N.J., USA) standardized for a minimum of 20% bacosides A & B, the active ingredients beneficial in the support of cognitive functions. Other extracts of the B. monnieri plant standardized for greater minimum levels of bacosides A & B (e.g., 30%, 40%, 50%, etc.) are useful in the compositions of the present invention and can be prepared by extraction techniques known in the art. The pharmacological effects of B. monnieri preparations/extracts also include anti-oxidant, anti-inflammatory, cardiotonic and anticancer effects. Extract of B. monnieri is commercially available, e.g., Viable Herbal Solutions (Morrisville, Pa., USA). About 0.001 mg to 1000 g of Bacopa monnieri extract is considered safe; enhanced cytotoxicity in cultured cells (100 mg/kg) and anticancer activity (at 200 mg/kg) and thyroid function have been reported (D'Souza et al., Phytotherapy Res. 2002, vol 16, 197-8; Kar et al. J. Ethnopharmacol. 2002, vol 81, 281-5).

The described invention provides compositions for increasing the levels of antioxidants, via alteration of the activity level of SOD, CAT, and GPX enzymes in the body. According to one embodiment, the composition comprises a mixture of botanical extracts of Bacopa monnieri (B. monnieri or Bacopa sp.), which contains a high percentage of the active chemicals bacosides A & B. Ingestion of Bacopa induces SOD, CAT, and GPX and provides the beneficial activities thereof, with pronounced results in the brain. Studies have indicated that the bacosides also increase protein and serotonin levels, while decreasing norepinephrine concentration in the hippocampus, hypothalamus, and cerebral cortex. Bacopa thus can reduce the neurodegeneration in the brain that is caused by oxidative stress related to the accumulation of neurotoxic free radicals in the brain. Accordingly, it may be used to alleviate symptoms of neurodegenerative disorders, such as memory loss, Alzheimer's disease, and Parkinson's disease, and even aging.

According to one embodiment, the therapeutic amount of the Bacopa monnieri extract is from about 10 mg to about 4,000 mg for daily administration. According to another embodiment, the therapeutic amount of the Bacopa monnieri extract is from about 50 mg to about 3,000 mg for daily administration. According to another embodiment, the therapeutic amount of the Bacopa monnieri extract is from about 100 mg to about 2,000 mg for daily administration. According to some embodiments, the therapeutic amount of the Bacopa monnieri extract is at least about 4,000 mg, at least about 3,500 mg, at least about 3,000 mg, at least about 2,500 mg, at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 90 mg, at least about 80 mg, at least about 70 mg, at least about 60 mg, at least about 50 mg, at least about 40 mg, at least about 30 mg, at least about 20 mg, or at least about 10 mg, for daily administration.

According to another embodiment, the Bacopa monnieri extract is Bacopin®. According to another embodiment, the Bacopa monnieri extract comprises at least about 20% Bacopa monnieri active ingredient. According to another embodiment, the Bacopa monnieri extract comprises at least about 25% Bacopa monnieri active ingredient. According to another embodiment, the Bacopa monnieri extract comprises at least about 30% Bacopa monnieri active ingredient. According to another embodiment, the Bacopa monnieri extract comprises at least about 35% Bacopa monnieri active ingredient. According to another embodiment, the Bacopa monnieri extract comprises at least about 40% Bacopa monnieri active ingredient. According to another embodiment, the Bacopa monnieri extract comprises at least about 45% Bacopa monnieri active ingredient. According to another embodiment, the Bacopa monnieri extract comprises at least about 50% Bacopa monnieri active ingredient. According to another embodiment, the Bacopa monnieri extract comprises at least about 55% Bacopa monnieri active ingredient. According to another embodiment, the Bacopa monnieri extract comprises at least about 60% Bacopa monnieri active ingredient. According to another embodiment, the Bacopa monnieri extract comprises at least about 65% Bacopa monnieri active ingredient. According to another embodiment, the Bacopa monnieri extract comprises at least about 70% Bacopa monnieri active ingredient. According to another embodiment, the Bacopa monnieri extract comprises at least about 75% Bacopa monnieri active ingredient. According to another embodiment, the Bacopa monnieri extract comprises at least about 80% Bacopa monnieri active ingredient. According to another embodiment, the Bacopa monnieri extract comprises at least about 85% Bacopa monnieri active ingredient. According to another embodiment, the Bacopa monnieri extract comprises at least about 90% Bacopa monnieri active ingredient. According to another embodiment, the Bacopa monnieri extract comprises at least about 95% Bacopa monnieri active ingredient. According to another embodiment, the Bacopa monnieri extract consists essentially of the Bacopa monnieri active ingredient.

According to another embodiment, the Bacopa monnieri active ingredient of the Bacopa monnieri extract comprises a saponin. According to another embodiment, the Bacopa monnieri saponin is a bacoside. Exemplary bacosides include, but are not limited to, bacoside A, bacoside B, bacoposide III, bacopaside IV, bacopaside V, etc.

According to some embodiments, the therapeutic amount of the Bacopa monnieri active ingredient is from about 10 mg to about 200 mg for daily administration to the subject in need thereof. According to some embodiments, the therapeutic amount of the Bacopa monnieri active ingredient is at least about 200 mg, at least about 195 mg, at least about 190 mg, at least about 185 mg, at least about 180 mg, at least about 175 mg, at least about 170 mg, at least about 165 mg, at least about 160 mg, at least about 155 mg, at least about 150 mg, at least about 145 mg, at least about 140 mg, at least about 135 mg, at least about 130 mg, at least about 125 mg, at least about 120 mg, at least about 115 mg, at least about 110 mg, at least about 105 mg, at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, or at least about 10 mg, for daily administration.

According to some embodiments, the *Bacopa monnieri* extract is in a form of a powder, a liquid solution, a suspension, a dispersion, an emulsion, a tablet, a pill, or a capsule. According to one embodiment, the *Bacopa monnieri* extract is in a form of a powder. According to another embodiment, the *Bacopa monnieri* extract is in a form of a liquid solution. According to another embodiment, the *Bacopa monnieri* extract is in a form of a suspension. According to another embodiment, the *Bacopa monnieri* extract is in a form of a dispersion. According to another embodiment, the *Bacopa monnieri* extract is in a form of an emulsion. According to another embodiment, the *Bacopa monnieri* extract is in a form of a tablet. According to another embodiment, the *Bacopa monnieri* extract is in a form of a pill. According to another embodiment, the *Bacopa monnieri* extract is in a form of a capsule.

Milk Thistle

Milk thistle (botanical name: *Silybum marianum*; other common names: Marian, *Silybum, Silymarin*) is a fine, tall plant, about the size of the Cotton Thistle, with cut into root-leaves, waved and spiny at the margin, of a deep, glossy green, with milk white veins, and is found not uncommonly in hedgebanks and on waste ground. Useful parts of the plant include, e.g., the whole herb, root, leaves, seeds and hull. Milk thistle seeds contain a bioflavonoid complex known as silymarin. Silymarin is an extract of the seeds of the milk thistle plant. According to one embodiment, a standardized extract is 80% silymarin (the *Silybum marianum* active ingredient). This constituent is responsible for the medical benefits of the plant. Silymarin is made up of three parts: silibinin, silidianin, and silicristin. Silibinin is the most active and is largely responsible for the benefits attributed to silymarin. As with other bioflavonoids, silymarin is a powerful antioxidant. Milk thistle extract is useful to protect or reverse damage to liver cells from toxins (e.g., alcohol, drugs, pesticides, poisons), to promote the regeneration of liver cells, to prevent or treat liver disease (e.g., liver cirrhosis, chronic hepatitis, and diabetes due to cirrhosis), indigestion, and cancer. Silymarin's effect in preventing liver destruction and enhancing liver function relates largely to its ability to inhibit free radicals and leukotrienes, and an ability to stimulate liver protein synthesis. Milk thistle (80% silymarin) extract is commercially available, e.g., Stayleaner.com (Las Vegas, Nev., USA). About 0.001 mg to 1000 g of *Silybum marianum* extract is considered safe; increases in cell division in vitro (*PDR for Herbal Medicines* (First Edn). Medical Economics Co., 1998, 1138-9); and a proinflammatory effect at high doses of 250 mg/kg (Johnson et al. Planta Med. 2003, vol. 69, pp. 44-49) have been reported.

According to one embodiment, the therapeutic amount of the *Silybum marianum* extract is from about 15 mg to about 6,000 mg for daily administration. According to one embodiment, the therapeutic amount of the *Silybum marianum* extract is from about 50 mg to about 5,000 mg for daily administration. According to one embodiment, the therapeutic amount of the *Silybum marianum* extract is from about 100 mg to about 3,000 mg for daily administration. According to some embodiments, the therapeutic amount of the *Silybum marianum* extract is at least about 6,000 mg, at least about 5,500 mg, at least about 5,000 mg, at least about 4,500 mg, at least about 4,000 mg, at least about 3,500 mg, at least about 3,000 mg, at least about 2,500 mg, at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, or at least about 15 mg, for daily administration.

According to another embodiment, the *Silybum marianum* active ingredient of the *Silybum marianum* extract is silymarin. According to another embodiment, the *Silybum marianum* extract comprises at least about 20% *Silybum marianum* active ingredient. According to another embodiment, the *Silybum marianum* extract comprises at least about 25% *Silybum marianum* active ingredient. According to another embodiment, the *Silybum marianum* extract comprises at least about 30% *Silybum marianum* active ingredient. According to another embodiment, the *Silybum marianum* extract comprises at least about 35% *Silybum marianum* active ingredient. According to another embodiment, the *Silybum marianum* extract comprises at least about 40% *Silybum marianum* active ingredient. According to another embodiment, the *Silybum marianum* extract comprises at least about 45% *Silybum marianum* active ingredient. According to another embodiment, the *Silybum marianum* extract comprises at least about 50% *Silybum marianum* active ingredient. According to another embodiment, the *Silybum marianum* extract comprises at least about 55% *Silybum marianum* active ingredient. According to another embodiment, the *Silybum marianum* extract comprises at least about 60% *Silybum marianum* active ingredient. According to another embodiment, the *Silybum marianum* extract comprises at least about 65% *Silybum marianum* active ingredient. According to another embodiment, the *Silybum marianum* extract comprises at least about 70% *Silybum marianum* active ingredient. According to another embodiment, the *Silybum marianum* extract comprises at least about 75% *Silybum marianum* active ingredient. According to another embodiment, the *Silybum marianum* extract comprises at least about 80% *Silybum marianum* active ingredient. According to another embodiment, the *Silybum marianum* extract comprises at least about 85% *Silybum marianum* active ingredient. According to another embodiment, the *Silybum marianum* extract comprises at least about 90% *Silybum marianum* active ingredient. According to another embodiment, the *Silybum marianum* extract comprises at least about 95% *Silybum marianum* active ingredient.

According to another embodiment, the *Silybum marianum* extract consists essentially of the *Silybum marianum* active ingredient.

According to some embodiments, the therapeutic amount of the *Silybum marianum* active ingredient is from about 10 mg to about 200 mg for daily administration to the subject in need thereof. According to some embodiments, the therapeutic amount of the *Silybum marianum* active ingredient is at least about 200 mg, at least about 195 mg, at least about 190 mg, at least about 185 mg, at least about 180 mg, at least about 175 mg, at least about 170 mg, at least about 165 mg, at least about 160 mg, at least about 155 mg, at least about 150 mg, at least about 145 mg, at least about 140 mg, at least about 135 mg, at least about 130 mg, at least about 125 mg, at least about 120 mg, at least about 115 mg, at least about 110 mg, at least about 105 mg, at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, or at least about 10 mg, for daily administration.

According to some embodiments, the *Silybum marianum* extract is in a form of a powder, a liquid solution, a suspension, a dispersion, an emulsion, a tablet, a pill, a capsule, a sustained release formulation, or a delayed release formulation. According to one embodiment, the *Silybum marianum* extract is in a form of a powder. According to another embodiment, the *Silybum marianum* extract is in a form of a liquid solution. According to another embodiment, the *Silybum marianum* extract is in a form of a suspension. According to another embodiment, the *Silybum marianum* extract is in a form of a dispersion. According to another embodiment, the *Silybum marianum* extract is in a form of an emulsion. According to another embodiment, the *Silybum marianum* extract is in a form of a tablet. According to another embodiment, the *Silybum marianum* extract is in a form of a pill. According to another embodiment, the *Silybum marianum* extract is in a form of a capsule. According to another embodiment, the *Silybum marianum* extract is in a form of a sustained release formulation. According to another embodiment, the *Silybum marianum* extract is in a form of a delayed release formulation.

Ashwagandha

Ashwagandha (botanical names: *Withania somnifera* and *Physalis flexuosa*; other common names: winter cherry, Ashgandh, Achuvagandi, Amikkira-gadday, Amkulang-kalang, Amukkira-kilzhangu, Amukran-kizhangu, Asagandha, Asana, Asgandh, Asundha, Asvagandhi, Fatarfoda, Hirimaddina-gadday, Hirre-gadday, Penneroo-gadda, Pevette, Sogade-beru, Indian ginseng) is an erect branched shrub native to India, Pakistan and Sri Lanka. Ashwagandha preparations are useful to promote relaxation, bone marrow and women's health (e.g., stabilizes fetus and regenerates hormones), to enhance mental function (e.g., memory and concentration), as an aphrodisiac, and to treat fatigue, stress, cough, infertility, tissue inflammation, cancer, infectious disease, anxiety disorders, panic attacks, rheumatism, arthritis, pain, manic depression, alcoholic paranoia, and schizophrenia, fever, insomnia, infertility, aging, skin inflammations and disorders, alcoholism, Alzheimer's disease, anemia, carbuncles, convalescence, emaciation, HIV support, AIDS, immune system problems, lumbago, multiple sclerosis, muscle energy loss, paralysis, skin afflictions, swollen glands, ulcers, as well as breathing difficulties and as a diuretic. Ashwaganda powder is commertically available, e.g., iHerb Inc. (Monrovia, Calif., USA). About 0.001 mg to 1000 g of *Withania somnifera* extract is considered safe; tranquilizing and hypotensive effects at 25 mg/kg (Mishra et al. Ahern. Med. Rev. 2000, vol 5, 334-346); (Malhotra et al., Indian J. Physiol Pharmacol. 1965, vol 9, 127-136) have been reported.

According to one embodiment, the therapeutic amount of the *Withania somnifera* extract is from about 10 mg to about 4,000 mg for daily administration. According to one embodiment, the therapeutic amount of the *Withania somnifera* extract is from about 50 mg to about 3,000 mg for daily administration. According to one embodiment, the therapeutic amount of the *Withania somnifera* extract is from about 100 mg to about 3,000 mg for daily administration. According to some embodiments, the therapeutic amount of the *Withania somnifera* extract is at least about 4,000 mg, at least about 3,500 mg, at least about 3,000 mg, at least about 2,500 mg, at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 90 mg, at least about 80 mg, at least about 70 mg, at least about 60 mg, at least about 50 mg, at least about 40 mg, at least about 30 mg, at least about 20 mg, or at least about 10 mg, for daily administration.

According to another embodiment, the *Withania somnifera* active ingredient of the *Withania somnifera* extract is withaferin A. According to another embodiment, the *Withania somnifera* extract comprises at least about 5% *Silybum marianum* active ingredient. According to another embodiment, the *Silybum marianum* extract comprises at least about 4.8% *Withania somnifera* active ingredient. According to another embodiment, the *Withania somnifera* extract comprises at least about 4.6% *Withania somnifera* active ingredient. According to another embodiment, the *Withania somnifera* extract comprises at least about 4.4% *Withania somnifera* active ingredient. According to another embodiment, the *Withania somnifera* extract comprises at least about 4.2% *Withania somnifera* active ingredient. According to another embodiment, the *Withania somnifera* extract comprises at least about 4.0% *Withania somnifera* active ingredient. According to another embodiment, the *Withania somnifera* extract comprises at least about 3.8% *Withania somnifera* active ingredient. According to another embodiment, the *Withania somnifera* extract comprises at least about 3.6% *Withania somnifera* active ingredient. According to another embodiment, the *Withania somnifera* extract comprises at least about 3.4% *Withania somnifera* active ingredient. According to another embodiment, the *Withania somnifera* extract comprises at least about 3.2% *Withania somnifera* active ingredient. According to another embodiment, the *Withania somnifera* extract comprises at least about 2.0% *Withania somnifera* active ingredient. According to another embodiment, the *Withania somnifera* extract comprises at least about 2.8% *Withania somnifera* active ingredient. According to another embodiment, the *Withania somnifera* extract comprises at least about 2.6% *Withania somnifera* active ingredient. According to another embodiment, the *Withania somnifera* extract comprises at least about 2.4% *Withania somnifera* active ingredient. According to another embodiment, the *Withania somnifera* extract comprises at least about 2.2% *Withania somnifera* active ingredient. According to another embodiment, the *Withania somnifera* extract comprises at least about 2.0% *Withania somnifera* active ingredient. According to another embodiment, the *Withania somnifera* extract comprises at least about 1.8% *Withania somnifera* active ingredient. According to another embodiment, the *Withania somnifera* extract comprises at least about 1.6% *Withania somnifera* active ingredient. According to another embodiment, the *Withania somnifera* extract comprises at least about 1.4% *Withania somnifera* active ingredient. According to another embodiment, the *Withania somnifera* extract comprises at least about 1.2% *Withania somnifera* active ingredient. According to another embodiment, the *Withania somnifera* extract comprises at least about 1.0% *Withania somnifera* active ingredient. According to another embodiment, the *Withania somnifera* extract comprises at least about 0.9% *Withania somnifera* active ingredient. According to another embodiment, the *Withania somnifera* extract comprises at least about 0.8% *Withania somnifera* active ingredient. According to another embodiment, the *Withania somnifera* extract comprises at least about 0.7% *Withania somnifera* active ingredient. According to another embodiment, the *Withania somnifera* extract comprises at least about 0.6% *Withania somnifera* active ingredient. According to another embodiment, the *Withania somnifera* extract comprises at least about 0.5% *Withania somnifera* active ingredient. According to another embodiment, the *Withania somnifera* extract comprises at least about 0.4% *Withania somnifera* active ingredient. According to another embodiment, the *Withania somnifera* extract comprises at least about 0.3% *Withania somnifera* active ingredient. According to another embodiment, the *Withania somnifera* extract comprises at least about 0.2% *Withania somnifera* active ingredient. According to another embodiment, the *Withania somnifera* extract comprises at least about 0.1% *Withania somnifera* active ingredient.

According to another embodiment, the *Withania somnifera* extract consists essentially of the *Withania somnifera* active ingredient.

According to some embodiments, the therapeutic amount of the *Withania somnifera* active ingredient is in an amount ranging from about 0.1 mg to about 10 mg for daily administration to the subject in need thereof. According to some embodiments, the therapeutic amount of the *Withania somnifera* active ingredient is in an amount at least about 10 mg, at least about 9.8 mg, at least about 9.6 mg, at least about 9.4 mg, at least about 9.2 mg, at least about 9.0 mg, at least about 8.8 mg, at least about 8.6 mg, at least about 8.4 mg, at least about 8.2 mg, at least about 8.0 mg, at least about 7.8 mg, at least about 7.6 mg, at least about 7.4 mg, at least about 7.2 mg, at least about 7.0 mg, at least about 6.8 mg, at least about 6.6 mg, at least about 6.4 mg, at least about 6.2 mg, at least about 6.0 mg, at least about 5.8 mg, at least about 5.6 mg, at least about 5.4 mg, at least about 5.2 mg, at least about 5.0 mg, at least about 4.8 mg, at least about 4.6 mg, at least about 4.4 mg, at least about 4.2 mg, at least about 4.0 mg, at least about 3.8 mg, at least about 3.6 mg, at least about 3.4 mg, at least about 3.2 mg, at least about 3.0 mg, at least about 2.8 mg, at least about 2.6 mg, at least about 2.4 mg, at least about 2.2 mg, at least about 2.0 mg, at least about 1.8 mg, at least about 1.6 mg, at least about 1.4 mg, at least about 1.2 mg, at least about 1.0 mg, at least about 0.9 mg, at least about 0.8 mg, at least about 0.7 mg, at least about 0.6 mg, at least about 0.5 mg, at least about 0.4 mg, at least about 0.3 mg, at least about 0.2 mg, or at least about 0.1 mg for daily administration.

According to some embodiments, the *Withania somnifera* extract is in a form of a powder, a liquid solution, a suspension, a dispersion, an emulsion, a tablet, a pill, a capsule, a sustained release formulation, or a delayed release formulation. According to one embodiment, the *Withania somnifera* extract is in a form of a powder. According to another embodiment, the *Withania somnifera* extract is in a form of a liquid solution. According to another embodiment, the *Withania somnifera* extract is in a form of a suspension. According to another embodiment, the *Withania somnifera* extract is in a form of a dispersion. According to another embodiment, the *Withania somnifera* extract is in a form of an emulsion. According to another embodiment, the *Withania somnifera* extract is in a form of a tablet. According to another embodiment, the *Withania somnifera* extract is in a form of a pill. According to another embodiment, the *Withania somnifera* extract is in a form of a capsule. According to another embodiment, the *Withania somnifera* extract is in a form of a sustained release formulation. According to another embodiment, the *Withania somnifera* extract is in a form of a delayed release formulation.

Green Tea

Green tea (*Camellia sinensis*) extracts are useful in the compositions of the present invention. According to some embodiments of the compositions of the invention, the Green tea extract is standardized for polyphenols. For example, Green tea, 98% polyphenols containing 45% polyphenols such as polyphenol (-)-epigallocatechin gallate (EGCG) is prepared from the leaf of the tea herb *Camellia sinensis*. Polyphenols, e.g., EGCG, in green tea are useful to protective against certain cancers, and they are also potent antioxidants. Green tea preparations are useful to promote immune function and to treat high cholesterol, heart disease, infection (e.g., *Staphylococcus aureus* infection, skin infection, bacterial infection, viral infection), acne, aging, immune disorders, dental caries, periodontitis, halitosis, dandruff, cancer, cardiovascular disease (e.g., hypertension, thrombosis, arteriosclerosis), diabetes, elevated blood glucose, diseases of the alimentary canal and respiratory system, influenza hepatitis, liver disease. Green tea extracts are commercially available, e.g., Hunan Kinglong Bio-Resource Co., Ltd., (Xingsha, Changsha, Hunan, P. R. China). About 0.001 mg to 1000 g of Green tea (*Camellia sinensis*) extract is considered safe. Green tea extract contains a stimulant (caffeine); and is a possible gastric irritant (*PDR for Herbal Medicines* (First Edn). Medical Economics Co., 1998, 710-1).

According to one embodiment, the therapeutic amount of the *Camellia sinensis* extract is from about 5 mg to about 2,000 mg for daily administration. According to one embodiment, the therapeutic amount of the *Camellia sinensis* extract is from about 10 mg to about 1,000 mg for daily administration. According to one embodiment, the therapeutic amount of the *Camellia sinensis* extract is from about 50 mg to about 500 mg for daily administration. According to some embodiments, the therapeutic amount of the *Camellia sinensis* extract is at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, at least about 10 mg, or at least about 5 mg, for daily administration.

According to another embodiment, the *Camellia sinensis* active ingredient of the *Camellia sinensis* extract is epigallocatechin gallate (EGCG). According to another embodiment, the *Camellia sinensis* active ingredient of the *Camellia sinensis* extract is a polyphenol. According to another embodiment, the *Camellia sinensis* extract comprises at least about 20% *Camellia sinensis* active ingredient. According to another embodiment, the *Camellia sinensis* extract comprises at least about 25% *Camellia sinensis* active ingredient. According to another embodiment, the *Camellia sinensis* extract comprises at least about 30% *Camellia sinensis* active ingredient. According to another embodiment, the *Camellia sinensis* extract comprises at least about 35% *Camellia sinensis* active ingredient. According to another embodiment, the *Camellia sinensis* extract comprises at least about 40%

*Camellia sinensis* active ingredient. According to another embodiment, the *Camellia sinensis* extract comprises at least about 45% *Camellia sinensis* active ingredient. According to another embodiment, the *Camellia sinensis* extract comprises at least about 50% *Camellia sinensis* active ingredient. According to another embodiment, the *Camellia sinensis* extract comprises at least about 55% *Camellia sinensis* active ingredient. According to another embodiment, the *Camellia sinensis* extract comprises at least about 60% *Camellia sinensis* active ingredient. According to another embodiment, the *Camellia sinensis* extract comprises at least about 65% *Camellia sinensis* active ingredient. According to another embodiment, the *Camellia sinensis* extract comprises at least about 70% *Camellia sinensis* active ingredient. According to another embodiment, the *Camellia sinensis* extract comprises at least about 75% *Camellia sinensis* active ingredient. According to another embodiment, the *Camellia sinensis* extract comprises at least about 80% *Camellia sinensis* active ingredient. According to another embodiment, the *Camellia sinensis* extract comprises at least about 85% *Camellia sinensis* active ingredient. According to another embodiment, the *Camellia sinensis* extract comprises at least about 90% *Camellia sinensis* active ingredient. According to another embodiment, the *Camellia sinensis* extract comprises at least about 95% *Camellia sinensis* active ingredient.

According to another embodiment, the *Camellia sinensis* extract consists essentially of the *Camellia sinensis* active ingredient.

According to some embodiments, the therapeutic amount of the *Camellia sinensis* active ingredient is in an amount ranging from about 10 mg to about 100 mg for daily administration to the subject in need thereof. According to some embodiments, the therapeutic amount of the *Camellia sinensis* active ingredient is at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, or at least about 10 mg, for daily administration.

According to some embodiments, the *Camellia sinensis* extract is in a form of a powder, a liquid solution, a suspension, a dispersion, an emulsion, a tablet, a pill, a capsule, a sustained release formulation, or a delayed release formulation. According to one embodiment, the *Camellia sinensis* extract is in a form of a powder. According to another embodiment, the *Camellia sinensis* extract is in a form of a liquid solution. According to another embodiment, the *Camellia sinensis* extract is in a form of a suspension. According to another embodiment, the *Camellia sinensis* extract is in a form of a dispersion. According to another embodiment, the *Camellia sinensis* extract is in a form of an emulsion. According to another embodiment, the *Camellia sinensis* extract is in a form of a tablet. According to another embodiment, the *Camellia sinensis* extract is in a form of a pill. According to another embodiment, the *Camellia sinensis* extract is in a form of a capsule. According to another embodiment, the *Camellia sinensis* extract is in a form of a sustained release formulation. According to another embodiment, the *Camellia sinensis* extract is in a form of a delayed release formulation.

Turmeric

Turmeric extract (*Curcuma longa*) 95% is prepared from the root or rhizome of the *Curcuma longa* plant (common names: *Curcuma*, Turmeric, Ukon, Goeratji, Kakoenji, Koenjet, Kondin, Kunir, Kunyit, Oendre, Rame, Renet, Temu kuning, Temu kunyit, Tius. Curcumin). *C. longa* is a perennial plant native to India. A compound called curcumin is a potent extract of the root, and has been attributed a wide range of therapeutic benefits. Turmeric extract is useful as an antioxidant, anti-inflammatory, anti-mutagenic agent, anti-cancer agent, cholagogueue, depurative, diuretic, fumitory, hemostatic agent, hepatoprotective agent, lactagogue, stomachic, tonic, and vulnerary. Turmeric preparations are useful to protect the liver from toxins, to reduce platelet aggregation, to prevent or treat inflammatory disease, inflammation, arthritis, psoriasis, cancer (e.g., prostate cancer and breast cancer), pain, Alzheimer's Disease, cardiovascular disease (e.g., arteriosclerosis and atherosclerosis). Turmeric extract that is standardized to 95% curcumin contains turmeric (with 95% curcumin). Turmeric extract 95% is commercially available, e.g., EZ-FITNESS (Northborough, Mass., USA). About 0.001 mg to 1000 g of turmeric extract is considered safe. A possible gastric irritant; and possible antifertility effects at 125 mg/kg (*PDR for Herbal Medicines* (First Edn). Medical Economics Co., 1998, 786-7) have been reported.

According to one embodiment, the therapeutic amount of the *Curcuma longa* extract is from about 5 mg to about 2,000 mg for daily administration. According to one embodiment, the therapeutic amount of the *Curcuma longa* extract is from about 10 mg to about 1,000 mg for daily administration. According to one embodiment, the therapeutic amount of the *Curcuma longa* extract is from about 50 mg to about 500 mg for daily administration. According to some embodiments, the therapeutic amount of the *Curcuma longa* extract is at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, at least about 10 mg, or at least about 5 mg, for daily administration.

According to another embodiment, the *Curcuma longa* active ingredient of the *Curcuma longa* extract is curcumin. According to another embodiment, the *Curcuma longa* extract comprises at least about 20% *Curcuma longa* active ingredient. According to another embodiment, the *Curcuma longa* extract comprises at least about 25% *Curcuma longa* active ingredient. According to another embodiment, the *Curcuma longa* extract comprises at least about 30% *Curcuma longa* active ingredient. According to another embodiment, the *Curcuma longa* extract comprises at least about 35% *Curcuma longa* active ingredient. According to another embodiment, the *Curcuma longa* extract comprises at least about 40% *Curcuma longa* active ingredient. According to another embodiment, the *Curcuma longa* extract comprises at least about 45% *Curcuma longa* active ingredient. According to another embodiment, the *Curcuma longa* extract comprises at least about 50% *Curcuma longa* active ingredient. According to another embodiment, the *Curcuma longa* extract comprises at least about 55% *Curcuma longa* active ingredient. According to another embodiment, the *Curcuma longa* extract comprises at least about 60% *Curcuma longa* active ingredient. According to another embodiment, the *Curcuma longa* extract comprises at least about 65% *Curcuma longa* active ingredient. According to another embodiment, the *Curcuma longa* extract comprises at least about 70% *Curcuma longa* active ingredient. According to another embodiment, the *Curcuma longa* extract comprises at least about 75% *Curcuma longa* active ingredient. According to another embodiment, the *Curcuma longa* extract comprises at least about 80% *Curcuma longa* active ingredient. According to another embodiment, the *Curcuma longa* extract comprises at least about 85% *Curcuma longa* active ingredient. According to another embodiment, the *Curcuma longa* extract comprises at least about 90% *Curcuma longa* active ingredient. According to another embodiment, the *Curcuma longa* extract comprises at least about 95% *Curcuma longa* active ingredient.

According to another embodiment, the *Curcuma longa* extract consists essentially of the *Curcuma longa* active ingredient.

According to some embodiments, the therapeutic amount of the *Curcuma longa* active ingredient is in an amount ranging from 10 mg to 100 mg for daily administration. According to some embodiments, the therapeutic amount of the *Curcuma longa* active ingredient is at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, or at least about 10 mg, for daily administration.

According to some embodiments, the *Curcuma longa* extract is in a form of a powder, a liquid solution, a suspension, a dispersion, an emulsion, a tablet, a pill, a capsule, a sustained release formulation, or a delayed release formulation. According to one embodiment, the *Curcuma longa* extract is in a form of a powder. According to another embodiment, the *Curcuma longa* extract is in a form of a liquid solution. According to another embodiment, the *Curcuma longa* extract is in a form of a suspension. According to another embodiment, the *Curcuma longa* extract is in a form of a dispersion. According to another embodiment, the *Curcuma longa* extract is in a form of an emulsion. According to another embodiment, the *Curcuma longa* extract is in a form of a tablet. According to another embodiment, the *Curcuma longa* extract is in a form of a pill. According to another embodiment, the *Curcuma longa* extract is in a form of a capsule. According to another embodiment, the *Curcuma longa* extract is in a form of a sustained release formulation. According to another embodiment, the *Curcuma longa* extract is in a form of a delayed release formulation.

Gotu Kola

Gotu kola (botanical names: Hydrocotyle asiatica, *Centella asiatica*; other common names: *Centella*, March Pennywort, Indian Pennywort, Hydrocotyle, Brahmi (Sanskrit), Luei Gong Gen (Chinese)) is a slender, creeping perennial plant that grows commonly in swampy areas of India, Sri Lanka, Madagascar, South Africa and the tropics. Gotu kola is distinct from the kola nut. Gotu kola powder is prepared from the leaves and aerial parts of the plant and used for medicinal purposes. Gotu kola powder is useful to promote relaxation, to enhance mental function (e.g., memory and concentration), to promote tissue healing (e.g., wounds, skin, other connective tissues, lymph tissue, blood vessels, and mucous membranes) and to treat fatigue, anxiety, attention deficit disorder, insomnia, skin inflammations, leprosy, cancer, arthritis (e.g., psoriatic arthritis, anklylosing spondvlitis, and rheumatoid arthritis), hemorrhoids, tuberculosis, high blood pressure, congestive heart failure, venous insufficiency (pooling of blood in the veins, usually in the legs), sore throat, hepatitis, syphilis, stomach ulcers, epilepsy, diarrhea, fever, and asthma and as a mild diuretic. Gotu kola powder is commercially available, e.g., @International (Twin Lakes, Wis., USA). About 0.001 mg to 1000 g of *Centella asiatica* (Gotu kola) extract is considered safe. Sedative and antidepressive effects; and a possible hypotensive effect (*PDR for Herbal Medicines* (First Edn). Medical Economics Co., 1998, 729-30) have been reported.

According to one embodiment, the therapeutic amount of the *Centella asiatica* (Gotu kola) extract is from about 10 mg to about 4,000 mg for daily administration. According to one embodiment, the therapeutic amount of the *Centella asiatica* (Gotu kola) extract is from about 50 mg to about 3,000 mg for daily administration. According to one embodiment, the therapeutic amount of the *Centella asiatica* (Gotu kola) extract is from about 100 mg to about 3,000 mg for daily administration. According to some embodiments, the therapeutic amount of the *Centella asiatica* (Gotu kola) extract is at least about 4,000 mg, at least about 3,500 mg, at least about 3,000 mg, at least about 2,500 mg, at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 90 mg, at least about 80 mg, at least about 70 mg, at least about 60 mg, at least about 50 mg, at least about 40 mg, at least about 30 mg, at least about 20 mg, or at least about 10 mg, for daily administration.

According to another embodiment, the *Centella asiatica* (Gotu kola) extract comprises at least about 20% of the *Centella asiatica* (Gotu kola) active ingredient. According to another embodiment, the *Centella asiatica* (Gotu kola) extract comprises at least about 25% *Centella asiatica* (Gotu kola) active ingredient. According to another embodiment, the *Centella asiatica* (Gotu kola) extract comprises at least about 30% *Centella asiatica* (Gotu kola) active ingredient. According to another embodiment, the *Centella asiatica* (Gotu kola) extract comprises at least about 35% *Centella asiatica* (Gotu kola) active ingredient. According to another embodiment, the *Centella asiatica* (Gotu kola) extract comprises at least about 40% *Centella asiatica* (Gotu kola) active ingredient. According to another embodiment, the *Centella asiatica* (Gotu kola) extract comprises at least about 45% *Curcuma longa* active ingredient. According to another embodiment, the *Centella asiatica* (Gotu kola) extract comprises at least about 50% *Centella asiatica* (Gotu kola) active ingredient. According to another embodiment, the *Centella asiatica* (Gotu kola) extract comprises at least about 55% *Centella asiatica* (Gotu kola) active ingredient. According to another embodiment, the *Centella asiatica* (Gotu kola) extract comprises at least about 60% *Centella asiatica* (Gotu kola) active ingredient. According to another embodiment, the *Centella asiatica* (Gotu kola) extract comprises at least about 65% *Centella asiatica* (Gotu kola) active ingredient. According to another embodiment, the *Centella asiatica* (Gotu kola) extract comprises at least about 70% *Centella asiatica* (Gotu kola) active ingredient. According to another embodiment, the *Centella asiatica* (Gotu kola) extract comprises at least about 75% *Centella asiatica* (Gotu kola) active ingredient. According to another embodiment, the *Centella asiatica* (Gotu kola) extract comprises at least about 80% *Centella asiatica* (Gotu kola) active ingredient. According to another embodiment, the *Centella asiatica* (Gotu kola) extract comprises at least about 85% *Centella asiatica* (Gotu kola) active ingredient. According to another embodiment, the *Centella asiatica* (Gotu kola) extract comprises at least about 90% *Centella asiatica* (Gotu kola) active ingredient. According to another embodiment, the *Centella asiatica* (Gotu kola) extract comprises at least about 95% *Centella asiatica* (Gotu kola) active ingredient.

According to another embodiment, the *Centella asiatica* (Gotu kola) extract consists essentially of the *Centella asiatica* (Gotu kola) active ingredient.

According to some embodiments, the therapeutic amount of the *Centella asiatica* (Gotu kola) active ingredient is in an amount ranging from 10 mg to 100 mg for daily administration. According to some embodiments, the therapeutic amount of the *Centella asiatica* (Gotu kola) active ingredient is at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, or at least about 10 mg, for daily administration.

According to some embodiments, the *Centella asiatica* (Gotu kola) extract is in a form of a powder, a liquid solution, a suspension, a dispersion, an emulsion, a tablet, a pill, a capsule, a sustained release formulation, or a delayed release formulation. According to one embodiment, the *Centella asiatica* (Gotu kola) extract is in a form of a powder. According to another embodiment, the *Centella asiatica* (Gotu kola) extract is in a form of a liquid solution. According to another embodiment, the *Centella asiatica* (Gotu kola) extract is in a form of a suspension. According to another embodiment, the *Centella asiatica* (Gotu kola) extract is in a form of a dispersion. According to another embodiment, the *Centella asiatica* (Gotu kola) extract is in a form of an emulsion. According to another embodiment, the *Centella asiatica* (Gotu kola) extract is in a form of a tablet. According to another embodiment, the *Centella asiatica* (Gotu kola) extract is in a form of a pill. According to another embodiment, the *Centella asiatica* (Gotu kola) extract is in a form of a capsule. According to another embodiment, the *Centella asiatica* (Gotu kola) extract is in a form of a sustained release formulation. According to another embodiment, the *Centella asiatica* (Gotu kola) extract is in a form of a delayed release formulation.

*Aloe vera*

*Aloe vera* (common names: medicinal *aloe*, burn plant, Barbados *aloe*, unguentine cactus) is a perennial plant; the strong, fibrous root produces a rosette of fleshy basal leaves as in the agave but considerably smaller that grows wild in East and South Africa and also cultivated in the West Indies and other tropical areas. *Aloe* contains anthraquinone glycosides, resins, polysaccharides, sterols, gelonins, and chromones, which contribute to the herbs medicinal properties. *Aloe* preparations, e.g., sap or powder, are useful as emollients, purgatives, a vulnerary agent, tonic, demulcent, vermifuge, antifungal, emmenagogue. *Aloe* preparations are useful to treat burns, piles, sunburn, wrinkles, headache, insect bites, skin irritations, cuts, ulcers, sores, herpes, jaundice, bursitis, canker sores, sore gums, poison ivy, inflammation, gastritis, and cancer. *Aloe vera* powder is commercially available, e.g., Red Lion International Trading & Brokerage Co. (Fullerton, Calif., USA). About 0.001 mg to 1000 g of *Aloe vera* extract is considered safe. A laxative effect, gastrointestinal cramping (*PDR for Herbal Medicines* (First Edn). Medical Economics Co., 1998, 630-3), and inhibition of thyroid function at 125 mg/kg (Kar et al., J. Ethnopharmacol. 2002, vol 81, 281-5) have been reported.

According to one embodiment, the therapeutic amount of the *Aloe vera* extract is from about 10 mg to about 4,000 mg for daily administration. According to one embodiment, the therapeutic amount of the *Aloe vera* extract is from about 50 mg to about 3,000 mg for daily administration. According to one embodiment, the therapeutic amount of the *Aloe vera* extract is from about 100 mg to about 3,000 mg for daily administration. According to some embodiments, the therapeutic amount of the *Aloe vera* extract is at least about 4,000 mg, at least about 3,500 mg, at least about 3,000 mg, at least about 2,500 mg, at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 90 mg, at least about 80 mg, at least about 70 mg, at least about 60 mg, at least about 50 mg, at least about 40 mg, at least about 30 mg, at least about 20 mg, or at least about 10 mg, for daily administration.

According to another embodiment, the *Aloe vera* extract comprises at least about 20% *Aloe vera* active ingredient. According to another embodiment, the *Aloe vera* extract comprises at least about 25% *Aloe vera* active ingredient. According to another embodiment, the *Aloe vera* extract comprises at least about 30% *Aloe vera* active ingredient. According to another embodiment, the *Aloe vera* extract comprises at least about 35% *Aloe vera* active ingredient. According to another embodiment, the *Aloe vera* extract comprises at least about 40% *Aloe vera* active ingredient. According to another embodiment, the *Aloe vera* extract comprises at least about 45% *Aloe vera* active ingredient. According to another embodiment, the *Aloe vera* extract comprises at least about 50% *Aloe vera* active ingredient. According to another embodiment, the *Aloe vera* extract comprises at least about 55% *Aloe vera* active ingredient. According to another embodiment, the *Aloe vera* extract comprises at least about 60% *Aloe vera* active ingredient. According to another embodiment, the *Aloe vera* extract comprises at least about 65% of the *Aloe vera* active ingredient. According to another embodiment, the *Aloe vera* extract comprises at least about 70% *Aloe vera* active ingredient. According to another embodiment, the *Aloe vera* extract comprises at least about 75% *Aloe vera* active ingredient. According to another embodiment, the *Aloe vera* extract comprises at least about 80% *Aloe vera* active ingredient. According to another embodiment, the *Aloe vera* extract comprises at least about 85% *Aloe vera* active ingredient. According to another embodiment, the *Aloe vera* extract comprises at least about 90% *Aloe vera* active ingredient. According to another embodiment, the *Aloe vera* extract comprises at least about 95% *Aloe vera* active ingredient.

According to another embodiment, the *Aloe vera* extract consists essentially of the *Aloe vera* active ingredient.

According to some embodiments, the therapeutic amount of the *Aloe vera* active ingredient is in an amount ranging from 10 mg to 100 mg for daily administration to the subject in need thereof. According to some embodiments, the therapeutic amount of the *Aloe vera* active ingredient is in an amount at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, or at least about 10 mg, for daily administration.

According to some embodiments, the *Aloe vera* extract is in a form of a powder, a liquid solution, a suspension, a dispersion, an emulsion, a tablet, a pill, a capsule, a sustained release formulation, or a delayed release formulation. According to one embodiment, the *Aloe vera* extract is in a form of a powder. According to another embodiment, the *Aloe vera* extract is in a form of a liquid solution. According to another embodiment, the *Aloe vera* extract is in a form of a suspension. According to another embodiment, the *Aloe vera* extract is in a form of a dispersion. According to another embodiment, the *Aloe vera* extract is in a form of an emulsion. According to another embodiment, the *Aloe vera* extract is in a form of a tablet. According to another embodiment, the *Aloe vera* extract is in a form of a pill. According to another embodiment, the *Aloe vera* extract is in a form of a capsule. According to another embodiment, the *Aloe vera* extract is in a form of a sustained release formulation. According to another embodiment, the *Aloe vera* extract is in a form of a delayed release formulation.

Ginkgo biloba

*Ginkgo biloba* (common name: Maidenhair tree) is a dioecious tree. *Ginkgo* leaf extracts have been shown to have a wide range of biological activities. The leaf extract utilized in medicine is standardized in a multi-step procedure designed to concentrate the desired active principles from the plant. These extracts contain approximately flavone glycosides (primarily composed of quercetin, kaempferol, and isorhamnetin) and terpene lactones (ginkgolides A, B, and C, and bilobalide). Other constituents typically include proanthocyanadins, glucose, rhamnose, organic acids, D-glucaric acid and ginkgolic acid (at most 5 ppm ginkgolic acids). The complex extract itself, rather than a single isolated component, is believed to be responsible for *Ginkgo*'s biological activity. The flavonoid complex can remove free radicals in the peripheral and/or cerebral vascular systems, and inhibit lipid peroxidation. *Ginko biloba* extract is commercially available, e.g., iHerb Inc. (Monrovia, Calif., USA). About 0.001 mg to 1000 g of *Ginko biloba* extract is considered safe. It has been reported to cause gastrointestinal irritation, can cause hypersensitivity reactions, and may interfere with antithrombotic therapy at 240 mg/day (*PDR for Herbal Medicines* (First Edn). Medical Economics Co., 1998, 871-3).

*Ginkgo* has an effect on are stabilizing cell membranes, reducing free radical damage, improving blood circulation and enhancing oxygen and glucose use. *Ginkgo* is believed to be beneficial for the brain, nerves and blood vessels. It is useful to improve short-term memory *Ginkgo biloba* has been used to improve cerebral blood circulation and to protect the nerves against damaging free radicals. *Ginkgo* leaf helps to maintain integrity and permeability of cell walls by inhibiting lipid peroxidation of membranes. *Ginkgo* extracts are useful to prevent or treat age-related physical and mental deterioration (e.g., Alzheimer's Disease and age-related dementia), cardiovascular disease, cerebral vascular insufficiency and impaired cerebral performance, congestive symptoms of premenstrual syndrome, allergies, age-related vision loss, depression, Raynaud's disease, peripheral vascular disease, intermittent claudication, vertigo, equilibrium disorder, prevention of altitude sickness, tinnitus (ringing in the ear), liver fibrosis, macular degeneration, asthma, graft rejection, and immune disorders that induce toxic shock.

According to one embodiment, the therapeutic amount of the *Ginkgo biloba* extract is from about 10 mg to about 4,000 mg for daily administration. According to one embodiment, the therapeutic amount of the *Ginkgo biloba* extract is from about 50 mg to about 3,000 mg for daily administration. According to one embodiment, the therapeutic amount of the *Ginkgo biloba* extract is from about 100 mg to about 3,000 mg for daily administration. According to some embodiments, the therapeutic amount of the *Ginkgo biloba* extract is at least about 4,000 mg, at least about 3,500 mg, at least about 3,000 mg, at least about 2,500 mg, at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 90 mg, at least about 80 mg, at least about 70 mg, at least about 60 mg, at least about 50 mg, at least about 40 mg, at least about 30 mg, at least about 20 mg, or at least about 10 mg, for daily administration.

According to another embodiment, the *Ginkgo biloba* extract comprises at least about 20% *Ginkgo biloba* active ingredient. According to another embodiment, the *Ginkgo biloba* extract comprises at least about 25% *Ginkgo biloba* active ingredient. According to another embodiment, the *Ginkgo biloba* extract comprises at least about 30% *Ginkgo biloba* active ingredient. According to another embodiment, the *Ginkgo biloba* extract comprises at least about 35% *Ginkgo biloba* active ingredient. According to another embodiment, the *Ginkgo biloba* extract comprises at least about 40% *Ginkgo biloba* active ingredient. According to another embodiment, the *Ginkgo biloba* extract comprises at least about 45% *Ginkgo biloba* active ingredient. According to another embodiment, the *Ginkgo biloba* extract comprises at least about 50% *Ginkgo biloba* active ingredient. According to another embodiment, the *Ginkgo biloba* extract comprises at least about 55% *Ginkgo biloba* active ingredient. According to another embodiment, the *Ginkgo biloba* extract comprises at least about 60% *Ginkgo biloba* active ingredient. According to another embodiment, the *Ginkgo biloba* extract comprises at least about 65% *Ginkgo biloba* active ingredient. According to another embodiment, the *Ginkgo biloba* extract comprises at least about 70% *Ginkgo biloba* active ingredient. According to another embodiment, the *Ginkgo biloba* extract comprises at least about 75% *Ginkgo biloba* active ingredient. According to another embodiment, the *Ginkgo biloba* extract comprises at least about 80% *Ginkgo biloba* active ingredient. According to another embodiment, the *Ginkgo biloba* extract comprises at least about 85% *Ginkgo biloba* active ingredient. According to another embodiment, the *Ginkgo biloba* extract comprises at least about 90% *Ginkgo biloba* active ingredient. According to another embodiment, the *Ginkgo biloba* extract comprises at least about 95% *Ginkgo biloba* active ingredient.

According to another embodiment, the *Ginkgo biloba* extract consists essentially of the *Ginkgo biloba* active ingredient.

According to some embodiments, the therapeutic amount of the *Ginkgo biloba* active ingredient is in an amount ranging from 10 mg to 100 mg for daily administration to the subject in need thereof. According to some embodiments, the therapeutic amount of the *Ginkgo biloba* active ingredient is at least about 100 mg, at least about 95 mg, at least about 90 mg, at least about 85 mg, at least about 80 mg, at least about 75 mg, at least about 70 mg, at least about 65 mg, at least about 60 mg, at least about 55 mg, at least about 50 mg, at least about 45 mg, at least about 40 mg, at least about 35 mg, at least about 30 mg, at least about 25 mg, at least about 20 mg, at least about 15 mg, or at least about 10 mg, for daily administration.

According to some embodiments, the *Ginkgo biloba* extract is in a form of a powder, a liquid solution, a suspension, a dispersion, an emulsion, a tablet, a pill, a capsule, a sustained release formulation, or a delayed release formulation. According to one embodiment, the *Ginkgo biloba* extract is in a form of a powder. According to another embodiment, the *Ginkgo biloba* extract is in a form of a liquid solution. According to another embodiment, the *Ginkgo biloba* extract is in a form of a suspension. According to another embodiment, the *Ginkgo biloba* extract is in a form of a dispersion. According to another embodiment, the *Ginkgo biloba* extract is in a form of an emulsion. According to another embodiment, the *Ginkgo biloba* extract is in a form of a tablet. According to another embodiment, the *Ginkgo biloba* extract is in a form of a pill. According to another embodiment, the *Ginkgo biloba* extract is in a form of a capsule. According to another embodiment, the *Ginkgo biloba* extract is in a form of a sustained release formulation. According to another embodiment, the *Ginkgo biloba* extract is in a form of a delayed release formulation.

N-Acetyl Cysteine

N-Acetyl Cysteine (NAC) is an acetylated form of the amino acid cysteine. It is an antioxidant, an antitoxin and immune support substance, and is found naturally in foods. NAC is commercially available, e.g., Doctor's Trust Vitamins (Orlando, Fla., USA).

NAC reacts very slowly with superoxide or the hydrogen peroxide free radicals. It can be seen from the rate constants that GSH is a more effective antioxidant against the hydroxyl radical in comparison to NAC (GSH K2=8.8×10$^9$, NAC K2=1.36×10$^{10}$ at a pH of 1.0). NAC will inhibit HOCl at physiological concentration in a 3:1 ratio (respectively).

NAC is a precursor for glutathione, an important antioxidant that protects cells against oxidative stress. In addition to maintaining intracellular glutathione levels, NAC supplementation has been shown to suppresses Human Immunodeficiency virus (HIV) replication, to be protective against cell damage caused by chemotherapy and radiation therapy, to be immune enhancing, to protect against toxins as acetametaphen and other drugs, mercury, lead, and others, and is mucolytic, that is, it breaks up mucus seen in bronchoulmonary diseases, such as cystic fibrosis, chronic bronchitis, asthma, gastritis, heart attack, angina pectoris, chronic obstructive pulmonary disease, prevention of kidney damage during coronary angiography, Unverricht-Lundborg disease, pseudoporphyria, and pneumonia. It has also been shown to offer protection against the superoxide free radical in porcine aortic endothelial cells and protects animals against paracetamol hepatotoxicity.

According to some embodiments, the N-acetyl cysteine (NAC) is in an amount ranging from about 50 mg to about 5,000 mg for daily administration. According to some embodiments, the N-acetyl cysteine (NAC) is in an amount at least about 5,000 mg, at least about 4,500 mg, at least about 4,000 mg, at least about 3,500 mg, at least about 3,000 mg, at least about 2,500 mg, at least about 2,000 mg, at least about 1,500 mg, at least about 1,000 mg, at least about 900 mg, at least about 850 mg, at least about 800 mg, at least about 750 mg, at least about 700 mg, at least about 650 mg, at least about 600 mg, at least about 550 mg, at least about 500 mg, at least about 450 mg, at least about 400 mg, at least about 350 mg, at least about 300 mg, at least about 250 mg, at least about 200 mg, at least about 150 mg, at least about 100 mg, at least about 90 mg, at least about 80 mg, at least about 70 mg, at least about 60 mg, or at least about 50 mg, for daily administration.

Free radical damage on the clinical level will be determined by the location of the preponderance of the oxidants generated, the type of oxidants, and the generation of pathological prostaglandins. The administration of compositions of the present invention is dependent upon where pathological free radical reactions are taking place. Measuring the rate of the appearance of oxidation products can assess the effectiveness of the compositions of the invention. Effectiveness can also be monitored in patients by their clinical progress.

BOTANICAL COMPOSITIONS

According to one embodiment, the composition for use in treating oxidative stress in a subject in need thereof contains at least two botanical extracts. According to some embodiments, the composition of the invention contains two (2), three (3), four (4), five (5), six (6), seven (7), eight (8), or nine (9) botanical extracts.

According to one embodiment, the composition for use in treating oxidative stress in a subject in need thereof, comprising: a *Bacopa monnieri* extract containing 45% bacosides, a *Silybum marianum* (milk thistle) extract containing 70-80% Silymarin, a *Withania somnifera* (ashwagandha) extract in the form of a powder, a *Camellia sinensis* (green tea) extract containing 98% polyphenols and 45% EGCG, and a *Curcuma longa* (turmeric) extract containing 95% Curcumin is administered at least daily to a subject. According to another embodiment, the composition for use in treating oxidative stress in a subject in need thereof contains the *Bacopa monnieri* extract containing 45% bacosides, the *Silybum marianum* (milk thistle) extract containing 70-80% Silymarin, the *Withania somnifera* (ashwagandha) extract in the form of a powder, the *Camellia sinensis* (green tea) extract containing 98% polyphenols and 45% EGCG, and the *Curcuma longa* (turmeric) extract containing 95% Curcuminin concentrations as detailed below in Table 2.

TABLE 2

Composition of Protandim ®

| Active Ingredient | Quantity | Weight Percent (wt %) Total |
|---|---|---|
| *Bacopa monnieri*, extract 45% bacosides | 150 mg | 22.2 |
| Milk Thistle extract, 70-80% silymarin | 225 mg | 33.3 |
| Ashwagandha powder | 150 mg | 22.2 |
| Green tea, 98% polyphenols, 45% EGCG | 75 mg | 11.1 |
| Turmeric extract, 95% curcumin | 75 mg | 11.1 |
| Total | 675 mg | 99.9 |

According to another embodiment, the composition for use in treating oxidative stress in a subject in need thereof comprises from about 5 wt % to about 50 wt % *Bacopa monnieri* extract (45% bacosides). In one embodiment, the herb-containing composition of the invention contains from about 10 wt % to about 30 wt % *Bacopa monnieri* extract (45% bacosides). According to another embodiment, the composition for use in treating oxidative stress in a subject in need thereof comprises at least about 22 wt % *Bacopa monnieri* extract (45% bacosides).

According to another embodiment, the composition for use in treating oxidative stress in a subject in need thereof, comprises from about 5 wt % to about 60 wt % *Silybum marianum* (milk thistle) extract (70%-80% silymarin). According to another embodiment, the composition for use in treating oxidative stress in a subject in need thereof contains from about 10 wt % to about 50 wt % *Silybum marianum* (milk thistle) extract (70%-80% silymarin). According to another embodiment, the composition for use in treating oxidative stress in a subject in need thereof contains at least about 33 wt % *Silybum marianum* (milk thistle) extract (70%-80% silymarin).

According to another embodiment, the composition for use in treating oxidative stress in a subject in need thereof comprises from about 5 wt % to about 50 wt % *Withania somnifera* (ashwagandha) extract. According to another embodiment, the composition for use in treating oxidative stress in a subject in need thereof contains from about 10 wt % to about 30 wt % *Withania somnifera* (ashwagandha) extract According to another embodiment, the composition for use in treating oxidative stress in a subject in need thereof contains at least about 22 wt % *Withania somnifera* (ashwagandha) extract.

According to another embodiment, the composition for use in treating oxidative stress in a subject in need thereof comprises from about 2.5 wt % to about 25 wt % *Curcuma longa* (turmeric) extract (95% curcumin) of the total weight of active ingredients. According to another embodiment, the composition for use in treating oxidative stress in a subject in need thereof contains from about 5 wt % to about 15 wt % *Curcuma longa* (turmeric) extract (95% curcumin) of the total weight of active ingredients. According to another embodiment, the composition for use in treating oxidative stress in a subject in need thereof, contains at least about 11 wt % *Curcuma longa* (turmeric) extract (95% curcumin) of the total weight of active ingredients.

According to another embodiment, the composition for use in treating oxidative stress in a subject in need thereof comprises from about 2.5 wt % to about 25 wt % *Camellia sinensis* (green tea) (98% polyphenols, 45% EGCG). According to another embodiment, the composition for use in treating oxidative stress in a subject in need thereof contains from about 5 wt % to about 15 wt % *Camellia sinensis* (green tea) (98% polyphenols, 45% EGCG). According to another embodiment, the composition for use in treating oxidative stress in a subject in need thereof contains at least about 11 wt % *Camellia sinensis* (green tea) (45% polyphenols).

According to another embodiment, the composition for use in treating oxidative stress in a subject in need thereof further comprises a *Centella asiatica* (Gotu kola) extract in the form of a powder, a *Gingko biloba* leaf extract and *Aloe vera* extract in the form of a powder as detailed below in Table 3.

TABLE 3

Composition of Protandim ®-I

| Active Ingredient | Amount | Percent Weight Total Active Ingredients |
|---|---|---|
| *Bacopa monnieri* extract, 45% bacosides | 150 mg | 12.77 |
| Milk Thistle extract, 70-80% silymarin | 275 mg | 23.4 |
| Ashwagandha powder | 150 mg | 12.77 |
| Gotu kola power | 150 mg | 12.77 |
| Turmeric extract, 95% curcumin | 75 mg | 6.38 |
| Green tea 98% polyphenols, 45% EGCG | 75 mg | 6.38 |
| *Ginko biloba* leaf extract | 150 mg | 12.77 |
| *Aloe vera* powder | 150 mg | 12.77 |
| Total | 1175 mg | 100 |

According to another embodiment, the composition for use in treating oxidative stress in a subject in need thereof comprises from about 5 wt % to about 50 wt % *Bacopa monnieri* extract (45% bacosides). According to another embodiment, the composition for use in treating oxidative stress in a subject in need thereof comprises from about 10 wt % to about 30 wt % *Bacopa monnieri* extract (45% bacosides). According to another embodiment, the composition for use in treating oxidative stress in a subject in need thereof comprises at least about 22 wt % *Bacopa monnieri* extract (45% bacosides). According to another embodiment, the composition for use in treating oxidative stress in a subject in need thereof comprises at least about 12 wt % *Bacopa monnieri* extract (45% bacosides).

According to another embodiment, the composition for use in treating oxidative stress in a subject in need thereof comprises from about 5 wt % to about 60 wt % *Silybum marianum* (milk thistle) extract (70%-80% silymarin). According to another embodiment, the composition for use in treating oxidative stress in a subject in need thereof comprises from about 10 wt % to about 50 wt % *Silybum marianum* (milk thistle) extract (70%-80% silymarin). According to another embodiment, the composition for use in treating oxidative stress in a subject in need thereof comprises at least about 33 wt % *Silybum marianum* (milk thistle) extract (70%-80% silymarin).

According to another embodiment, the composition for use in treating oxidative stress in a subject in need thereof comprises at least about 23 wt % *Silybum marianum* (milk thistle) extract (70%-80% silymarin).

According to another embodiment, the composition for use in treating oxidative stress in a subject in need thereof comprises from about 5 wt % to about 50 wt % *Withania somnifera* (ashwagandha) powder. According to another embodiment, the composition for use in treating oxidative stress in a subject in need thereof comprises from about 10 wt % to about 30 wt % *Withania somnifera* (ashwagandha) extract. According to another embodiment, the composition for use in treating oxidative stress in a subject in need thereof comprises at least about 22 wt % *Withania somnifera* (ashwagandha) extract. According to another embodiment, the composition for use in treating oxidative stress in a subject in need thereof comprises at least about 12 wt % *Withania somnifera* (ashwagandha) extract.

According to another embodiment, the composition for use in treating oxidative stress in a subject in need thereof comprises from about 2.5 wt % to about 25 wt % *Curcuma longa* (turmeric) extract (95% curcumin). According to another embodiment, the composition for use in treating oxidative stress in a subject in need thereof comprises from about 5 wt % to about 15 wt % *Curcuma longa* (turmeric) extract (95% curcumin). According to another embodiment, the composition for use in treating oxidative stress in a subject in need thereof comprises at least about 11 wt % *Curcuma longa* (turmeric) extract (95% curcumin). According to another embodiment, the composition for use in treating oxidative stress in a subject in need thereof, comprises at least about 6 wt % *Curcuma longa* (turmeric) extract (95% curcumin).

According to another embodiment, the composition for use in treating oxidative stress in a subject in need thereof comprises from about 2.5 wt % to about 25 wt % *Camellia sinensis* (green tea) (98% polyphenols, 45% EGCG). According to another embodiment, the composition for use in treating oxidative stress in a subject in need thereof comprises from about 5 wt % to about 15 wt % *Camellia sinensis* (green tea) (98% polyphenols, 45% EGCG). According to another embodiment, the composition for use in treating oxidative stress in a subject in need thereof comprises at least about 11 wt % *Camellia sinensis* (green tea) (45% polyphenols). According to another embodiment, the composition for use in treating oxidative stress in a subject in need thereof comprises at least about 6 wt % *Camellia sinensis* (green tea) (45% polyphenols).

According to another embodiment, the *Centella asiatica* (Gotu kola) powder is present at a concentration from at least about 5 weight percent to about 50 weight percent. According to another embodiment, the *Centella asiatica* (Gotu kola) powder is present at a concentration from at least about 10 weight percent to about 30 weight percent. According to another embodiment, the Gotu kola powder extract is present at a concentration at least about 12 weight percent.

According to another embodiment, the *Ginko biloba* leaf extract is present at a concentration from at least about 5 weight percent to about 50 weight percent. According to another embodiment, the *Ginko biloba* leaf extract is present at a concentration from at least about 10 weight percent to about 30 weight percent. According to another embodiment, the *Ginko biloba* leaf extract is present at a concentration at least about 12 weight percent.

According to another embodiment, the *Aloe vera* powder is present at a concentration from at least about 5 weight percent to about 50 weight percent. According to another embodiment, the *Aloe vera* powder is present at a concentration from at least about 10 weight percent to about 30 weight percent. According to another embodiment, the *Aloe vera* powder is present at a concentration of at least about 12 weight percent.

According to some embodiments, the composition is in a form of a powder, a liquid solution, a suspension, a dispersion, an emulsion, a tablet, a pill, or a capsule. According to one embodiment, the composition is in a form of a powder. According to another embodiment, the composition is in a form of a liquid solution. According to another embodiment, the composition is in a form of a suspension. According to another embodiment, the composition is in a form of a dispersion. According to another embodiment, the composition is in a form of an emulsion. According to another embodiment, the composition is in a form of a tablet. According to another embodiment, the composition is in a form of a pill. According to another embodiment, the composition is in a form of a capsule.

According to another embodiment, the composition for use in treating oxidative stress in a subject in need thereof is formulated to contain at least one excipient such as, e.g., calcium carbonate; croscarmellose sodium; dicalcium phosphate; magnesium stearate; microcrystalline cellulose; modified cellulose; silica; and stearic acid.

PHARMACEUTICAL COMPOSITIONS AND FORMULATIONS

The compositions of the present invention can be used in beverages, tonics, infusions, or foodstuffs alone, or in combination with other dietary supplements or therapeutics. The compositions of the invention can be used alone or further formulated with pharmaceutically acceptable compounds, vehicles, excipients or adjuvants with a favorable delivery profile, i.e., suitable for delivery to a subject. Such compositions typically comprise the compositions of the invention and a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral, intravenous, intraperitoneal, subcutaneous, intramuscular, intraarticular, intraarterial, intracerebral, intracerebellar, intrabronchial, intrathecal, topical, and aerosol route. The pH can be adjusted with acids or bases, such as hydrochloric acid or sodium hydroxide. Oral compositions generally include an inert diluent or an edible carrier. They can be enclosed in gelatin capsules, caplets or compressed into tablets. For the purpose of oral therapeutic administration, the compositions of the invention can be incorporated with one or more excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring. Excipients can also include, but are not limited to, e.g., calcium carbonate; croscarmellose sodium; dicalcium phosphate; magnesium stearate; microcrystalline cellulose; modified cellulose; silica; and stearic acid.

The compositions of the invention can also be prepared as pharmaceutical compositions in the form of suppositories (e.g., with conventional suppository bases such as cocoa butter and other glycerides) or retention enemas for rectal delivery.

According to one embodiment, the compositions of the invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

According to one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the composition of the invention and the particular therapeutic effect to be achieved, and the limitations inherent in the art of compounding such an active compound for the treatment of individuals. According to another embodiment, the pharmaceutical compositions can be included in a container, pack, or dispenser together with instructions for administration.

The present compositions may be provided as a single dose, however, it is preferred that the compounds be administered in multiple doses. Particularly preferred are intermittent doses, such as twice daily or once daily doses. However beneficial effects are still seen with more sporadic intermittent doses, e.g., once every 36, 48, 60 or 72 hours, or once per week. Duration of treatment will depend on the disorder being treated. For example, as discussed herein, an average 24% decrease of serum CRP levels was observed in human subjects treated intermittently for a 30-day period with the present compositions. Further decrease in serum CRP levels was observed to continue during the 90-day period of the study. Extrapolating this information to a suggested dosage regimen, one week may be sufficient to treat inflammation in post operative surgical patients, whose serum CRP levels usually peak in three days follow surgery, and naturally decline shortly thereafter. Alternatively, chronic conditions such as arthritis or atherosclerosis may require long term therapy over many years. A medical professional will be able to determine dosage levels and intervals in view of the teachings provided herein.

According to some embodiments, the pharmaceutical dosage form is a powder, a liquid solution, a suspension, a dispersion, an emulsion, a tablet, a pill, a capsule, or a paste. According to one embodiment, the pharmaceutical dosage form is a powder. According to another embodiment, the pharmaceutical dosage form is a liquid solution. According to another embodiment, the pharmaceutical dosage form is a suspension. According to another embodiment, the pharmaceutical dosage form is a dispersion. According to another embodiment, the pharmaceutical dosage form is an emulsion. According to another embodiment, the pharmaceutical dosage form is a tablet. According to another embodiment, the pharmaceutical dosage form is a pill. According to another embodiment, the pharmaceutical dosage form is a paste.

METHOD OF INCREASING ANTIOXIDANT ACTIVITY

According to another aspect, the invention provides a method of increasing a level of antioxidant activity in a mammalian subject in need thereof comprising increasing a level of enzyme activity of at least one enzyme, e.g., superoxide dismutase; catalase; and glutathione peroxidase, by administering to the subject an effective amount of an antioxidant-promoting composition of the invention, wherein the effective amount is effective to increase enzyme activity, which decreases the tissue damage caused by pathological free radicals. According to another embodiment, the tissue damage caused by pathological free radicals occurs in a mammalian subject in need thereof or a subject with a disease or condition selected from the group which includes, e.g., inflammation; infection; atherosclerosis; hypertension; cancer; radiation injury; neurological disease; neurodegenerative disease; ischemia/reperfusion injury; aging; wound healing; glutathione deficiency; acquired immunodeficiency syndrome; sickle cell anemia; and diabetes mellitus. According to one embodiment of the method, the antioxidant-promoting composition is administered as an oral dietary supplement.

According to another embodiment, the invention provides a method of reducing the plasma level of C-reactive protein in a mammalian subject by administering to the subject an effective amount of an antioxidant-promoting composition of the invention. According to another embodiment, the antioxidant-promoting composition is administered as an oral dietary supplement. According to another embodiment, the plasma level of C-reactive protein decreases by at least 10% or more in a 30-day period. According to another embodiment, the plasma level of C-reactive protein decreases by at least 20% or more in a 30-day period.

According to another embodiment, the invention provides a method of reducing the blood pressure in a mammalian subject by administering to the subject an effective amount of an antioxidant-promoting composition of the invention. According to another embodiment, the antioxidant-promoting composition is administered as an oral dietary supplement.

Further, it is expected that the above-described active agents, in the amounts listed, will provide a combined remedy for oxidative stress that may be processed, in one embodiment, into a dosage unit for oral administration. This dosage unit is then administered, as a tablet, capsule, gel cap, pellet (globule), or in other carrier suitable for oral administration. Alternatively, the composition could be made available as a powder to be mixed with a suitable liquid, such as water, to form a tonic. According to one embodiment, the formulation of the herb-containing composition of the invention is an oral dietary supplement. As such, an efficient, proper, and effective balance of these active agents can be formulated so as to provide a composition that can be administered as a suitable daily oral dietary supplement.

The described invention further provides a method of preventing, alleviating or treating oxidative stress in a subject. The active agents of the described invention are formulated into a composition that retains the prophylactic and therapeutic antioxidant inducing properties of the individual active agents, providing an additive or even synergistic antioxidant inducing effect relative to the effect of each active alone, while also decreasing the toxic side effect(s), of the individual active agents of the compositions. The compositions of the described invention are useful to reduce or eradicate free and bound radical reactions presently taking place or it may be used as prophylaxis against pathological free or bound radical reactions, which may occur as a result of a possible oxidant promoting incident (e.g., ischemic injury).

METHOD OF QUANTIFYING NRF2 POTENTIAL

According to another aspect, the described invention provides method of quantifying a Nuclear factor-erythroid-2-related factor 2 (Nrf2) transcription factor activating potential of a botanical extract comprising a botanical active ingredient, comprising:
 (1) contacting a first sample of AREc32 cells with the botanical extract and a second sample of AREc32 cells with a buffer control;
 (2) incubating the first sample of AREc32 cells with the botanical extract and the second sample of AREc32 cells with the buffer control for at least 18 hours at 37° C.;
 (3) washing the first and second samples of AREc32 cells from step (2);
 (4) lysing the first and second samples of washed AREc32 cells from step (3);

(5) incubating the lysate from the first and second samples of lysed AREc32 cells from step (4) with D-luciferin; and (6) measuring luminescence of the first and second samples of incubated AREc32 cells from step (5).

According to one embodiment, the botanical extract is selected from the group consisting of:

(a) a *Bacopa monnieri* extract comprising at least one *Bacopa monnieri* active ingredient;
(b) a *Silybum marianum* (milk thistle) extract comprising at least one *Silybum marianum* active ingredient;
(c) a *Withania somnifera* (ashwagandha) extract comprising at least one *Withania somnifera* active ingredient;
(d) a *Camellia sinensis* (green tea) extract comprising at least one *Camellia sinensis* active ingredient;
(e) a *Curcuma longa* (turmeric) extract comprising at least one *Curcuma longa* active ingredient;
(f) a *Centella asiatica* (Gotu kola) extract comprising at least one *Centella asiatica* active ingredient;
(g) an *Aloe vera* extract consisting comprising at least one *Aloe vera* active ingredient;
(h) a *Gingko biloba* extract comprising at least one *Gingko biloba* active ingredient; or a combination thereof.

According to one embodiment, the botanical extract is a *Bacopa monnieri* extract comprising at least one *Bacopa monnieri* active ingredient. According to another embodiment, the botanical extract is a *Silybum marianum* (milk thistle) extract comprising at least one *Silybum marianum* active ingredient. According to another embodiment, the botanical extract is a *Withania somnifera* (ashwagandha) extract comprising at least one *Withania somnifera* active ingredient. According to another embodiment, the botanical extract is a *Camellia sinensis* (green tea) extract comprising at least one *Camellia sinensis* active ingredient. According to another embodiment, the botanical extract is a *Curcuma longa* (turmeric) extract comprising at least one *Curcuma longa* active ingredient. According to another embodiment, the botanical extract is a *Centella asiatica* (Gotu kola) extract comprising at least one *Centella asiatica* active ingredient. According to another embodiment, the botanical extract is an *Aloe vera* extract consisting comprising at least one *Aloe vera* active ingredient. According to another embodiment, the botanical extract is a *Gingko biloba* extract comprising at least one *Gingko biloba* active ingredient.

According to another embodiment, the Nrf2 activating potential of the botanical extract is standardized against Nuclear factor-erythroid-2-related factor 2 (Nrf2) transcription factor activating potential of a substantially pure active ingredient.

According to another embodiment, the Nuclear factor-erythroid-2-related factor 2 (Nrf2) transcription factor activating potential of the botanical extract is associated with an increase in expression of a phase 2 gene.

According to some embodiments, the phase 2 gene is selected from the group consisting of a NAD(P)H:quinone oxidoreductase-1 (NQO1) gene, a superoxide dismutase (SOD) gene, a glutathione S-transferase (GST) gene, a glutathione peroxidase (GPx) gene, a heme oxygenase-1 (HO-1) gene, a glutamate cysteine ligase (GCL) gene, a catalase gene, a thioredoxin gene, or a combination thereof. According to one embodiment, the phase 2 gene is a NAD(P)H:quinone oxidoreductase-1 (NQO1) gene. According to one embodiment, the phase 2 gene is a superoxide dismutase (SOD) gene. According to one embodiment, the phase 2 gene is a glutathione S-transferase (GST) gene. According to one embodiment, the phase 2 gene is a glutathione peroxidase (GPx) gene. According to one embodiment, the phase 2 gene is a heme oxygenase-1 (HO-1) gene. According to one embodiment, the phase 2 gene is a glutamate cysteine ligase (GCL) gene. According to one embodiment, the phase 2 gene is a catalase gene. According to one embodiment, the phase 2 gene is a thioredoxin gene.

According to some embodiments, the increase in expression of the phase 2 gene is an increase in promoter activity of the phase 2 gene, an increase in a level of messenger RNA (mRNA) of the phase 2 gene, an increase in a level of phase 2 protein expressed from the phase 2 gene, or a combination thereof. According to one embodiment, the increase in expression of the phase 2 gene is an increase in promoter activity of the phase 2 gene. According to another embodiment, the increase in expression of the phase 2 gene is an increase in a level of messenger RNA (mRNA) of the phase 2 gene. According to another embodiment, the increase in expression of the phase 2 gene is an increase in a level of phase 2 protein expressed from the phase 2 gene. According to another embodiment, the *Bacopa monnieri* active ingredient is a bacoside selected from the group consisting of bacoside A, bacoside B, bacoposide III, bacopaside IV, bacopaside V, or a combination thereof. According to another embodiment, the *Silybum marianum* active ingredient is silymarin. According to another embodiment, the *Withania somnifera* active ingredient is withaferin A. According to another embodiment, the *Camellia sinensis* active ingredient is epigallocatechin gallate (EGCG). According to another embodiment, the *Curcuma longa* active ingredient is curcumin.

According to another embodiment, the botanical active ingredient has at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 90 fold, at least 95 fold, at least 100 fold, at least 110 fold, at least 120 fold, at least 130 fold, at least 140 fold at least 150 fold, or at least 200 fold Nuclear factor-erythroid-2-related factor 2 (Nrf2) transcription factor-activating potential as compared to an untreated control.

According to another embodiment, the *Bacopa monnieri* active ingredient has at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 90 fold, at least 95 fold, at least 100 fold, at least 110 fold, at least 120 fold, at least 130 fold, at least 140 fold at least 150 fold, or at least 200 fold Nuclear factor-erythroid-2-related factor 2 (Nrf2) transcription factor-activating potential as compared to an untreated control.

According to another embodiment, the *Silybum marianum* active ingredient has at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 90 fold, at least 95 fold, at least 100 fold, at least 110 fold, at least 120 fold, at least 130 fold, at least 140 fold at least 150 fold, or at least 200 fold Nuclear factor-erythroid-2-related factor 2 (Nrf2) transcription factor-activating potential as compared to an untreated control.

According to another embodiment, the *Withania somnifera* active ingredient has at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 90 fold, at least 95 fold, at least 100 fold, at least 110 fold, at least 120 fold, at least 130 fold, at least 140 fold at least 150 fold, or at least 200 fold Nuclear factor-erythroid-2-related factor 2 (Nrf2) transcription factor-activating potential as compared to an untreated control.

According to another embodiment, the *Camellia sinensis* active ingredient has at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 90 fold, at least 95 fold, at least 100 fold, at least 110 fold, at least 120 fold, at least 130 fold, at least 140 fold at least 150 fold, or at least 200 fold Nuclear factor-erythroid-2-related factor 2 (Nrf2) transcription factor-activating potential as compared to an untreated control.

According to another embodiment, the *Curcuma longa* active ingredient has at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 90 fold, at least 95 fold, at least 100 fold, at least 110 fold, at least 120 fold, at least 130 fold, at least 140 fold at least 150 fold, or at least 200 fold Nuclear factor-erythroid-2-related factor 2 (Nrf2) transcription factor-activating potential as compared to an untreated control.

The invention is further defined by reference to the following examples, which are not meant to limit the scope of the present invention. It will be apparent to those skilled in the art that many modifications, both to the materials and methods, may be practiced without departing from the purpose and interest of the invention.

EXAMPLES

Example 1

Botanical Compositions of the Invention Alter Antioxidant Enzymes and Decrease Lipid Peroxidation in Wild Type C57BL/6J Mice I. General Purpose and Study Design The purpose of this study was to observe and effects of an herbal composition of the present invention on normal 4 week old wild type C57BL/6J mice. The exemplary botanical composition, Protandim®-I, is a dietary supplement containing eight botanical extracts, including, *B. monnieri* extract, Milk Thistle extract 70-80%, Ashwagandha powder, Turmeric extract 95% curcumin, Gotu kola powder, *Aloe vera* powder, Green tea (98% Polyphenols, 45% EGCG), and *Ginko biloba* leaf extract and specifically detailed below in Table 6.

TABLE 6

Composition of Protandim ®-I

| Active Ingredient | Amount | Percent Weight Total Active Ingredients |
|---|---|---|
| *Bacopa monnieri* extract, 45% baco sides | 150 mg | 12.77 |
| Milk Thistle extract, 70-80% silymarin | 275 mg | 23.4 |
| Ashwagandha powder | 150 mg | 12.77 |
| Gotu kola power | 150 mg | 12.77 |
| Turmeric extract, 95% curcumin | 75 mg | 6.38 |
| Green tea 98% polyphenols, 45% EGCG | 75 mg | 6.38 |
| *Ginko biloba* leaf extract | 150 mg | 12.77 |
| *Aloe vera* powder | 150 mg | 12.77 |
| Total | 1175 mg | 100 |

The composition was mixed with the powdered diet, then pelleted. Mice were assigned to four groups as defined below in Table 7, receiving dosages ranging from 0 to 1, 3, or times the anticipated human dosage. The estimated human dose for the present studies was 1175 mg/day or 16 mg/kgbw/day. However, in other embodiments of the invention the dosage to a subject is the amount required to yield the desired antioxidant effect.

TABLE 7

Mice received the indicated amounts of Protandim ®-I

| | No. of mice | Diet | Dose µg/gbw/day | Protandim ®-I mg/kg diet |
|---|---|---|---|---|
| Group 1 | 7 | Control | 0 | 0 |
| Group 2 | 8 | 1X | 16 | 100 |
| Group 3 | 7 | 3X | 48 | 300 |
| Group 4 | 8 | 10X | 160 | 1000 |
| TOTAL | 30 | | | |

The amount added was based on the assumption that the average mouse consumes 5 g/d. The amount of Protandim®-I composition received by each mouse in Group 2 was equivalent in mg/gbw to the anticipated human dosage for a 70 kg person. Group 3 received a 3-fold higher dosage of Protandim I and Group 4 received a 10-fold higher dosage of Protandim I. Mice were weighed at day 1 and day 23. After 23 days, the animals were sacrificed and tissues were harvested for analysis. The end points measured included activities of the major antioxidant enzymes SOD, CAT, and GPX in RBCs, liver, and brain. In addition, the extent of lipid peroxidation was assessed by measuring thiobarbituric acid reactive substances (TBARS) in plasma, liver, and brain.

Thiobarbituric acid reactive substances, or TBARS, were determined by the method of Ohkawa et al. (Ohkawa et al., Anal. Biochem., 95: 351-358 (1979), the entire disclosure of which is incorporated herein by reference. The reaction mixture (total volume of 1 ml) contained 50 µl of 8.1% sodium dodecyl sulfate, 0.375 ml of 20% acetic acid and 0.375 ml 0.8% thiobarbituric acid, and 200 µl of plasma or tissue homogenate supernatant. The mixture was heated in boiling water for 1 hr, cooled with tap water and extracted with n-butanol/pyridine (15:1 v/v) by vortexing for 1-2 min. The mixture was then centrifuged at 500-1000 g for 10 min or until a good aqueous-organic phase separation occurred. The organic phase was removed and its absorbance at 532 nm was measured against a reaction mixture blank. A standard curve was prepared with 1,1,3,3-tetramethoxypropane, and TBARS are reported as molar equivalents.

Superoxide dismutase activity was determined by the method of McCord and Fridovich. McCord et al., J. Biol. Chem., 244: 6049-6055 (1969), the entire disclosure of which is incorporated herein by reference.

Catalase was assayed by the method of Beers and Sizer. Beers et al., J. Biol. Chem., 195, pp. 133-140 (1952), the entire disclosure of which is incorporated herein by reference. The disappearance of peroxide is followed spectrophotometrically at 240 nm. The incubation mixture (3 ml) contains 50 µl of sample supernatant in 0.05 M potassium phosphate (pH 7.0) and 0.02 M hydrogen peroxide. The decrease in absorbance recorded at 240 nm for 2 min. The rate of decrease in absorbance per min. is calculated from the initial (45 sec.) linear portion of the curve.

The value of 0.0394 $cm^{-1}$ $\mu mol^{-1}$ is used as the extinction coefficient of $H_2O_2$ One unit of catalase is defined as the amount of enzyme which decomposes 1 µmol of $H_2O_2$/min at 250° C. at pH 7.0 under the specified conditions.

Glutathione peroxidase was assayed as described by Carrillo et al. (Carrillo et al., Life Sci., 48:517-521 (1991)), the entire disclosure of which is incorporated herein by reference.

II. Results

A. Assessment of Protandim®-I Toxicity

To assess any possible toxic effect of Protandim®-I supplementation, animals were weighed at the beginning and at the end of the study, and a percentage weight gain or loss was calculated for each. The most general indication of toxicity is "failure to thrive," which may manifest as a decreased rate of growth, or as an actual weight loss. FIG. 1 shows that supplementation actually caused modest but non-significant increases in growth rate. The absence of toxicity was evidenced as failure to thrive at any level of Protandim®-I supplementation, from the anticipated human dosage (1×) to a level of ten times that amount.

B. Protandim®-I Effect on SOD Activity

Figure 2:
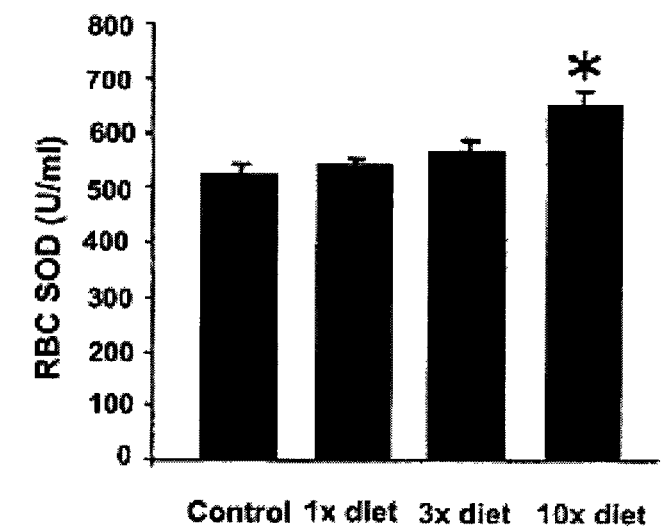
FIG. 2 shows graphs illustrating effect of Protandim®-I dietary supplement on murine red blood cell SOD concentration (RBC SOD). Panel A shows a graph of RBC SOD concentration (U/ml) observed in mice fed 1×, 3× and 10× dosage of Protandim®-I dietary supplement for 23 days. Panel B shows a graph of the percent increase in RBC SOD after 23 days on 1×, 3× and 10× dosage of Protandim®-I dietary supplement. An asterisk indicated statistical significance at $p<0.02$ level.
Figure 2:
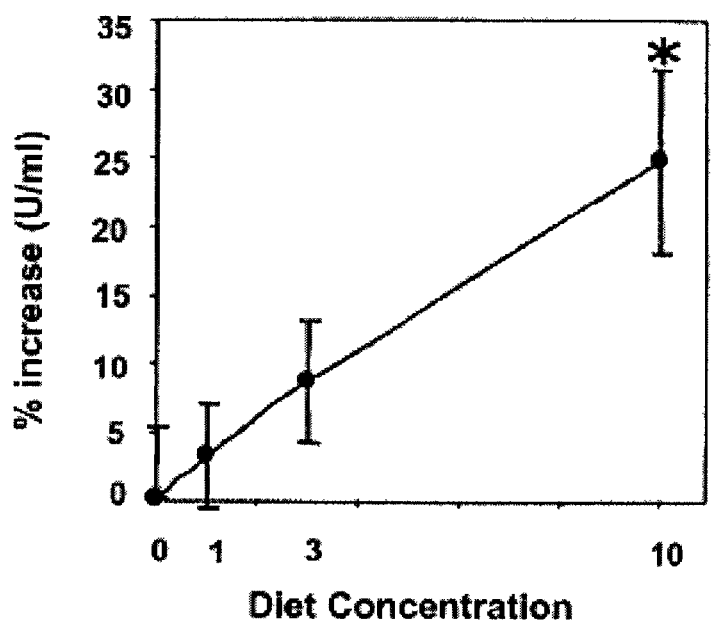

SOD activity was measured in the mice RBCs (FIG. 2), livers (FIG. 3) and brains (FIG. 4) to assess the effect of Protandim®-I on this enzyme. Animals supplemented with Protandim®-I showed a dose-dependent increase in RBC SOD activity, as seen in FIG. 2. A significant 25% increase was seen at the highest level of supplementation. It should be noted that mature, circulating RBC do not contain nuclei, and therefore are not capable of inducing new synthesis of enzymes once they enter the circulation. RBC have a circulating lifespan of 120 days. Thus, during the 23-day course of the experiment about 20% of the RBC would have been replaced by maturing reticulocytes from the bone marrow. As the older RBC are diluted out by the newly produced cells, one may predict that the increase in RBC SOD will proceed linearly with time until all cells have been replaced at 120 days. Therefore, the predicted final RBC SOD activities expected (after 120 days) would be about 16%, at 1×, 44%, at 3×, and 125% at 10× diet.

Figure 3:
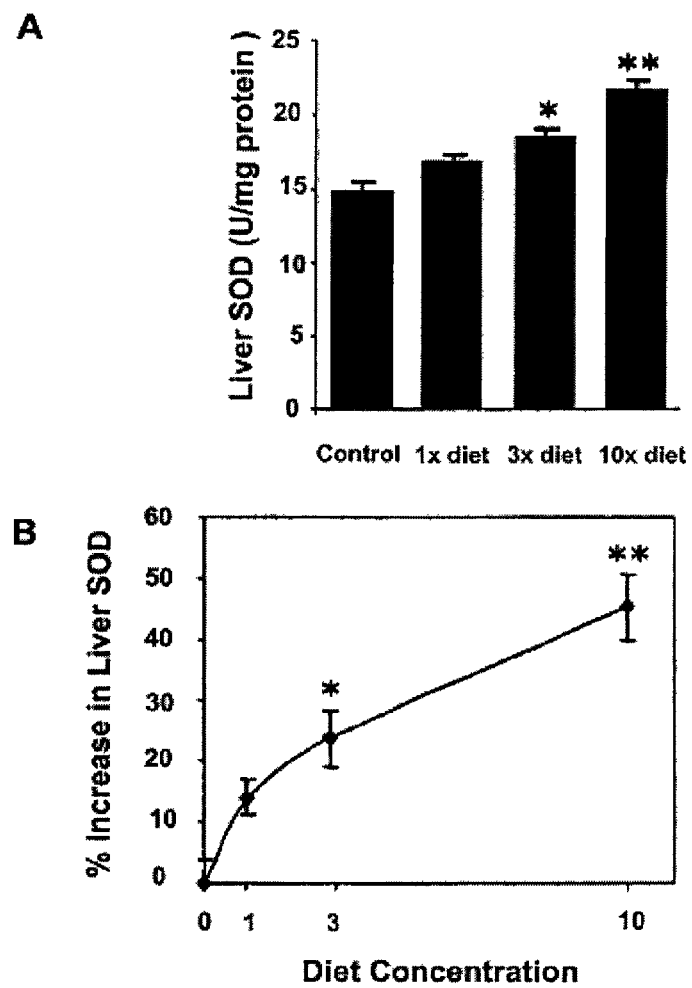
FIG. 3 shows graphs effect of Protandim®-I dietary supplement on murine liver SOD concentration. Panel A shows a graph of liver SOD concentration (U/mg protein) observed in mice fed for 23 days on 1×, 3× and 10× dosage of Protandim®-I dietary supplement. Panel B shows a graph of the percent increase in liver SOD after 23 days on 1×, 3× and 10× dosage of Protandim®-I dietary supplement. An asterisk indicates statistical significance at $p<0.02$ level. A double asterisk indicates statistical significance at $p<0.0001$ level.
Figure 4:
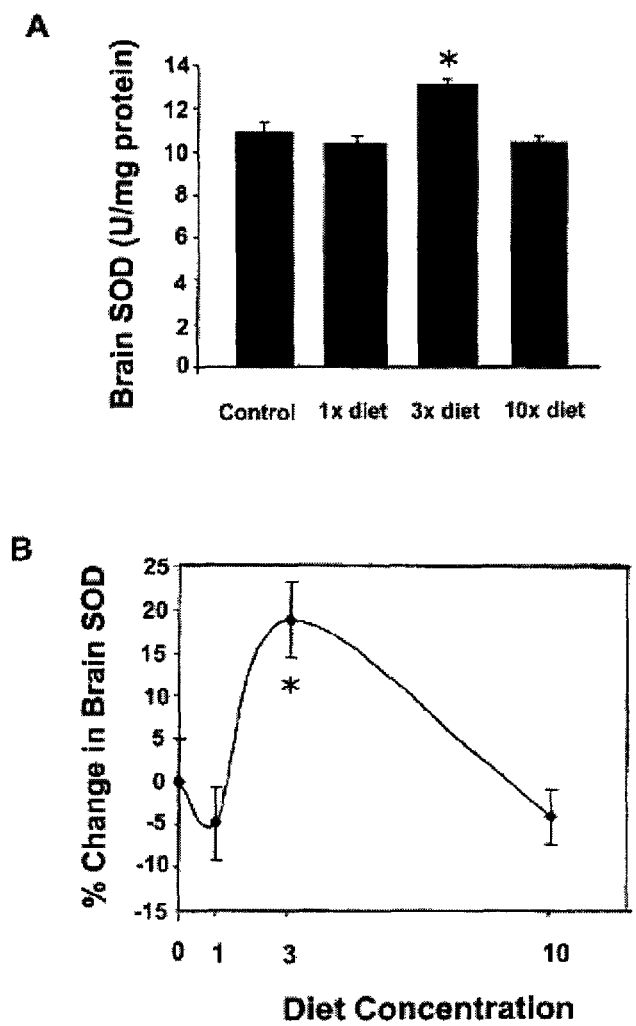
FIG. 4 shows graphs illustrating effect of Protandim®-I dietary supplement on murine brain SOD concentration. Panel A shows a graph of brain SOD concentration (U/mg protein) observed in mice fed 1×, 3× and 10× dosage of Protandim I dietary supplement for 23 days. Panel B shows a graph of the percent change in brain SOD after 23 days on 1×, 3× and 10× dosage of Protandim I dietary supplement. An asterisk indicates statistical significance at $p<0.02$ level.

As detailed in FIG. 3, a dose-dependent increase in liver SOD activity was observed. As shown in the figure, a significant increase was seen at all levels of supplementation: 13% at 1×, 23% at 3×, and 45% at 10× diet. Also, a significant increase in brain SOD activity was seen, but only at the 3× level of Protandim®-I (FIG. 4). The percentage increase was about 20%.

C. Protandim®-I Effect on CAT Activity

Figure 5:
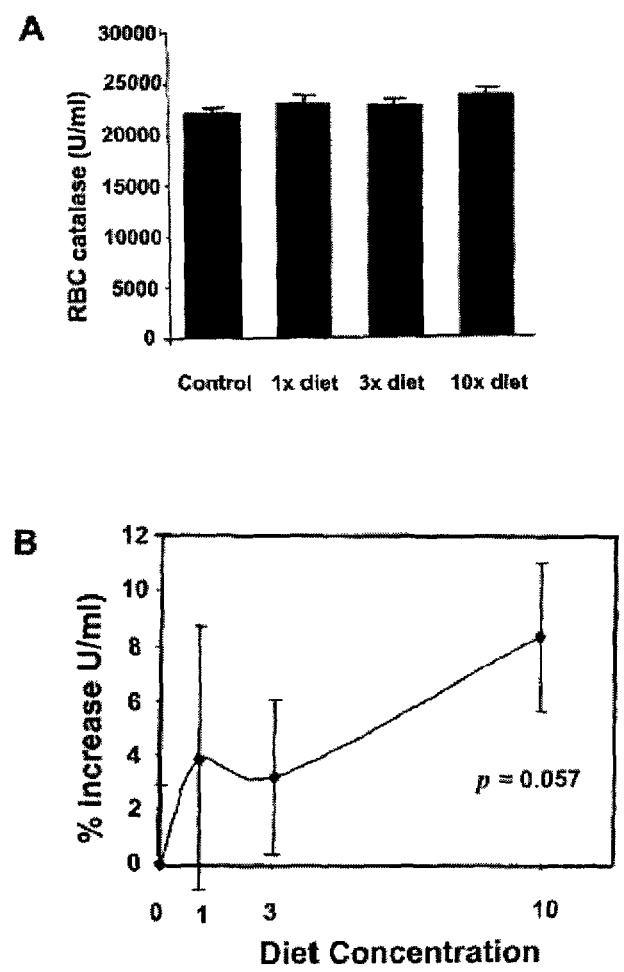
FIG. 5 shows graphs illustrating effect of Protandim®-I dietary supplement on murine red blood cell catalase concentration (RBC CAT). Panel A shows a graph of RBC CAT concentration (U/ml) observed in mice fed 1×, 3× and 10× dosage of Protandim®-I dietary supplement for 23 days. Panel B shows a graph of the percent increase in RBC CAT after 23 days on 1×, 3× and 10× dosage of Protandim®-I dietary supplement.

Animals supplemented with Protandim®-I showed little change in CAT. In RBC, there appeared to be a small dose-dependent increase, with an increase in the 10× group that approached statistical significance ($p=0.057$) (FIG. 5). Based on the turnover of RBC as discussed above, one can predict that the increase in RBC CAT would proceed linearly with time until all cells have been replaced at 120 days. Therefore, the predicted final RBC CAT activities expected after 120 days might approach 10% at 1×, 20% at 3×, and 40% at 10× diet.

Figure 6:
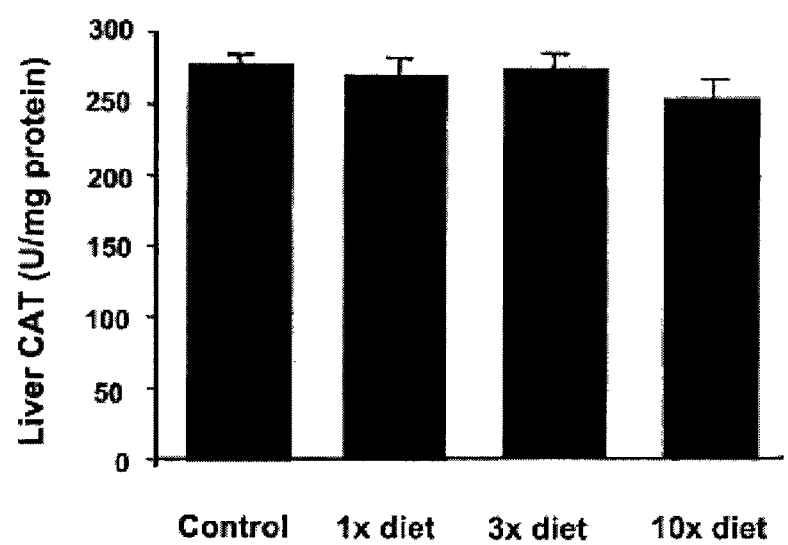
FIG. 6 is a graph illustrating effect of Protandim®-I dietary supplement on murine liver CAT concentration (U/mg protein) observed in mice fed 1×, 3× and 10× dosage of Protandim®-I dietary supplement for 23 days.

Liver CAT was unchanged on 1× and 3× diets, but showed a small non-significant decrease in activity on the 10× diet (FIG. 6). Brain normally contains very little catalase, and the small amounts detected did not change at any diet level.

D. Protandim®-I Effect on GPX Activity

Figure 7:
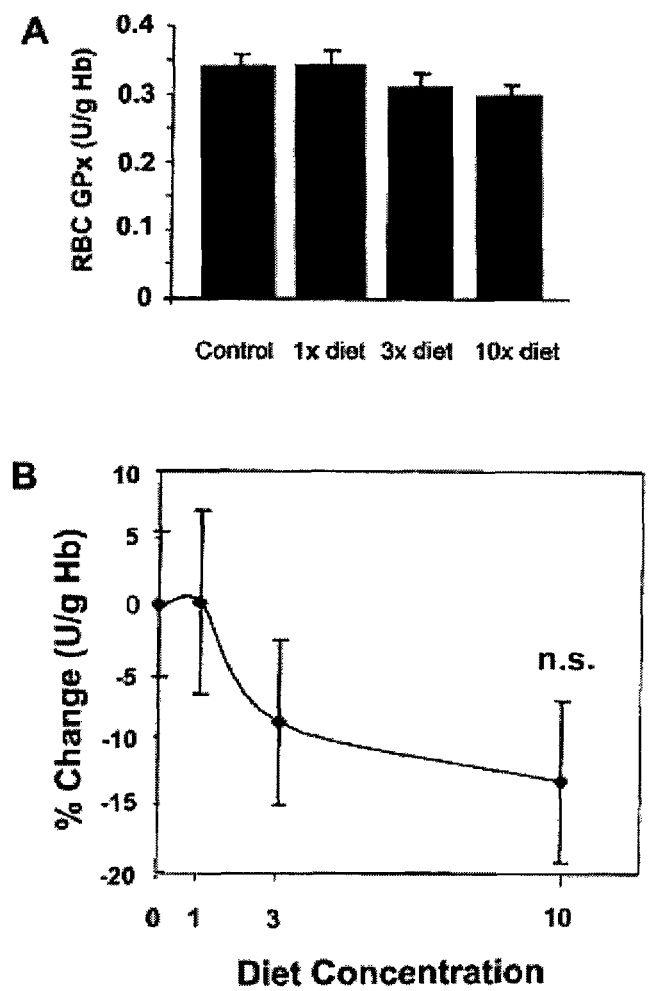
FIG. 7 shows graphs effect of Protandim®-I dietary supplement on murine red blood cell glutathione peroxidase concentration (RBC GPX). Panel A shows a graph of RBC GPX concentration (U/ml) observed in mice fed 1×, 3× and 10× dosage of Protandim®-I dietary supplement for 23 days. Panel B shows a graph of the percent change in RBC GPX (U/g Hb) after 23 days on 1×, 3× and 10× dosage of Protandim®-I dietary supplement.

Animals supplemented with Protandim®-I showed an unexpected decrease in GPX activity. In RBC, there appeared to be a small dose-dependent decrease, with a 13% decrease in the 10× group that was not statistically significant (FIG. 7). Based on the turnover of RBC as discussed above, one can predict that the decrease in RBC GPX would proceed linearly with time until all cells have been replaced at 120 days. Therefore, the predicted decrease in RBC GPX activity expected after 120 days might approach 65% at 10× diet.

Figure 8:
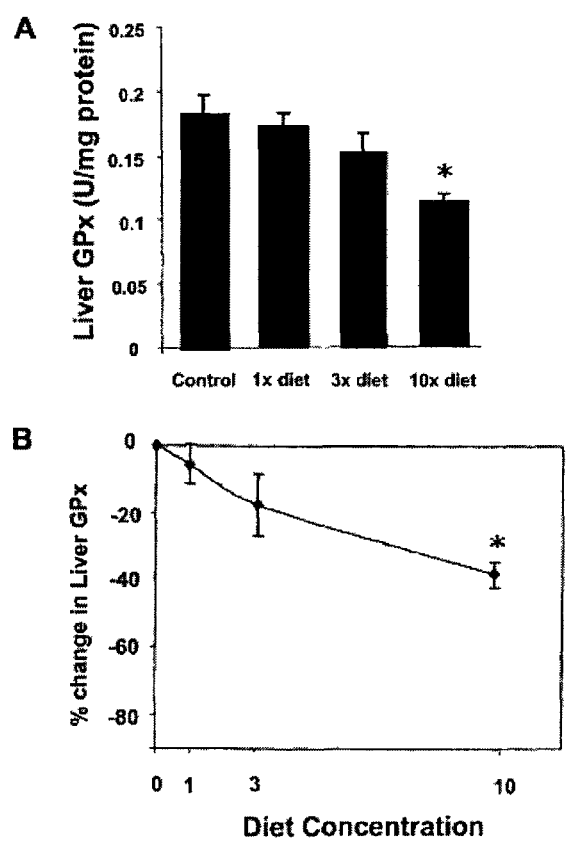
FIG. 8 shows graphs illustrating effect of Protandim®-I dietary supplement on murine liver GPX concentration. Panel A shows a graph of liver GPX concentration (U/mg protein) observed in mice fed 1×, 3× and 10× dosage of Protandim®-I dietary supplement for 23 days. Panel B shows a graph of the percent change in liver GPX after 23 days on 1×, 3× and 10× dosage of Protandim®-I dietary supplement. An asterisk indicated statistical significance at $p<0.004$ level.
Figure 9:
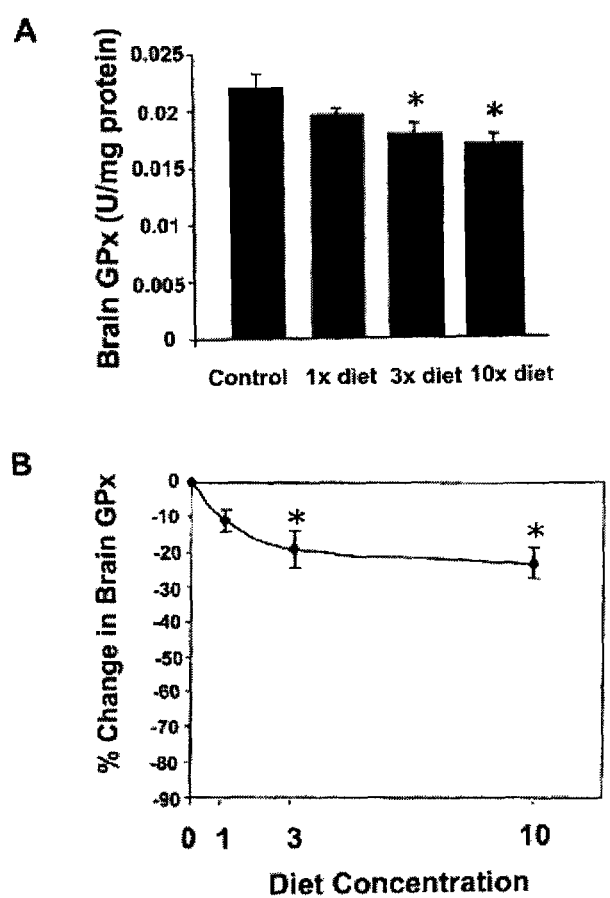
FIG. 9 shows graphs illustrating effect of Protandim®-I dietary supplement on murine brain GPX concentration. Panel A shows a graph of brain GPX concentration (U/mg protein) observed in mice fed 1×, 3× and 10× dosage of Protandim®-I dietary supplement for 23 days. Panel B shows a graph of the percent change in brain GPX after 23 days on various diets of a composition of the present invention. An asterisk indicates statistical significance at $p<0.03$ level.

There was a similar decrease in liver GPX that appeared to be dose-dependent, with a 40% decrease in the 10× group that was statistically significant at $p<0.004$ (FIG. 8). Brain followed a similar pattern, with significant decreases of 19% at 3× ($p<0.03$) and 23% at 10× ($p=0.01$) (FIG. 9).

E. Protandim®-I Effect on Lipid Peroxidation (TBARS)

Figure 10:
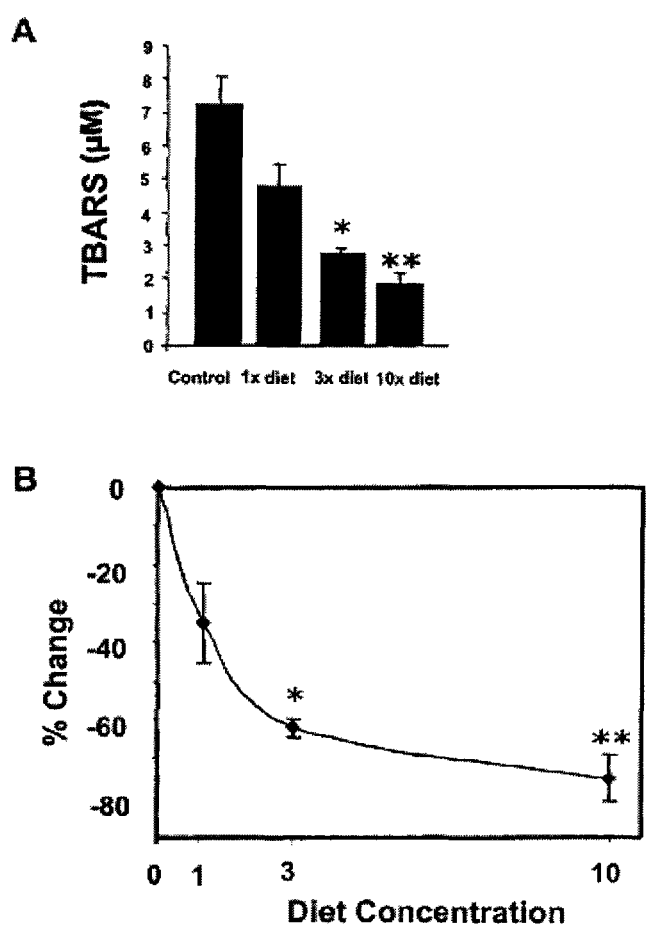
FIG. 10 shows graphs illustrating effect of Protandim®-I dietary supplement on murine plasma lipid peroxidation products measured as TBARS. Panel A shows a graph of plasma TBARS concentration (µM) observed in mice fed 1×, 3× and 10× dosage of Protandim®-I dietary supplement for 23 days. Panel B shows a graph of the percent change in plasma TBARS after 23 days on 1×, 3× and 10× dosage of Protandim®-I dietary supplement. A single asterisk indicates statistical significance at p<0.004 level. A double asterisk indicates statistical significance at the p<0.0004 level.

One objective of Protandim® treatment is to decrease oxidative stress. Our endpoint to assess oxidative stress in this study was TBARS. Animals supplemented with Protandim®-I showed dramatic and highly significant decreases in TBARS in all tissues studied. In plasma, there was a dose-dependent decrease: 35% decrease in animals on the 1× diet; 62% on the 3× diet; and 75% on the 10× diet. The changes in the 3× and 10× groups had high statistical significance: $p=0.004$ and $p=0.0004$, respectively (FIG. 10).

Figure 11:
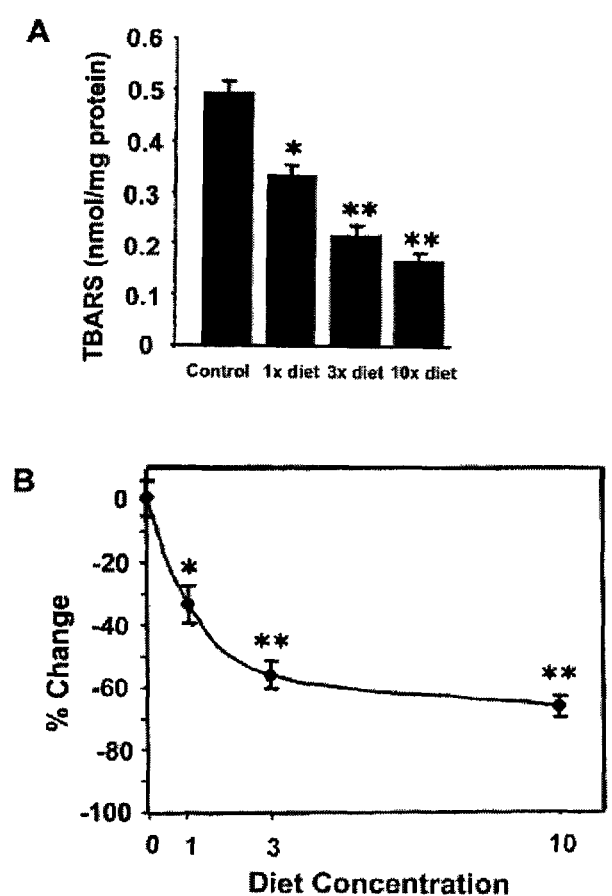
FIG. 11 shows graphs illustrating the effect of diets of a composition of the present invention on murine liver lipid peroxidation products measured as TBARS. Panel A shows a graph of liver TBARS concentration (nmol/mg protein) observed in mice fed 1×, 3× and 10× dosage of Protandim®-I dietary supplement for 23 days. Panel B shows a graph of the percent change in liver TBARS after 23 days on 1×, 3× and 10× dosage of Protandim®-I dietary supplement. A single asterisk indicates statistical significance at p=0.001 level. A double asterisk indicates statistical significance at the p<0.00001 level.
Figure 12:
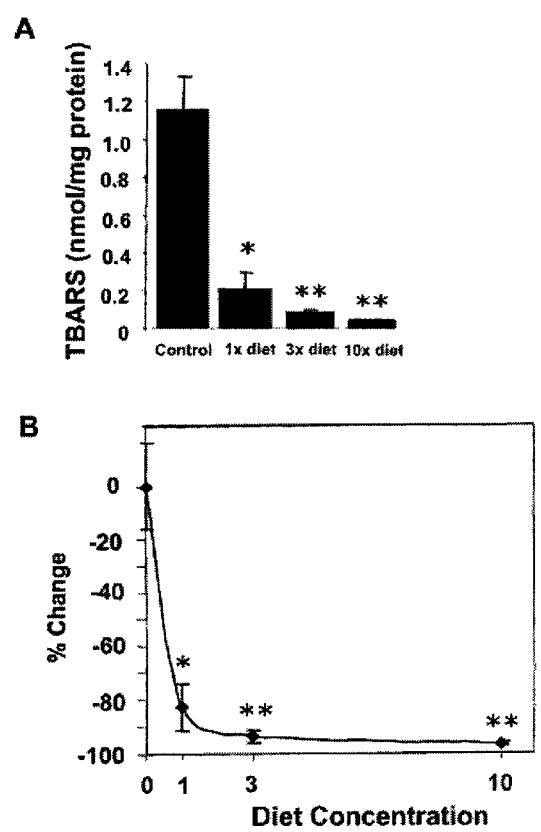
FIG. 12 shows graphs illustrating effect of Protandim®-I dietary supplement on murine brain lipid peroxidation products measured as TBARS. Panel A shows a graph of brain TBARS concentration (nmol/mg protein) observed in mice fed 1×, 3× and 10× dosage of Protandim®-I dietary supplement for 23 days. Panel B shows a graph of the percent change in brain TBARS after 23 days 1×, 3× and 10× dosage of Protandim®-I dietary supplement. A single asterisk indicates statistical significance at p<0.004 level. A double asterisk indicates statistical significance at the p<0.0001 level.

As shown in FIG. 11, in liver homogenates, there was a similar dose-dependent decrease: a 34% decrease in animals on the 1× diet; 56% on the 3× diet; and 66% on the 10× diet. The changes in this tissue had high statistical significance at all there diet concentrations (FIG. 11). In brain homogenates, the effect of Protandim®-I was even more striking: an 83% decrease was seen on the 1× diet ($p<0.004$); 94% on the 3× diet ($p<0.0001$; and 97% on the 10× diet ($p<=0.0001$) (FIG. 12).

III. Summary of Protandim®-I's Effects

The present study established that herbal compositions of the present invention, e.g., Protandim®-I (as defined in Table 3), are a safe and effective way of decreasing oxidative stress. The dosage defined as "1×" (16 mg/kg body weight) seems perfectly positioned for safety and efficacy. The major unexpected finding of the study was that, of the three antioxidant enzymes measured, only SOD was clearly induced. CAT was unaffected, and GPX levels actually showed a significant decline.

Figure 13:
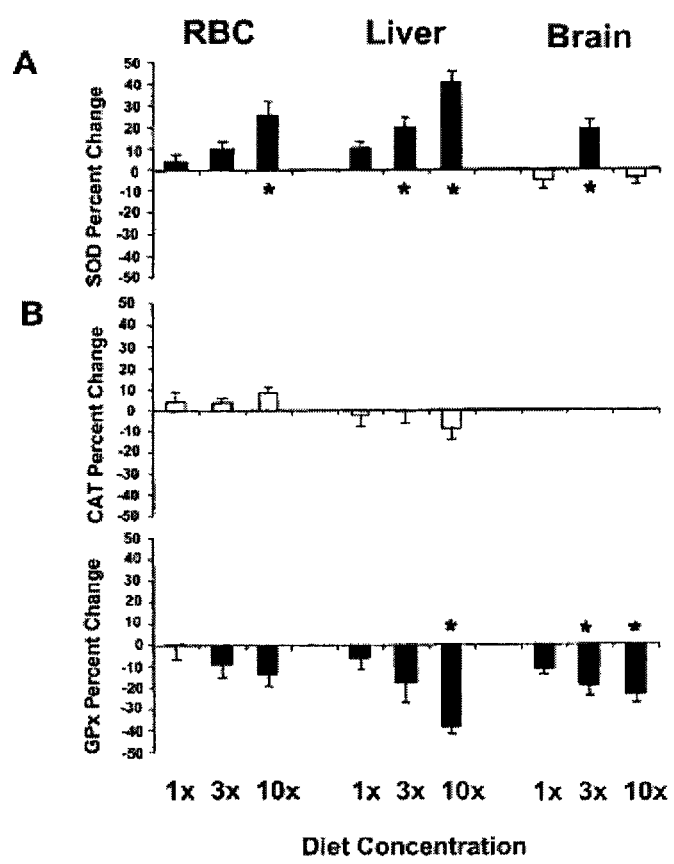
FIG. 13 shows graphs illustrating effect of Protandim®-I dietary supplement on murine SOD, CAT and GPX in various tissues. Panel A shows a graph of the percent change in SOD observed in RBC, liver and brain of mice fed 1×, 3× and 10× dosage of Protandim I dietary supplement for 23 days. Panel B shows a graph of the percent change in CAT observed in RBC and liver of mice fed 1×, 3× and 10× dosage of Protandim®-I dietary supplement for 23 days. Panel C shows a graph of the percent change in GPX observed in RBC, liver and brain of mice fed 1×, 3× and 10× dosage of Protandim®-I dietary supplement for 23 days. A single asterisk indicates statistical significance at relative to the control diet.

FIG. 13 summarizes the Protandim®-induced changes in antioxidant enzymes in blood, liver, and brain where clear and distinctly different patterns emerge. SOD was induced in a dose-dependent fashion, with the only departure from the pattern being seen in brain with the 10× diet. As may be seen in FIG. 14, brain TBARS was, in fact, nearly totally eliminated on the 10× diet, suggesting that protection from oxidative stress was maximal.

Figure 14:
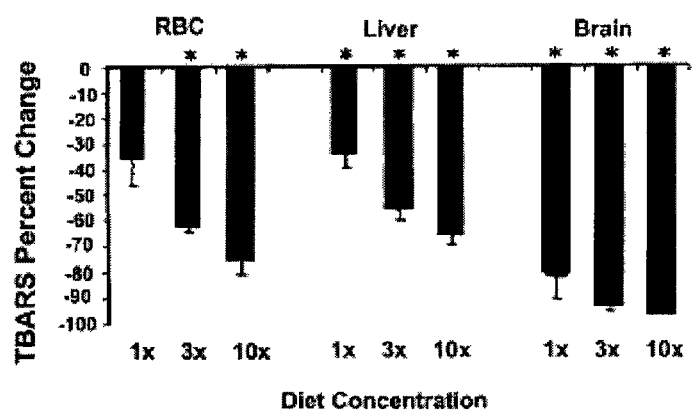
FIG. 14 is a graph illustrating the effect of Protandim®-I dietary supplement on murine lipid peroxidation in various tissues. The graph shows the percent change in lipid peroxidation measured as TBARS in RBC, liver and brain of mice fed 1×, 3× and 10× dosage of Protandim®-I dietary supplement for 23 days. A single asterisk indicates statistical significance at relative to the control diet.

FIG. 14 summarizes the effect of each Protandim®-I diet level on lipid peroxidation in each of the three tissues examined. There was a strong dose-dependency apparent, with no suggestion of any paradoxical increase in lipid peroxidation due to the well-established bell-shaped curve seen with the effect of increasing SOD concentration on rate of lipid peroxidation. This study shows the ability of Protandim®-I to decrease oxidative stress in young, normal mice, without causing a paradoxical increase in oxidative stress at the upper end of a ten-fold dosage range.

Example 2

Botanical Compositions of the Invention Alter Antioxidant Enzymes and Decreased Lipid Peroxidation in Human Subjects I. General Purpose and Design of Study The purpose of this study was to observe the effects of herbal compositions of the present invention on human subjects. An exemplary dietary supplement containing five herbal extracts, called Protandim®-II was administered to sixteen healthy human subjects ranging in age from 20 to 78 years old. The composition of Protandim®-II is shown below in Table 8.

TABLE 8

Composition of Protandim ®-II.

| Active Ingredient | Amount | Percent Weight Total Active Ingredients |
|---|---|---|
| B. monnieri extract, 45% Bacosides | 150 mg | 22.2 |
| Milk Thistle extract, 70-80% Silymarin | 225 mg | 33.3 |
| Ashwagandha powder | 150 mg | 22.2 |
| Turmeric extract, 95% Curcumin | 75 mg | 11.1 |
| Green tea, 98% polyphenols, 45% EGCG | 75 mg | 11.1 |
| Total | 675 mg | 99.9 |

Subjects were assigned to two groups as defined in Table 9.

TABLE 9

Protandim ®-II Dosing of Human Subjects

| | No. of subjects | Age range | Daily supplement of Protandim ®-II |
|---|---|---|---|
| Group 1 | 12 | 20 to 78 | 675 mg |
| Group 2 | 4 | 29 to 66 | 338 mg |
| TOTAL | 16 | | |

Group 1 had twelve subjects who received the full daily Protandim®-II supplement of 675 mg in a single daily capsule for 120 days. At 0, 30, and 120 days, blood was taken by venipuncture for analysis. Group 2 had four additional participants who received one-half as much Protandim® (i.e., half dose), or 338 mg in a single daily capsule for 30 days.

II. Methods

The end points measured in tissue from human subjects included activities of the major antioxidant enzymes SOD and CAT in RBCs. The extent of lipid peroxidation was assessed by measuring thiobarbituric acid reactive substances (TBARS) in plasma. In addition, uric acid was measured in plasma because it is believed to be an endogenous antioxidant of some importance, especially with regard to scavenging and neutralizing the oxidant peroxynitrite. If oxidative stress were decreased, one might expect a sparing effect on plasma uric acid levels. High sensitivity CRP was monitored as an indicator of inflammatory activity, and lipid profiles (total cholesterol, LDL, HDL, and triglycerides) were assessed.

Thiobarbituric acid reactive substances, or TBARS, were determined by the method of Ohkawa et al. (Ohkawa et al., Anal. Biochem., 95: 351-358 (1979), the entire disclosure of which is incorporated herein by reference. The reaction mixture (total volume of 1 ml) contained 50 µl of 8.1% sodium dodecyl sulfate, 0.375 ml of 20% acetic acid and 0.375 ml 0.8% thiobarbituric acid, and 200 µl of plasma or tissue homogenate supernate. The mixture was heated in boiling water for 1 hr, cooled with tap water and extracted with n-butanol/pyridine (15:1 v/v) by vortexing for 1-2 min. The mixture was then centrifuged at 500-1000 g for 10 min or until a good aqueous-organic phase separation occurred. The organic phase was removed and its absorbance at 532 nm was measured against a reaction mixture blank. A standard curve was prepared with 1,1,3,3-tetramethoxypropane, and TBARS are reported as molar equivalents.

Superoxide dismutase activity was determined by the method of McCord and Fridovich. McCord et al., J. Biol. Chem., 244: 6049-6055 (1969), the entire disclosure of which is incorporated herein by reference.

Catalase was assayed by the method of Beers and Sizer. Beers et al., J. Biol. Chem., 195, pp. 133-140 (1952), the entire disclosure of which is incorporated herein by reference. The disappearance of peroxide is followed spectrophotometrically at 240 nm. The incubation mixture (3 ml) contains 50 µl of sample supernatant in 0.05 M potassium phosphate (pH 7.0) and 0.02 M hydrogen peroxide. The decrease in absorbance recorded at 240 nm for 2 min. The rate of decrease in absorbance per min is calculated from the initial (45 sec) linear portion of the curve.

The value of $0.0394$ $cm^{-1}\mu mol^{-1}$ is used as the extinction coefficient of $H_2O_2$.

One unit of catalase is defined as the amount of enzyme which decomposes 1 µmol of $H_2O_2$/min at 25° C. at pH 7.0 under the specified conditions.

High sensitivity C-reactive protein, uric acid, and lipid profile analyses (total cholesterol, LDL, HDL, triglycerides) were performed by the clinical chemistry laboratory of the University Hospital/University of Colorado Health Sciences Center, Denver, Colo.

Glutathione peroxidase was assayed as described by Carrillo et al. (Carrillo et al., Life Sci., 48:517-521 (1991)), the entire disclosure of which is incorporated herein by reference.

III. Results

A. Assessment of Protandim®-II Toxicity or Side Effects

All subjects were instructed to report any suspected adverse reaction or side effect (such as nausea, vomiting, headache, gastrointestinal discomfort, diarrhea, constipation, itching, etc.) to the investigators immediately, and to discontinue use of the supplement. No such reactions or side effects were reported. No toxicity or evidence of other unwanted pharmacological effects of Protandim®-II were noted at either level of supplementation.

B. Effect of Protandim®-II on Lipid Peroxidation and TBARS

The endpoint to assess oxidative stress in this study was TBARS, which measures a family of lipid peroxidation products (mostly lipid hydroperoxides) which break down during the analysis to yield malondialdehyde, which reacts with thiobarbituric acid to yield the chromophore measured at 532 nm. The TBA assay has been somewhat controversial, criticized by some for lack of specificity because it yields higher values than gas chromatographic methods specific for malondialdehyde. The ability of the TBA test to collectively measure lipid peroxidation products, including precursors that will continue to break down to yield malondialdehyde, is a strength of the TBA assay. Gutteridge et al., J. Appl. Biochem., 5:293-299 (1983); Liu et al., Anal. Biochem. 245:161-166 (1997). The entire disclosure of each of these references are incorporated herein by reference. Furthermore, the TBA test is the most widely used in the literature to assess lipid peroxidation, enabling easy comparison with the largest number of studies from other laboratories. In particular, a recent study found plasma TBARS to be a predictor of cardiovascular events in patients with established heart disease, independently of traditional risk factors and inflammatory markers. Walter et al., J. Am. Coll. Cardiol., 44:1996-2002 (2004).

Figure 15:
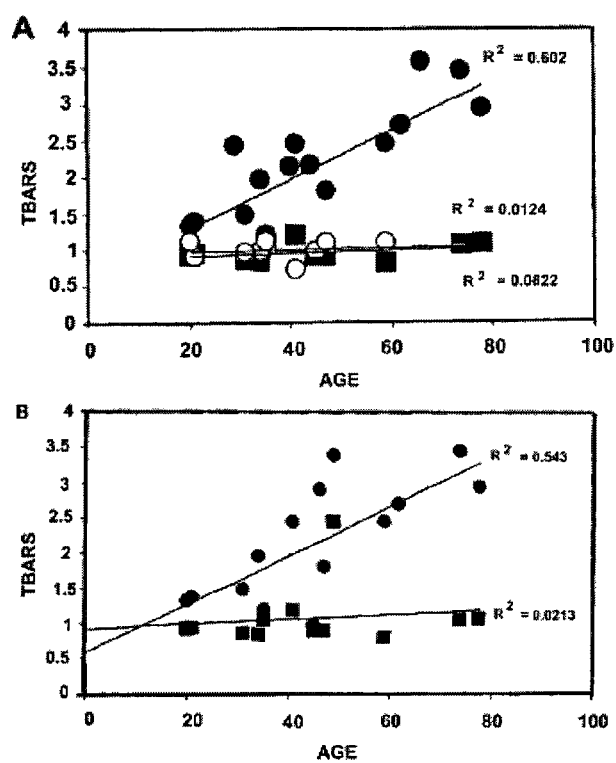
FIG. 15 is a graph showing response of human subjects to dietary supplementation with the herbal composition Protandim®-II. Panel A shows plasma TBARS level in human subjects prior to supplementation with Protandim®-II at 675 mg/day (closed circles), after 30 days of supplementation (gray squares), and after 120 days (open circles). The levels of plasma TBARS dropped an average of 51% (p<0.002) after 30 days of Protandim treatments (gray squares) the age-related increase in TBARS virtually disappeared. Panel B shows plasma TBARS level in normal subjects before supplementation with Protandim®-II showed a strong age-dependent increase in TBARS (circles). The levels of plasma TBARS dropped on average 51% (p<0.002) after 30 days of Protandim®-II (squares) supplementation, and the age-related increase in TBARS virtually disappeared.

FIG. 15 (panel A and panel B) illustrates the age-related increase in plasma TBARS in sixteen healthy human subjects ranging in age from 20 to 78 years old, prior to supplementation with Protandim®-II (solid circles). As shown in FIG. 15, panel A, while there is substantial scatter around the linear regression line, there is a strong correlation with age ($R^2$=0.602) with the oldest individuals showing values approximately three-fold higher than the youngest individuals. After supplementation with Protandim®-II for 30 days (675 mg/day, n=11), the values for plasma TBARS declined as shown by the gray squares. The scatter is remarkably less, and the correlation with age virtually disappears (R.sup.2=0.082). After 30 days, the average TBARS concentration was 0.95±0.04 µM. Nine of these individuals were assayed after 120 days of supplementation (open circles), showing no further change (0.99±0.05 µM; $R^2$=0.012). All subjects showed decreased TBARS after 30 days on Protandim®-II. The age-related increase in lipid peroxidation products disappeared with Protandim®-II supplementation. The changes were maintained at 120 days, with results indistinguishable from those at 30 days.

C. Effect of Protandim®-II on SOD Activity

Figure 16:
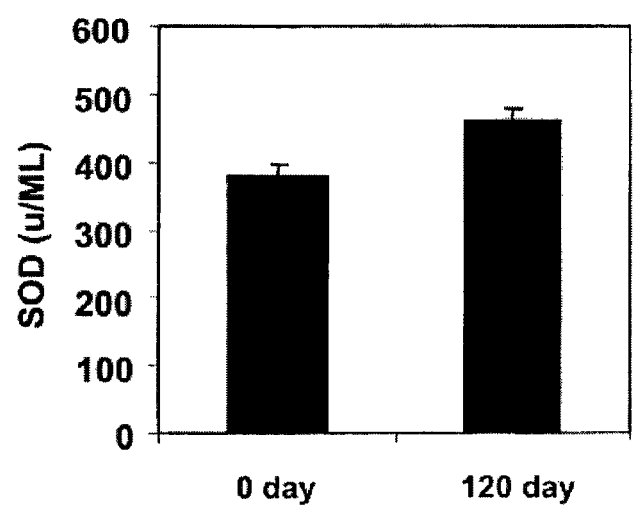
FIG. 16 is a graph illustrating the effect of Protandim®-II dietary supplementation on human SOD in RBCs.

Subjects supplemented with Protandim II showed a statistically significant increase of 22% (n=9, p=0.04) in erythrocyte SOD activity after 120 days of supplementation, as seen in FIG. 16. Erythrocyte SOD at day 0 was 378±17 U/ml and 460±18 U/ml by day 120. It should be noted that mature, circulating erythrocytes do not contain nuclei, and therefore are not capable of inducing new synthesis of enzymes once they enter the circulation. Erythrocytes have a circulating lifespan of 120 days. Thus, during the 120-day course of the experiment 100% of the red cells would have been replaced by maturing reticulocytes from the bone marrow.

D. Effect of Protandim®-II on CAT Activity

Figure 17:
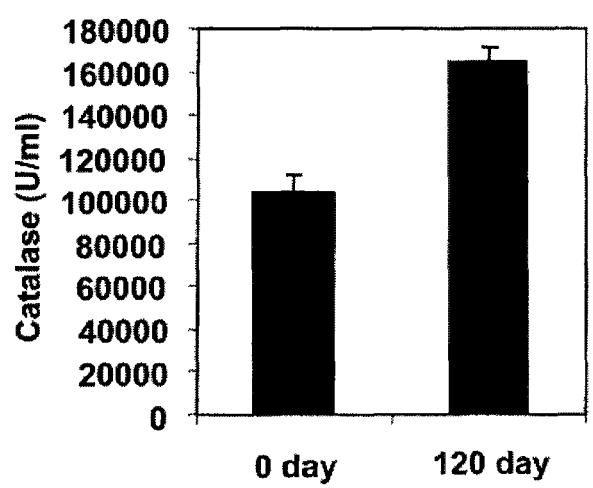
FIG. 17 is a graph illustrating the effect of Protandim®-II dietary supplementation on human CAT in RBCs.

Subjects supplemented with Protandim®-II showed a statistically significant increase of 57% (n=9, p=0.001) in erythrocyte CAT activity after 120 days of supplementation, as seen in FIG. 17. Erythrocyte CAT at day 0 was 104,000±8,000 U/ml and 163,000±8,000 U/ml by day 120. The same considerations regarding turnover and replacement of erythrocytes apply to catalase as discussed above for SOD.

E. Effect of Protandim®-II on Select Blood Parameters

Subjects supplemented with Protandim®-II showed an increase of 4.6% in plasma uric acid concentration after 30 days of supplementation, but this increase did not achieve statistical significance. Because uric acid serves as an endogenous antioxidant, it was anticipated that uric acid levels might rise as a result of increased SOD activity, which would lead to lower levels of peroxynitrite production. Uric acid is thought to scavenge the oxidant peroxynitrite.

Figure 18:
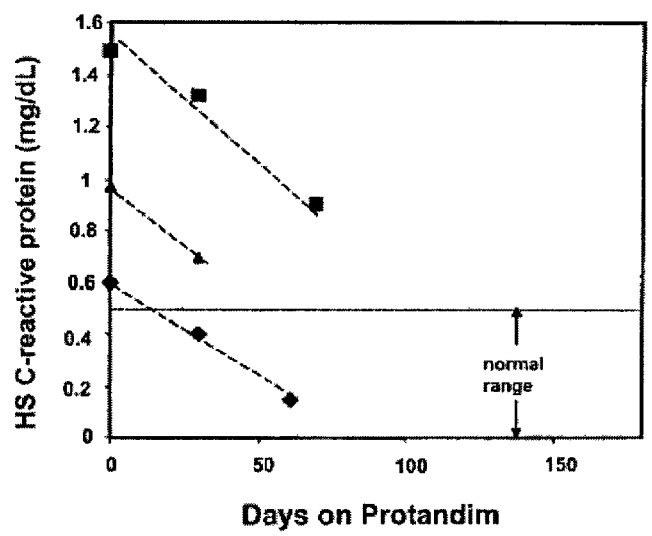
FIG. 18 is a graph illustrating the effect of Protandim®-II dietary supplementation on human CRP protein level.

Three subjects entered the study with elevated CRP levels, and there was a trend towards reduction of these levels with Protandim®-II supplementation. As shown in FIG. 18, the CRP dropped an average of 24% after 30 days of Protandim®-II supplementation. The CRP levels continued to decline at 60-70 days, illustrating a decrease of greater than average of 30%-33% decline in CRP levels over the time tested. No significant changes were seen in total cholesterol, LDL, HDL, or triglycerides.

F. Effect of Low-Dose Protandim®-II (338 mg/day)

Figure 19:
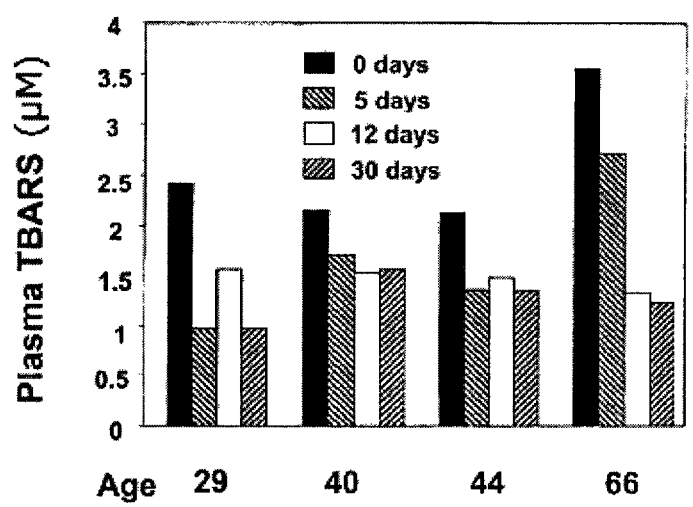
FIG. 19 is a graph illustrating the effect of half-dose Protandim®-II on plasma TBARS in humans subjects. The half-dose Protandim®-II was 338 mg/day dietary supplement.
Figure 20:
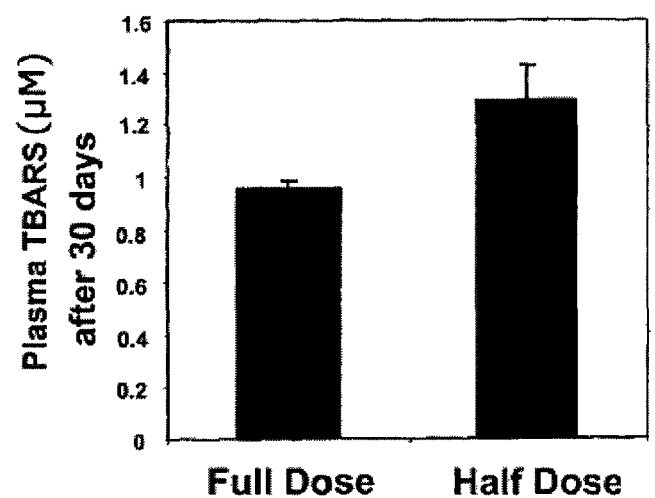
FIG. 20 is a graph comparing the effect of Protandim®-II dosage on plasma TBARS in human subjects. Average plasma TBARS concentrations are shown after 30 days supplementation of Protandim®-II at full-dose (675 mg/day; n=11) and half-dose (338 mg/day; n=4). The difference was statistically significant at p<0.03 as determined by one-tailed paired t-test.

To assess whether the suggested human supplement of 675 mg/day might be more than needed to achieve the desired reduction in oxidative stress, four subjects were given a lower dose of 338 mg/day for 30 days. Blood was drawn from these individuals on day 0, 5, 12 and 30 to provide additional information regarding the time required for the reduction in oxidative stress to manifest. FIG. 19 shows that the response of plasma TBARS is fairly rapid, with most of the change occurring by 5 to 12 days. FIG. 20 shows that the lower dose of Protandim II was not quite as effective as the full dose, lowering TBARS to an average value of 1.29±0.14 µM, (n=4) versus 0.95±0.04 µM, (n=11). Using a one-tailed t-test, this difference was significant at p<0.03. This provides reassurance of the appropriateness of the full recommended dose of Protandim of 675 mg/day is not an excessive dose.

IV. Discussion

The present study established that herbal compositions of the described invention are a safe and effective way of decreasing oxidative stress in healthy human subjects ranging in age from 20 to 78. The dosage defined (675 mg/kg body weight) seems well-positioned for safety and efficacy. The age-dependent increase in oxidative stress as measured by lipid peroxidation was abolished. There was no evidence that the subjects showing the lowest initial levels of oxidative stress were in any way compromised by the modest elevations of SOD and catalase that were achieved—an outcome considered remote but theoretically possible due to our recognition that there is a bell-shaped dose-response curve to SOD. That is, problems can result from too much SOD as well as from too little. The results from this study suggest that all subjects benefited from the Protandim®-II induced elevations of SOD and catalase activities.

Example 3

Botanical Compositions of the Invention Normalize Blood Pressure IN Human Subjects Hypertension has been recognized as a multi-factorial trait resulting from the effect of a combination of environmental and genetic factors, including excess dietary salt or alcohol intake, stress, age, genetics and family history, obesity, physical inactivity, as well as high saturated fat diet. During the past few years, however, a large amount of information has been collected on the vascular inflammation, indicating that inflammation may involve in the initiation as well as development of hypertension. Evidence from animal models as well as patients, have indicated that hypertension, an established major risk factor for coronary artery disease, has been suggested to exert pro-inflammatory actions through the increased expression of several mediators, including leukocyte adhesion molecules, chemokines, specific growth factors, heat shock proteins, endothelin-1, and angiotensin. Endothelial dysfunction as well as increased serum levels of C-reactive protein are observed in patients with hypertension (see, Li., J., Med. Hypotheses. Is hypertension an inflammatory disease? 2005; 64(2):236-240). Assessment of changes in gene expression associated with increased arterial stiffness and gene polymorphisms that increase the risk for vascular stiffening suggests that components of the renin-angiotensin system, matrix metalloproteinases, intracellular signaling, and extracellular matrix components may all be involved in this process. Interventions aimed at these targets may reduce vascular stiffness, lower systolic blood pressure, decrease the prevalence of ISH, and improve outcomes for patients (particularly older patients) with hypertension or other CV conditions (see, Schiffrin E L., Vascular stiffening and arterial compliance: implications for systolic blood pressure. Am J. Hypertens. 2004 December; 17(12 Pt 2):39S-48S). The compositions of the present invention thus provide novel therapeutic strategies to decrease the morbidity as well as mortality of hypertension, and alleviated hypertensive target organ damage.

Subject #1 was a 50 year old man whose blood pressure readings prior to administration of a composition of the invention ranged from 140 to 150 systolic over 90 to 100 diastolic. Following daily ingestion of 1500 mg of a composition containing *B. monnieri* extract, Milk Thistle extract 70-80%, Ashwagandha powder, Turmeric extract 95%, Gotu kola powder, *Aloe vera* powder, Green tea (98% Polyphenols 45% EGCG), and *Ginko biloba* leaf extract for 14 days, the subjects blood pressure was measured as 126 systolic over 74 diastolic. The approximate daily dosage of each of the components of the herb-containing composition was as follows: *B. monnieri* extract (200 mg), Milk Thistle extract 70-80% (300 mg), Ashwagandha powder (200 mg), Turmeric extract (95%) (100 mg), Gotu kola powder (200 mg), *Aloe vera* powder (200 mg), Green tea (98% Polyphenols 45% EGCG) (100 mg), and *Ginko biloba* leaf extract (200 mg).

Figure 21:
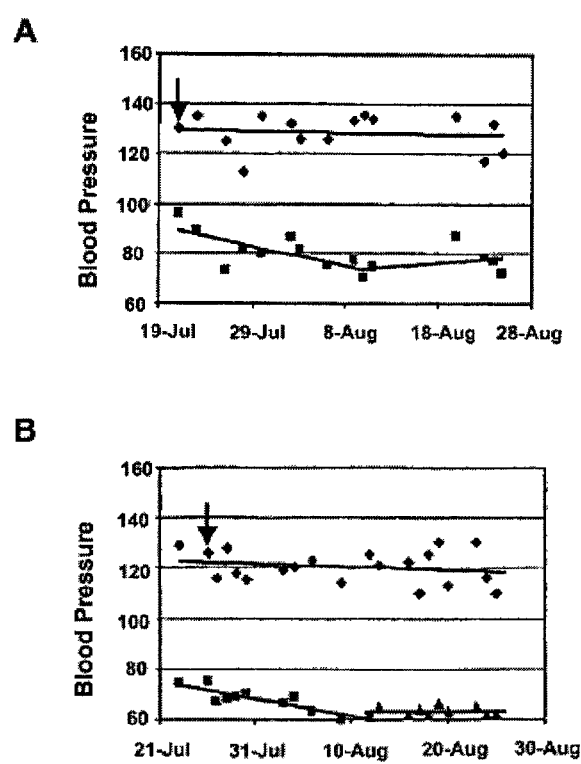
FIG. 21 shows graphs detailing the blood pressure measurements of human subjects administered an herbal composition of the invention. Panel A shows the blood pressure measurements for Subject #2 in Example 2. Panel B shows the blood pressure measurements for Subject #4 in Example 2. The arrow indicates the point in time at which the individual began treatment with an herbal composition of the invention. In both individuals, diastolic blood pressure dropped significantly over a period of about 21 days, remaining constant thereafter.

Subject #2 was a 44 year old woman whose blood pressure readings prior to any treatment were approximately 165 systolic over 113 diastolic to 160 systolic over 103 diastolic. The subject began taking ATENOLOL 25 mg/day (9 months). The ATENOLOL medication reduced the subject's blood pressure to 142 systolic over 98 diastolic to 135 systolic over 96 diastolic, however, the subject's diastolic measurement never got down below 91 (the lowest on ATENOLOL). Following daily ingestion of 1,500 mg of an herb-containing composition containing *B. monnieri* extract, Milk Thistle extract 70-80%, Ashwagandha powder, Turmeric extract 95%, Gotu kola powder, *Aloe vera* powder, Green tea (98% Polyphenols 45% EGCG), and *Ginko biloba* leaf extract for 21 days (while ATENOLOL treatment was continued), the subjects blood pressure was measured as 136 systolic over 70 diastolic. Thus, a drop in diastolic pressure of more than 20 mm was observed during this period (see FIG. 21, panel A). Thereafter, blood pressure remained constant as both treatments continued. The approximate daily dosage of each of the components of the herb-containing composition was as follows: *B. monnieri* extract (200 mg), Milk Thistle extract 70-80% (300 mg), Ashwagandha powder (200 mg), Turmeric extract (95%) (100 mg), Gotu kola powder (200 mg), *Aloe vera* powder (200 mg), Green tea (98% Polyphenols 45% EGCG) (100 mg), and *Ginko biloba* leaf extract (200 mg).

Subject #3 was a 49 year old man whose blood pressure readings prior to administration of a composition of the invention was 135 systolic over 78 diastolic. Following daily ingestion of 1500 mg of a composition containing *B. monnieri* extract, Milk Thistle extract 70-80%, Ashwagandha powder, Turmeric extract 95%, Gotu kola powder, *Aloe vera* powder, Green tea (98% Polyphenols 45% EGCG), and *Ginko biloba* leaf extract for 7 days, the subjects blood pressure was measured as 117 systolic over 75 diastolic. The approximate daily dosage of each of the components of the herb-containing composition was as follows: *B. monnieri* extract (200 mg), Milk Thistle extract 70-80% (300 mg), Ashwagandha powder (200 mg), Turmeric extract (95%) (100 mg), Gotu kola powder (200 mg), *Aloe vera* powder (200 mg), Green tea (98% Polyphenols 45% EGCG) (100 mg), and *Ginko biloba* leaf extract (200 mg).

Subject #4 was a 59 year old man whose blood pressure readings prior to any treatment were approximately 128 systolic over 75 diastolic. Following daily ingestion of 1000 mg of a composition containing *B. monnieri* extract, Milk Thistle extract 70-80%, Ashwagandha powder, Turmeric extract 95%, Gotu kola powder, *Aloe vera* powder, Green tea (98% Polyphenols 45% EGCG), and *Ginko biloba* leaf extract for 21 days, the subject's blood pressure was measured as 125 systolic over 61 diastolic. Thus, a drop in diastolic pressure of about 14 mm was observed during this period (see FIG. 21, panel B). After 21 days, blood pressure remained constant as treatment continued. The approximate daily dosage of each of the components of the herb-containing composition was as follows: *B. monnieri* extract (134 mg), Milk Thistle extract 70-80% (200 mg), Ashwagandha powder (134 mg), Turmeric extract (95%) (67 mg), Gotu kola powder (134 mg), *Aloe vera* powder (134 mg), Green tea (98% Polyphenols, 45% EGCG) (67 mg), and *Ginko biloba* leaf extract (134 mg).

Example 4

Botanical Compositions of the Invention Prevents or Alleviates Migraine Headaches in Human Subjects Migraines afflict about 24 million people in the United States. They may occur at any age, but usually begin between the ages of 10 and 40 and diminish after age 50. Some people experience several migraines a month, while others have only a few migraines throughout their lifetime. Approximately 75% of migraine sufferers are women.

A migraine is a throbbing or pulsating headache that is often one sided (unilateral) and associated with nausea; vomiting; sensitivity to light, sound, and smells; sleep disruption; and depression. Attacks are often recurrent and tend to become less severe as the migraine sufferer ages. Migraines are classified according to the symptoms they produce. The two most common types are migraine with aura and migraine without aura. Less common types include the following: Basilar artery migraine; Carotidynia; Headache-free migraine; Opthalmoplegic migraine; Status migraine The cause of migraine is unknown. The condition may result from a series of reactions in the central nervous system caused by changes in the body or in the environment. There is often a family history of the disorder, suggesting that migraine sufferers may inherit sensitivity to triggers that produce inflammation in the blood vessels and nerves around the brain, causing pain.

A trigger is any stimulus that initiates a process or reaction. Commonly identified migraine triggers include the following: Alcohol (e.g., red wine); environmental factors (e.g., weather, altitude, time zone changes); foods that contain caffeine (e.g., coffee, chocolate); monosodium glutamate (MSG; found in Chinese food); and nitrates (e.g., processed foods, hot dogs); glare; hormonal changes in women; hunger; lack of sleep, medications (over-the-counter and prescription); perfume; stress.

In the present study, a female subject (woman) who routinely suffers migraine headaches was administered a composition of the invention to assess the affect of the composition on the incidence of her migraine headaches. The subject ingested a composition containing *B. monnieri* extract, Milk Thistle extract 70-80%, Ashwagandha powder, Turmeric extract 95%, Gotu kola powder, *Aloe vera* powder, Green tea (98% Polyphenols 45% EGCG), and *Ginko biloba* leaf extract for 30 days. The approximate daily dosage of each of the components of the herb-containing composition was as follows: *B. monnieri* extract (134 mg-200 mg), Milk Thistle extract 70-80% (200 mg-300 mg), Ashwagandha powder (134 mg-200 mg), Turmeric extract (95%) (67 mg-100 mg), Gotu kola powder (134 mg-200 mg), *Aloe vera* powder (134 mg-200 mg), Green tea (98% Polyphenols 45% EGCG) (67 mg-100 mg), and *Ginko biloba* leaf extract (134 mg-200 mg). Following the initiation of administration of the composition of the invention, the subject has not had a migraine headache. The composition of the invention is therefore useful to prevent or alleviate migraine headaches in a subject.

Similarly, the compositions of the present invention are useful to prevent or treat headaches in a subject associated with high altitude (e.g., acute mountain sickness (AMS)). In the context of a recent ascent, a headache, with any one or more of the following symptoms above 2500 meters (8000 feet) qualifies a subject for the diagnosis of AMS: loss of appetite, nausea, or vomiting; fatigue or weakness; dizziness or light-headedness; difficulty sleeping; confusion; staggering gait. The compositions of the present invention are also useful to prevent or treat headaches, both acute and chronic.

Example 5

Synergistic Effect of Protandim® on Induction of Heme Oxygenase-1 (HO-1) Using MIN6 and SK-N-MC Cells The induction of HO-1 by Protandim® was tested by transient transfection of its promoter linked to the luciferase reporter gene in MIN6 cells, a mouse insulinoma cell line, and in SK-N-MC cells, a human neuroblastoma cell line, as reported in Velmurugan, K. et al., "Synergistic induction of heme oxygenase-1 by the components of the antioxidant supplement Protandim," Free Radical Biology & Medicine, 46: 430-440 (2009), the entire disclosure of which is incorporated herein by reference.

Material and Methods

Enriched Fractions of Protandim®

The dietary supplement (675 mg) Protandim® consists of five ingredients: 150 mg *W. somnifera* powder (ashwagandha), 150 mg *B. monnieri* (45% bacosides), 225 mg *S. marianum* (70-80% silymarin), 75 mg *Ca. sinesis* (green tea, 98% polyphenols and 45% (−)-epigallocatechin-3-gallate), and 75 mg curcumin (95%) from turmeric (*Cu. longa*). The alcohol extract of Protandim® was prepared by shaking 675 mg of Protandim with 16.875 ml of 95% ethanol overnight at 4° C. and centrifuging at 5000 rpm (4° C.) for 5 min, and the extract (40 mg/ml) was stored at −80° C. For studies on synergy, the individual components present in 675 mg of Protandim® were extracted in the same volume of alcohol by a similar procedure. Parallel preparations of Protandim® extracts were also prepared with one of the components omitted. The addition of the ethanolic extract of complete Protandim® to the cell culture medium to produce a Protandim® concentration of 10 µg/ml resulted in the following concentrations of each of the putative active components: withanolides from *W. somnifera*, 0.07 µM; bacopasides from *B. monnieri*, 1.1 µM; silymarin from *S. marianum*, 5.5 µM; (−)-epigallocatechin-3-gallate from *Ca. sinesis*, 1.1 µM; and curcumin from *Cu. longa*, 2.8 µM. Controls were treated with the same volume of alcohol used in the treated groups.

HO-1 Promoters

Several HO-1 promoter constructs linked to a firefly luciferase reporter gene were generated as described previously in Alam, J. et al., "Mechanism of heme oxygenase-1 gene activation by cadmium in MCF-7 mammary epithelial cells: role of p38 kinase and Nrf2 transcription factor," J. Biol. Chem. 275:27694-27702; 2000, the entire disclosure of which is incorporated herein by reference. The fulllength promoter construct pHO15luc was generated by cloning a 15-kb promoter fragment of the mouse HO-1 gene into the luciferase reporter gene vector pSK1luc. The HO-1 promoter contains multiple antioxidant response elements (AREs) in the enhancer regions E1 and E2. A 600-bp (SacI/SacI) fragment (E1) of pHO15kluc was deleted to generate the plasmid pHOluc-ΔE1. The plasmid pHOluc-ΔE2 was generated by deletion of the 161-bp AflII/BsrBI fragment (E2). Deletion of both of these fragments resulted in the construct pHOluc-(ΔE1+ΔE2).

Culture of MIN6 and SK-N-MC Cells

SK-N-MC cells, a neuroblastoma cell line, were maintained in minimum essential medium Eagle supplemented with 10% FBS, 100 µg/ml streptomycin, and 100 U/ml penicillin at 37° C. in 5% $CO_2$/humidified air. MIN6 cells, a mouse pancreatic 13-cell line were cultured in DMEM containing 5.6 mM glucose, 10% FBS, 100 µg/ml streptomycin, 100 U/ml penicillin, and 50 µM 13-mercaptoethanol at 37° C. in a humidified atmosphere of 5% $CO_2$. A low-serum (0.1%) medium was used while exposing the cells to the ethanolic extract of Protandim®.

Transfection Procedure

MIN6 or SK-N-MC cells were cultured to 70% confluence in 12-well dishes. Plasmid (1.5 µg) and LipofectAMINE 2000 reagent (3 µl) were separately diluted in 100 µl of Opti-MEM and incubated for 5 min at room temperature. After being mixed, they were incubated at room temperature for another 20 min and the mixture was added to the cells. A constitutively active *Renilla* luciferase (pRL-TK-Luc) was included in the plasmids to correct for transfection efficiency. The transfected cells were cultured in low-serum (0.1%) medium with appropriate treatment for 12 h. The treated cells were washed with cold PBS and then lysed in 100 µl of passive lysis buffer (Promega).

After freezing and thawing, the lysates were centrifuged (10,600 g; 20 min) to collect the supernatant. Firefly luciferase and *Renilla* luciferase activities from transfected cells were measured using the Dual-Glo Luciferase Assay System (Promega). HO-1 promoter activity is defined as the ratio of firefly luciferase to *Renilla* luciferase activity.

Immunochemistry

SK-N-MC cells were cultured on coverslips to 70% confluence. They were incubated in the absence or presence of the ethanolic extract of Protandim® (40 µg/ml) for 6 h. Treated cells were fixed with 4% paraformaldehyde for 30 min at room temperature, washed with PBS and permeabilized by treatment with 0.2% Triton X-100 and 5% BSA in PBS for 90 min at room temperature, and incubated in the presence of Nrf2 antibody (1:200) at 4° C. overnight. After being washed with PBS, the cells were exposed to anti-rabbit IgG linked to Cy3 and 4,6-diamidino-2-phenylindole (DAPI; 2 g/ml; nuclear staining) for 90 min at room temperature. The cells were then washed in PBS, mounted on slides with mounting medium, and examined by fluorescence microscopy.

Western Blot Analysis

After treatment with Protandim® extracts, MIN6 and SK-N-MC cells were washed with ice-cold PBS. Cells were lysed with mammalian protein extraction reagent (Pierce, Rockford, Ill., USA) containing phosphatase inhibitors and protease inhibitor cocktail. The protein content of the lysate was measured as described in Bradford, M. M., "A rapid and sensitive method for the quantitation of microgram quantities of protein utilizing the principles of protein-dye binding," Anal. Biochem. 72:248-254; 1976, the entire disclosure of which is incorporated herein by reference. Diluted samples containing equal amounts of protein were mixed with 2× Laemmli sample buffer and subjected to electrophoresis on 12% SDS-polyacrylamide gels. After transfer to polyvinylidene difluoride membranes, the membranes were blocked with TBST [20 mM Tris-HCl (pH 7.9), 8.5% NaCl, and 0.1% Tween 20] containing 5% nonfat dry milk at room temperature for 1 h and exposed to primary antibodies (1:1000) in TBST containing 5.0% BSA at 4° C. overnight. After being washed in blocking solution, the membranes were exposed to secondary antibodies conjugated to alkaline phosphatase and developed with CDP-Star reagent (New England Biolabs, Beverly, Mass., USA). The intensity of the protein bands was visualized using Fluor-S Multi-Imager and Quantity One software from Bio-Rad. All densitometric values obtained for the HO-1 protein were normalized to β-actin levels obtained on the same blot.

RNA Isolation and Real-Time Quantitative Reverse Transcriptase Polymerase Chain Reaction (RT-PCR)

MIN6 and SK-N-MC cells cultured in 100-mm dishes were exposed to 40 or 20 µg/ml Protandim® ethanolic extract, respectively, for 24 h. RNA was isolated by Qiagen's RNeasy column method. The levels of HO-1 mRNA were examined by real-time quantitative PCR(RT-PCR) using Taq-Man probes. The PCRs were monitored in real time in an ABI Prism 7700 sequence detector (Perkin-Elmer Corp./Applied Biosystems). The sequences of the primers and probes for HO-1 were as follows: mouse (MIN6 cells), forward primer GTGATGGAGCGTCCACAGC, reverse primer TGGTG-GCCTCCTTCAAGG, TaqMan probe 5'-6FAM-CGACAG-CATGCCCCAGGATTTGTC-TAMRA-3'; human (SK-N-MC cells), forward primer AGGCCAAGACTGCGTTCCT, reverse primer GGTGTCATGGGTCAGCAGCT, TaqMan probe 5 '-6FAM-TCAACATCCAGCTCTTTGAGGAGT-TGCAG-TAMRA-3'.

Glutathione Assay

Total glutathione content in Protandim®-treated cells was determined by a standard colorimetric method as described in Anderson, M. E., "Determination of glutathione and glutathione disulfide in biological samples," Methods Enzymol., 113:548-555; 1985, the entire disclosure of which is incorporated herein by reference. The treated cells were rinsed with ice-cold PBS, scraped off from the 100-mm plate, and suspended into 250 µl of ice-cold phosphate buffer (0.1 M, pH 7.4). The cell suspension was vortexed for 20 s, followed by sonication and centrifugation (2500 rpm for 5 min at 4° C.). The cell lysate was mixed with an equal volume of 10% sulfosalicyclic acid and the denatured protein was removed by centrifugation (20 min). One hundred microliters of supernatant was treated with 450 µl of 5,5'-dithiobisnitrobenzoic acid in 0.1 M phosphate buffer (0.2 M, pH 8.0). The absorbance was read at 412 nm along with glutathione standards.

Statistical Analysis

Data are expressed as means±SE. Statistical analysis in this study was performed by one-way ANOVA with Dunnett's multiple comparison test.

Results

Synergy Between the Components of Protandim® in the Induction of the HO-1 Promoter For the studying synergistic effect in the induction of HO-1 at the mRNA levels by Protandim®'s components, MIN6 and SK-N-MC cells were cultured in 100 mm dishes and exposed to an ethanolic extract of Protandim® or ethanolic extracts of its components at concentrations indicated in Table 10 below for 24 hours.

TABLE 10

Concentrations of Protandim ® or its components exposed to MIN6 or SK-N-MC cells

| Protandim ®/Component | For MIN6 cells | For SK-N-MC cells |
|---|---|---|
| Ashwangandha extract (A) | 8.8 µg/ml | 4.4 µg/ml |
| Bacopa extract (B) | 8.8 µg/ml | 4.4 µg/ml |
| Green tea extract (G) | 4.4 µg/ml | 2.2 µg/ml |
| Silymarin extract (S) | 13.2 µg/ml | 6.6 µg/ml |
| Curcumin extract (C) | 4.4 µg/ml | 2.2 µg/ml |
| Protandim ® | 40 µg/ml | 20 µg/ml |

Figure 22A:
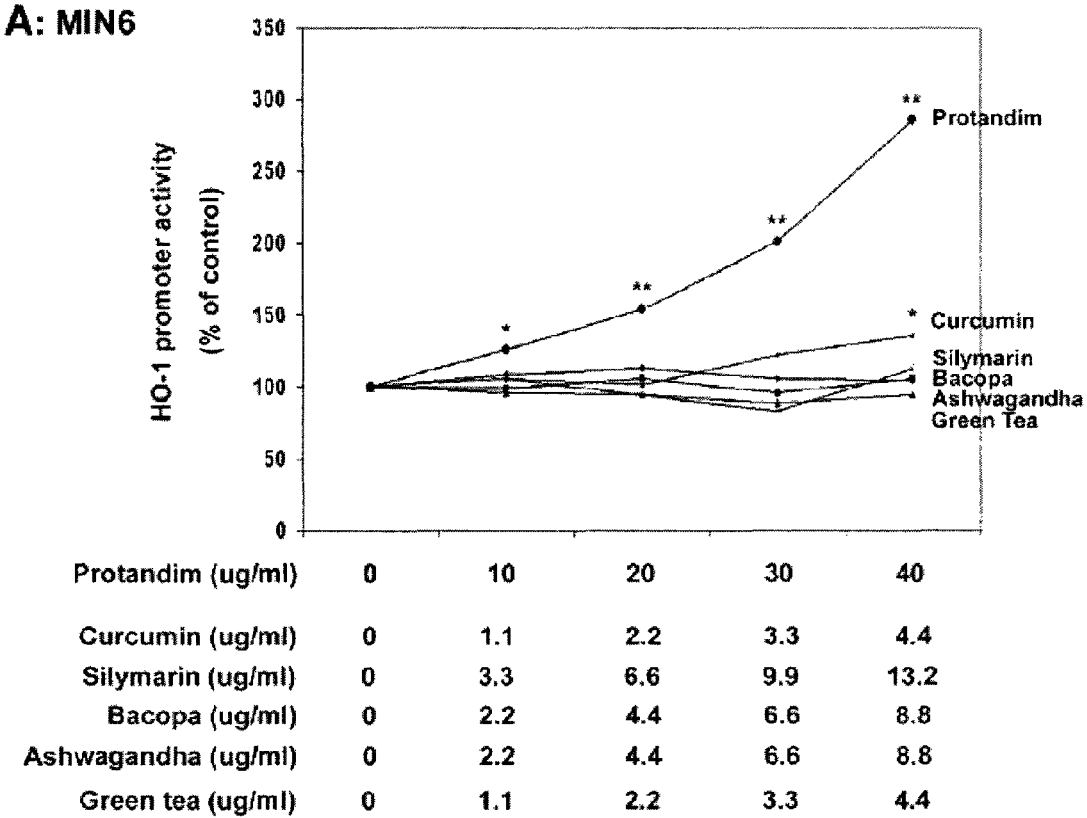
FIG. 22 shows a graph of the HO-1 promoter activity as a percentage of the control with (A) MIN6 and (B) SK-N-MC cells cultured in 12 dishes to 70% confluence were transfected with pHO15luc and a constitutively active Renilla luciferase (pRL-TK-Luc; to correct for transfection efficiency). Six hours after transfection, the cells were exposed to the alcohol-soluble fraction of Protandim® or its constituents at increasing concentrations for another 18 h. Cell lysates were prepared for the assay of luciferase activity. The results are the means of four independent observations. *p<0.01 and **p<0.001 vs untreated control.
Figure 22B:
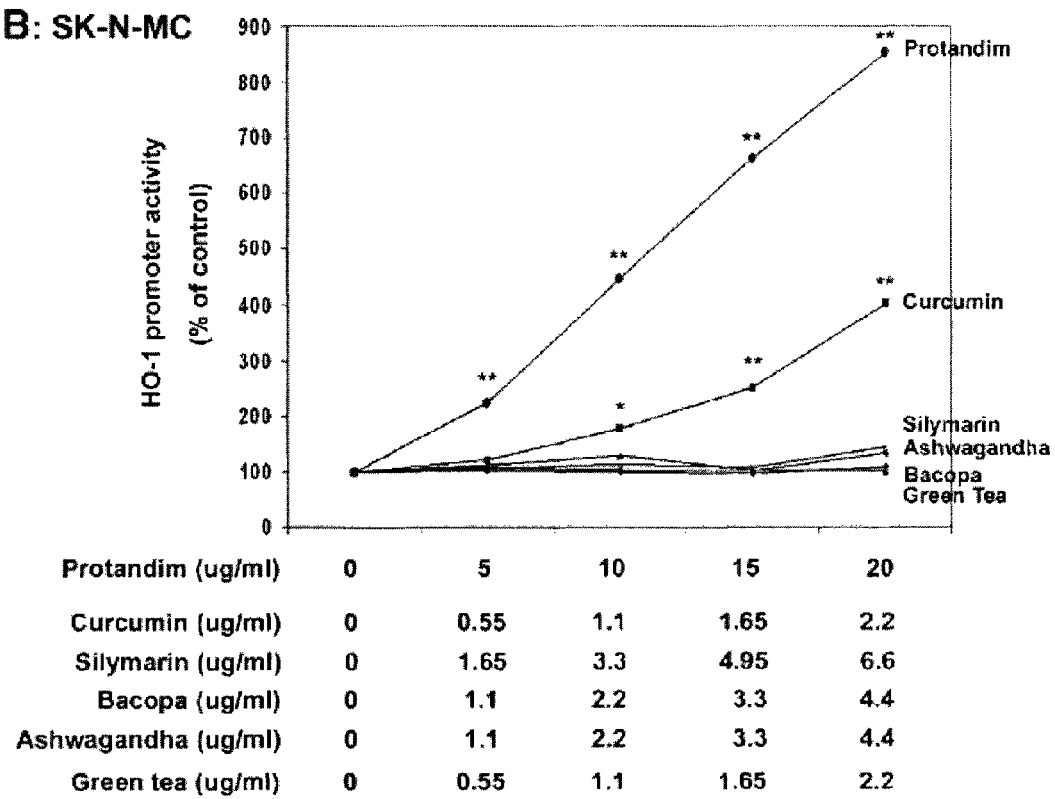

The luciferase reporter gene pHO15luc was generated by cloning a 15-kb promoter fragment of the mouse Ho-1 gene into the vector pSK1luc. FIG. 22 shows a graph of the HO-1 promoter activity as a percentage of the control with (A) MIN6 and (B) SK-N-MC cells. Cells cultured in 12 dishes to 70% confluence were transfected with pHO15luc and a constitutively active Renilla luciferase (pRL-TK-Luc; to correct for transfection efficiency). Six hours after transfection, the cells were exposed to the alcohol-soluble fraction of Protandim® or its constituents at increasing concentrations for another 18 h. Cell lysates were prepared for the assay of luciferase activity. The results are the means of four independent observations. *p<0.01 and **p<0.001 vs untreated control.

The results show that alcohol-soluble fraction of Protandim® induced the HO-1 promoter in a dose-dependent manner. A maximum induction of 3-fold was seen at 40 µg/ml in MIN6 cells, whereas an 8.5-fold increase was seen in SK-N-MC cells at a lower dose of 20 µg/ml (FIG. 22). Except for curcumin, the individual ingredients did not induce the HO-1 promoter significantly. Curcumin induced the HO-1 promoter by 36 and 300% in MIN6 and SK-N-MC cells, respectively, at concentrations present in the maximum dose of Protandim®. Therefore the effect of Protandim® on HO-1 promoter induction is greater than the sum of the effects of individual components, suggesting synergy among the phytochemicals.

Synergistic Induction of HO-1 at the Transcriptional Level by Protandim

Figure 23A:
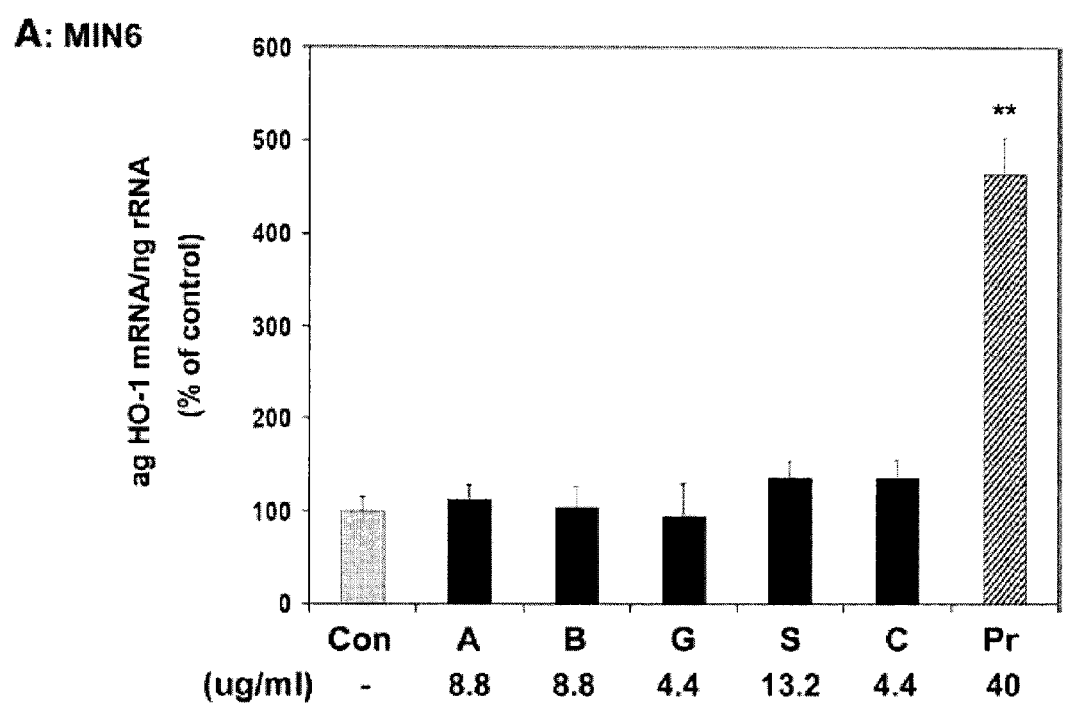
FIG. 23 shows graphs plotting the ratio of HO-1 mRNA (ag) to total ribosomal RNA (rRNA in ng) expressed as percentage of control with MIN6 cells (FIG. 22A) and with SK-N-MC cells (FIG. 22B). The results are the measns±standard error of four independent observations. *p<0.01 and **p<0.001 compared to the untreated control.
Figure 23B:
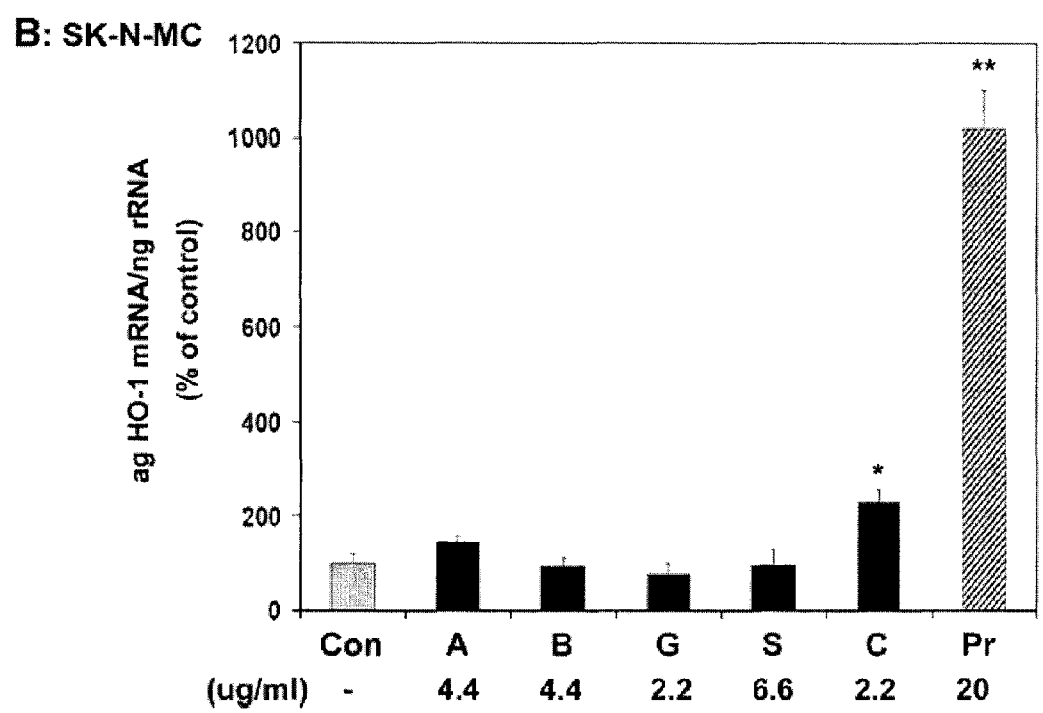

The expression of HO-1 at the mRNA level in MIN6 and SK-N-MC cells was observed after incubation in the presence of Protandim® or its components at the respective maximum doses used for HO-1 promoter assays as listed in Table 10 above. HO-1 mRNA levels were determined by real-time quantitative RT-PCR using a TaqMan probe and expressed in attograms (ag). FIG. 23 shows a graph plotting the ratio of HO-1 mRNA (ag) to total ribosomal RNA (rRNA in ng) expressed as percentage of control with MIN6 cells (FIG. 23A) and with SK-N-MC cells (FIG. 23B). The results are the means±standard error of four independent observations. *p<0.01 and **p<0.001 compared to the untreated control.

When the extracts of the individual components present in 40 µg/ml Protandim® were tested in MIN6 cells, ethanolic extracts of milk thistle and turmeric had a minimal effect on HO-1 induction (1.5-fold), whereas ethanolic extracts of the other three components (i.e., ashwagandha, Bacopa and green tea) treated individually failed to induce HO-1. However, treatment with the ethanolic extract of Protandim® extract increased expression of HO-1 by 4.6-fold (FIG. 23A). In SK-N-MC cells, the ethanolic extract of Protandim® effected a 10-fold induction and turmeric a 2-fold induction, whereas the other components present in Protandim® did not have any significant effect on HO-1 expression. (FIG. 23B). These observations are similar to the findings on the activation of the HO-1 promoter (FIG. 22).

Figure 24A:
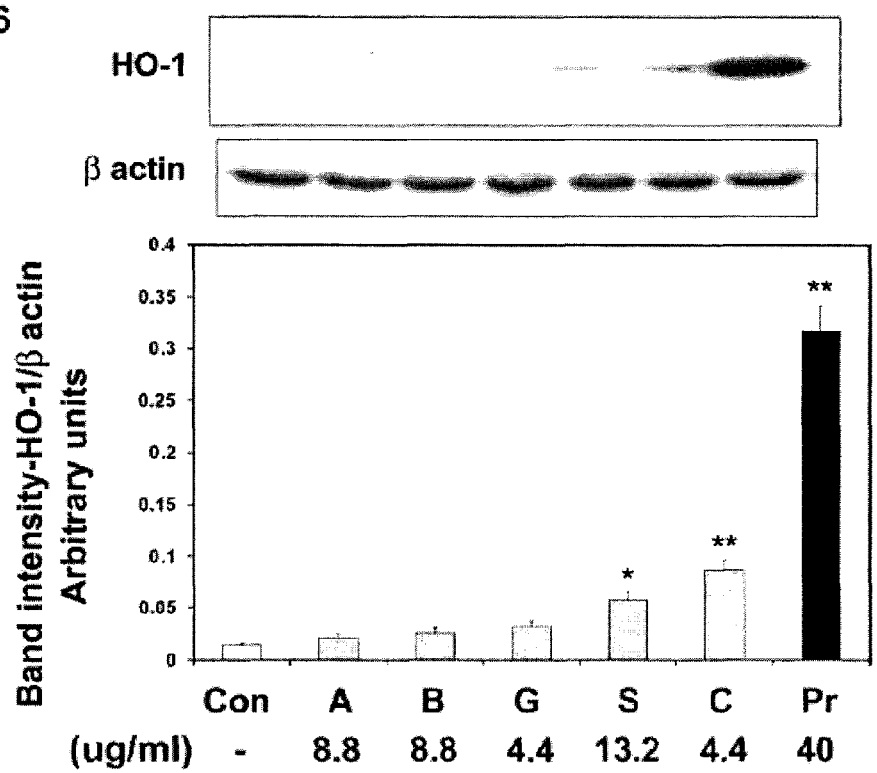
FIG. 24 shows western blots for HO-1 expression (upper panel), and β-actin control (middle panel), graph plotting band intensity of HO-1 standardized with β-actin in arbitrary units (lower panel) in MIN6 cells (FIG. 24A) and SK-N-MC cells (FIG. 24B). *p<0.01 and **p<0.001 compared to the untreated control.
Figure 24B:
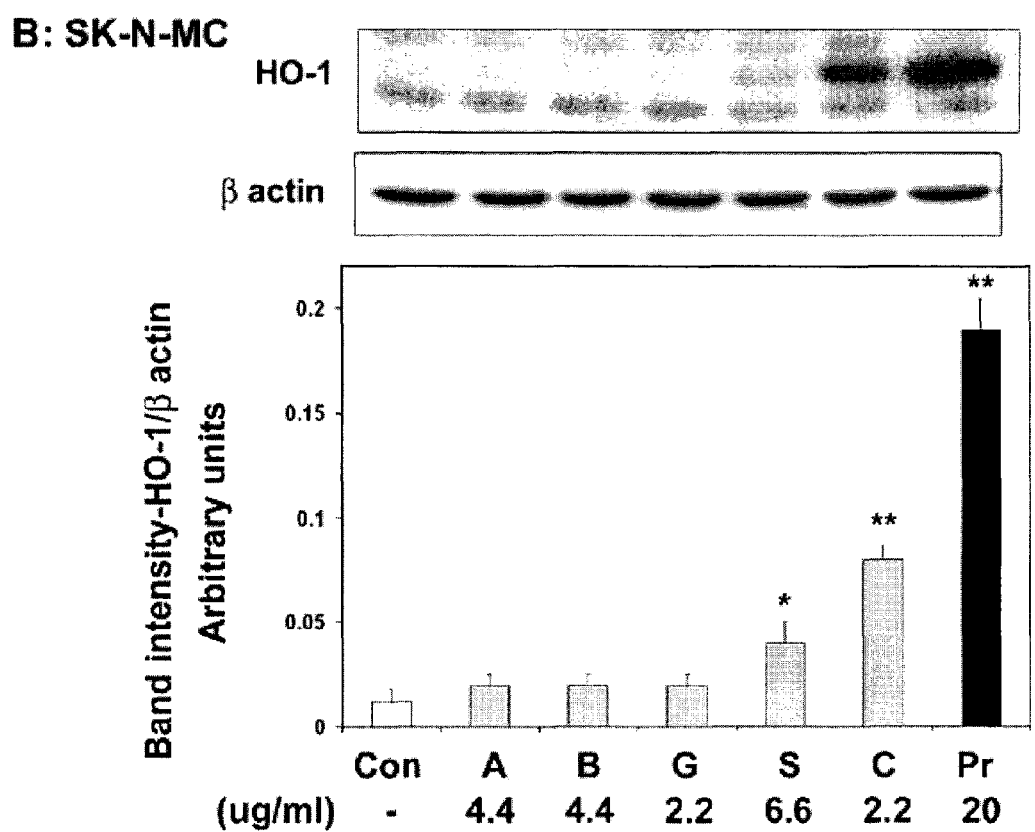

Synergy Among the Components of Protandim® in HO-1 Induction at the Protein Levels Protandim®-mediated induction of HO-1 at protein levels was examined by Western blot analysis after incubation of cells in the presence of the ethanolic extract of Protandim® or ethanolic extracts of its components at the respective maximum doses used for HO-1 promoter assays as listed in Table 10 above. Cell lysates were processed for Western blot analysis of HO-1, and the blots reprobed for β-actin. The intensities of bands were quantitated by scanning in a MultiImager using Quantity One software (Bio-Rad), and HO-1 expression was corrected for β-actin levels. FIG. 24 shows western blots for HO-1 expression (upper panel), and the β-actin control (middle panel), graph plotting band intensity of HO-1 standardized with β-actin in arbitrary units (lower panel) in MIN6 cells (FIG. 24A) and SK-N-MC cells (FIG. 24B). *p<0.01 and **p<0.001 compared to the untreated control.

In both MIN6 cells and SK-N-MC cells, HO-1 levels increased by 15- to 20-fold when the cells were incubated in the presence of the ethanolic extract of Protandim® at the respective optimal doses (FIG. 24). Among the individual components, silymarin (3- to 4-fold) and curcumin (6-fold) showed significant induction of HO-1. Overall, the extent of HO-1 induction by Protandim® was significantly greater than induction at the promoter and mRNA levels, especially in MIN6 cells. This observation suggests that Protandim® may improve the stability and translation of HO-1 mRNA. According to one embodiment, Protandim® reduces oxidative stress in cells and in neuroblastoma cells.

Protandim® Induces HO-1 through Nrf1

HO-1 is known to be induced by a number of transcription factors, including Nrf2, c-jun, NF-κB, and CREB. (Alam, J. et al., "Nrf2, a Cap'n'Collar transcription factor, regulates induction of the heme oxygenase-1 gene," J. Biol. Chem. 274:26071-26078; 1999; Gong, P. et al., Multiple basic-leucine zipper proteins regulate induction of the mouse heme oxygenase-1 gene by arsenite," Arch. Biochem. Biophys. 405:265-274; 2002; Hock, T. D. et al., "JunB and JunD regulate human heme oxygenase-1 gene expression in renal epithelial cells," J. Biol. Chem. 282:6875-6886; 2007). Several studies have reported that Nrf2 plays a major role through the E1 and E2 regions of AREs. To determine if the synergy among the components of Protandim® is due to the involvement of multiple transcription factors, the effects of deletion of the ARE site-containing E1 and E2 regions were tested.

Figure 25A:
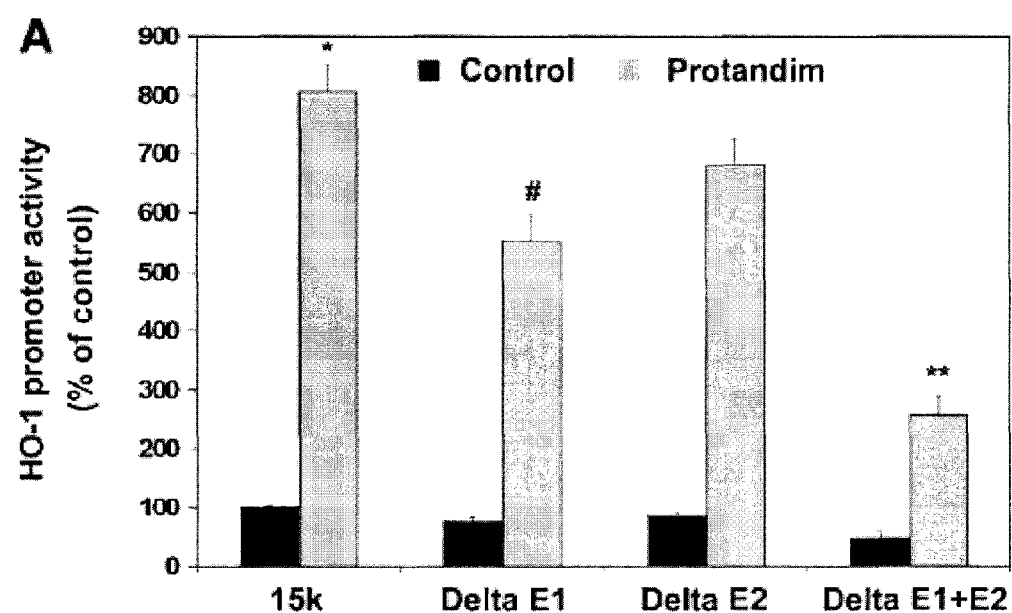
FIG. 25A shows a graph of HO-1 promoter activity as percentage of control as determined by the luciferase assay from the 15-kb promoter fragment, delta E1, delta E2, and double deletion fragment delta E1+delta E2. The results are means±SE of four independent observations. *p<0.001 vs untreated control; #p<0.01, **p<0.001 with respect to full-length promoter activation by Protandim®.

The plasmids ΔE1 and ΔE2 were obtained by deletion of a 600-bp SacI/SacI fragment and a 161-bp AflII/BsrBI fragment, respectively, from the 15-kb promoter fragment of the mouse HO-1 gene and were cloned into the luciferase reporter gene. SK-N-MC cells cultured in 12-well dishes to 70% confluence were transfected with the indicated HO-1 promoter constructs linked to firefly luciferase along with constitutively active *Renilla* luciferase using the LipofectAMINE 2000 reagent. After 6 h of transfection, the cells were exposed to 20 μg/ml ethanolic extract of Protandim® for another 18 h. Cell lysates were prepared and luciferase activities were measured. The ratios of the activities of firefly luciferase and *Renilla* luciferase were determined. FIG. 25A shows a graph of HO-1 promoter activity as percentage of control as determined from the luciferase assay of the 15-kb promoter fragment, delta E1, delta E2, and double deletion fragment delta E1+delta E2. The results are means±SE of four independent observations. $*p<0.001$ vs untreated control; $\#p<0.01$, $**p<0.001$ with respect to full-length promoter activation by Protandim®.

Figure 25B:
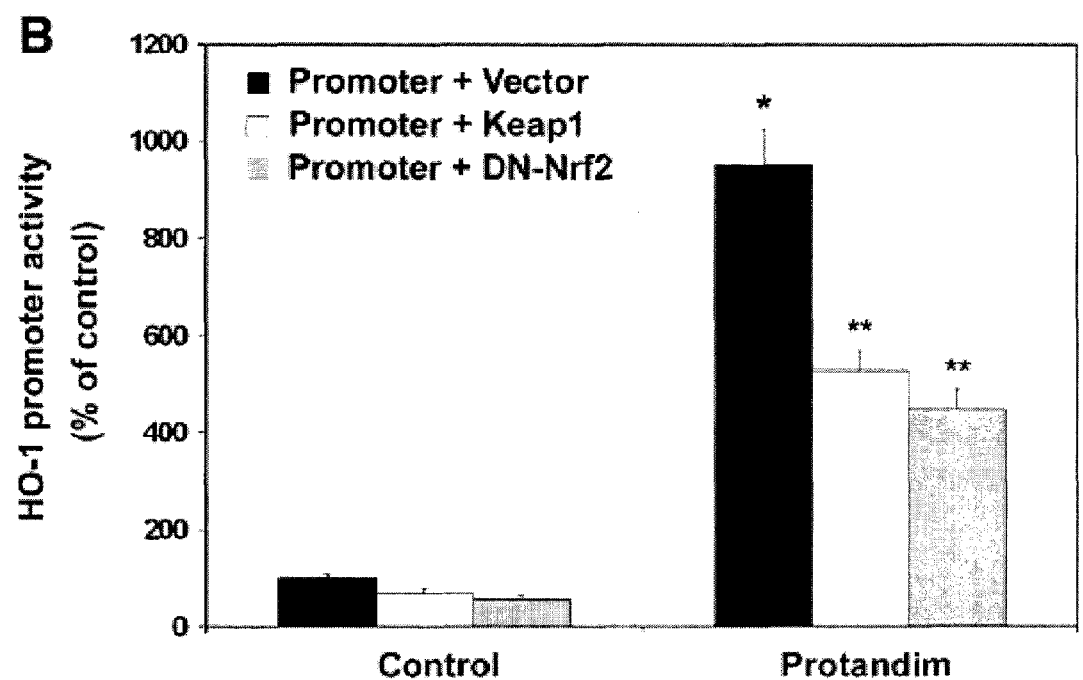
FIG. 25B shows a graph of HO-1 promoter activity as percentage of control as determined by the luciferase assay from (1) HO-1 promoter+vector; (2) HO-1 promoter+Keap1 expression construct; and (3) HO-1 promoter+dominant negative (DN) Nrf2 expression construct. The results are means±SE of four independent experiments. *p<0.001 vs untreated control; #p<0.001 with respect to vector control.

SK-N-MC cells were transfected with (1) the full-length promoter of HO-1 linked to the firefly luciferase reporter and vector (pEF); or (2) the promoter/reporter construct plus an expression construct for Keap1 or (3) the promoter/reporter construct plus a dominant negative Nrf2 expression construct. After 6 h of transfection, cells were exposed to 20 μg/ml ethanolic extract of Protandim® for 18 h. Cell lysates were prepared for the assay of luciferase activity. FIG. 25B shows a graph of HO-1 promoter activity as percentage of control as determined by the luciferase assay from (1) HO-1 promoter+vector; (2) HO-1 promoter+Keap 1 expression construct; and (3) HO-1 promoter+dominant negative (DN) Nrf2 expression construct. The results are means±SE of four independent experiments. $*p<0.001$ vs untreated control; $\#p<0.001$ with respect to vector control.

Deletion of E1 resulted in a 30% decrease (p<0.01) in the induction of the HO-1 promoter. (FIG. 25A). Deletion of E2 did not decrease Protandim®-mediated induction significantly. When both E1 and E2 were deleted, the activation of the HO-1 promoter by the ethanolic extract of Protandim® decreased by 70%. This study showed that the ethanolic extract of Protandim® induces HO-1 primarily through the AREs although the involvement of other response elements in the HO-1 promoter cannot be ruled out.

Next, to determine the role of the transcription factor Nrf2, which binds to ARE sites, a cotransfection approach was taken. Nrf2 is normally present in the cytoplasm bound to Keap1. Inducers of promoters with ARE sites dissociate Nrf2 from Keap1 and allow it to translocate to the nucleus. When HO-1-luc was cotransfected with a plasmid encoding Keap 1, Protandim®-induced HO-1 promoter activity decreased by 45% because overexpression of Keap1 can be expected to retain more of Nrf2 in the cytoplasm (FIG. 25B). Overexpression of dominant negative Nrf2 with a deleted transactivation domain also decreased HO-1 promoter activation by 53%. These observations showed that Protandim®-mediated HO-1 induction proceeds primarily through Nrf2.

Nuclear Translocalization of Nrf2 by Protandim® in SK-N-MC Cells

Nuclear localization of Nrf2 was tested with immunofluorescent staining after treatment of SK-N-MC cells with the ethanolic extract of Protandim®. SK-N-MC cells cultured on coverslips were exposed to 20 μg/ml Protandim® ethanolic extract. After 6 h, cells were fixed in 4% paraformaldehyde, permeabilized, and immunostained for active Nrf2 (Cy3; red). The nuclei were stained with DAPI (blue). Images were examined by fluorescence microscopy.

Figure 26:
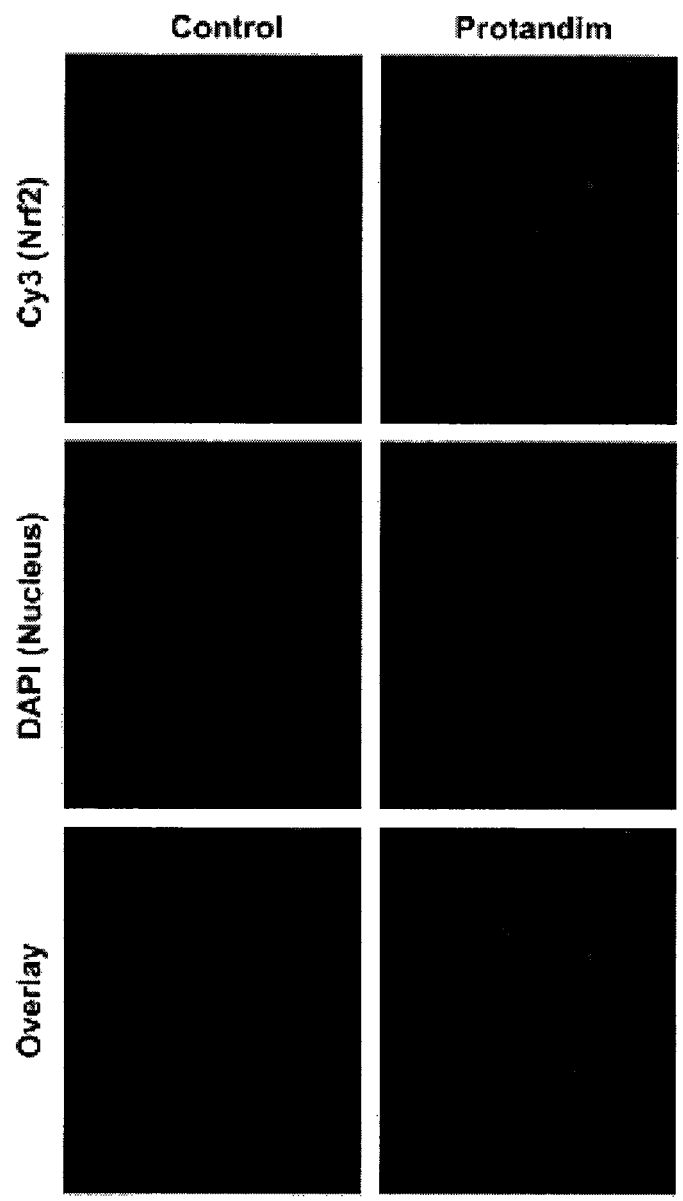
FIG. 26 shows fluorescence microscope images of untreated control and Protandim-treated cells showing Nrf2 stained with Cy3 (red) and nuclei stained with DAPI (blue). The merge of Cy3 and DAPI is shown as an overlay. The images presented are representative of multiple fields from three independent experiments.

FIG. 26 shows fluorescence microscope images of untreated control and Protandim®-treated cells showing Nrf2 stained with Cy3 (red) and nuclei stained with DAPI (blue). The merge of Cy3 and DAPI is shown as an overlay. The images presented are representative of multiple fields from three independent experiments.

Nrf2 stained with Cy3 was present mostly in the cytoplasm of untreated cells. Culture of these cells with the alcohol soluble fraction of Protandim® (20 μg/ml) for 6 h resulted in the appearance of Cy3 signal mostly in the nucleus. The red fluorescent stain of Nrf2 overlapped with DAPI stain (blue) for nucleus, suggesting nuclear localization. This observation, along with the findings from the HO-1 promoter assay with ARE-site-deleted constructs (FIG. 25A) and the cotransfection experiments (FIG. 25B), suggests that the components of Protandim® act mainly through the transcription factor Nrf2. Similar observations have been previously made with curcumin, an essential component of Protandim®, in MIN6 cells as described in Pugazhenthi, S. et al., "Regulation of heme oxygenase-1 expression by demethoxy curcuminoids through Nrf2 by a PI3-kinase/Akt-mediated pathway in mouse beta cells," Am. J. Physiol. Endocrinol. Metab. 293: 645-655; 2007. These findings also suggest that the synergistic effect of Protandim® components is not likely to be primarily through the involvement of multiple transcription factors.

Multiple Signaling Pathways are Involved in the Protandim®-Mediated Induction of HO-1

Figure 27A:
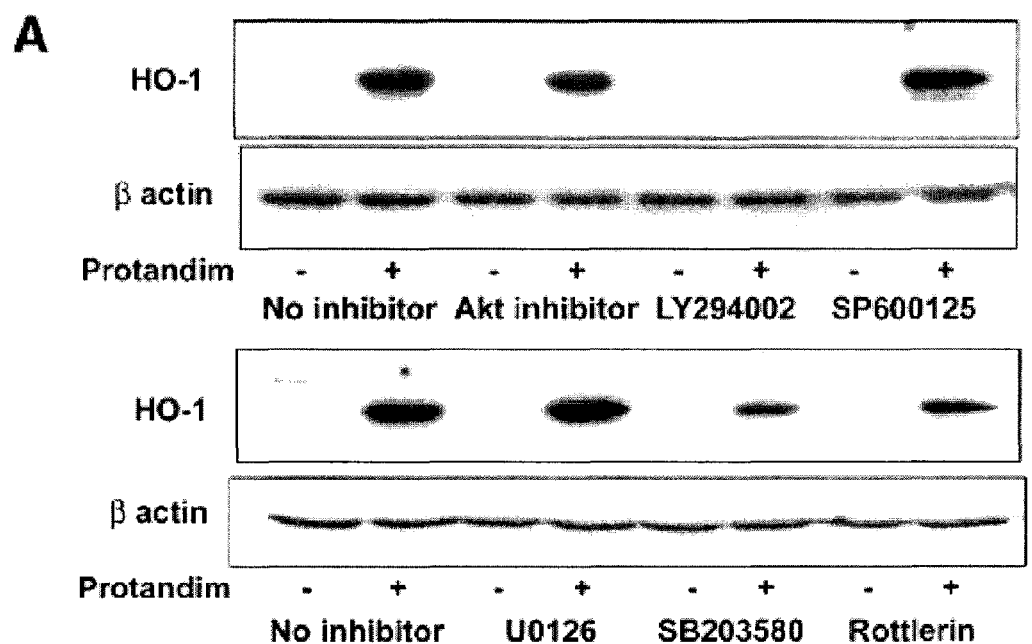
FIG. 27A shows a representative of four western blots for each inhibitor (Akt inhibitor IV, LY294002, rottlerin, U0126, SB203580, or SP600125) and control.
Figure 27B:
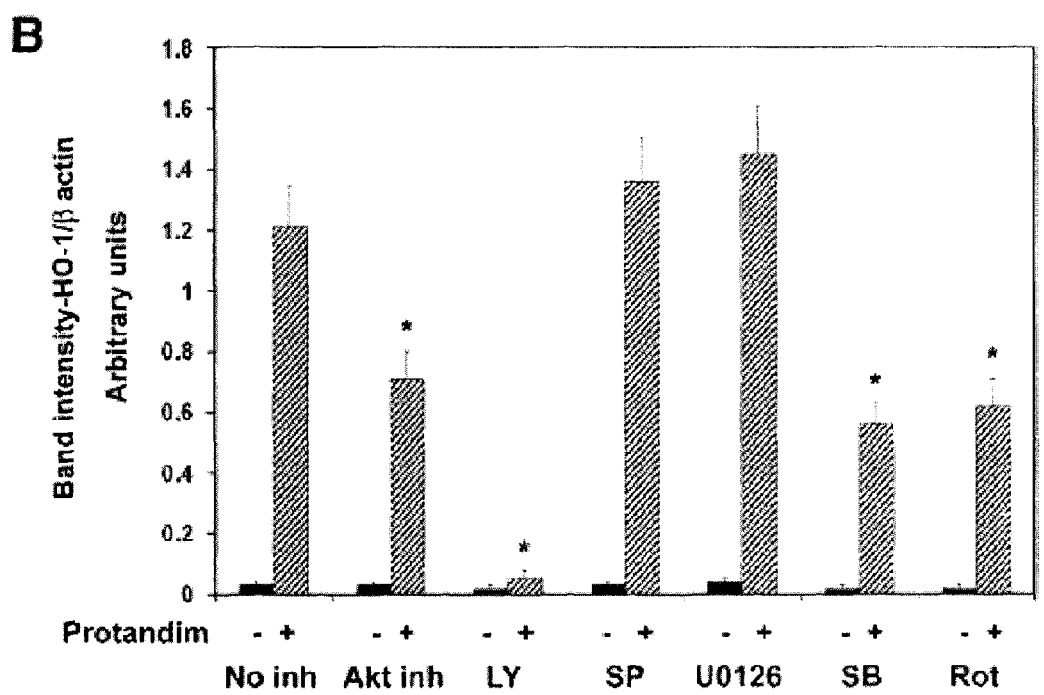
FIG. 27B shows a graph of band intensity of HO-1 corrected for β-actin expression for each inhibitor and control. *p<0.001 compared to untreated control. #p<0.001 with respect to Protandim-treated cells in the absence of inhibitors.

To identify the signaling pathway(s) involved in HO-1 promoter induction by Protandim®, different pharmacological inhibitors that specifically block each of the following pathways were used: 5-(2-benzothiazolyl)-3-ethyl-2-[2-(methylphenylamino) ethenyl]-1-phenyl-1H-benzimidazolium iodide (Akt inhibitor IV) for Akt, LY294002 for PI3-kinase, SP600125 for JNK, U0126 for MEK/ERK, SB203580 for p38MAPK, and rottlerin for PKCδ. SK-N-MC cells were preincubated in the presence of 250 nM Akt inhibitor IV, 30 μM LY294002, 1 μM rottlerin, 10 μM U0126, 20 μM SB203580, or 20 μM SP600125 for 30 min followed by exposure to 20 μg/ml Protandim® for 24 h. Cell lysates were electrophoresed and immunoblotted for HO-1. The blots were then reprobed with the antibody for β-actin. FIG. 27A shows a representative of four western blots for each inhibitor and control. The intensities of the bands were quantified by densitometry using Fluor-S MultiImager and Quantity One software from Bio-Rad. HO-1 levels were corrected for β-actin expression. FIG. 27B shows a graph of band intensity of HO-1 corrected for β-actin expression for each inhibitor and control. *$p<0.001$ compared to untreated control. #$p<0.001$ with respect to Protandim®-treated cells in the absence of inhibitors.

Involvement of PI3-kinase/Akt was suggested by a significant ($p<0.001$) decrease in the Protandim®-induced increase in HO-1 protein levels in the presence of LY294002 and Akt inhibitor IV (FIG. 27). Curcumin and its analogues were previously repoted to induce HO-1 by activating this pathway. (Pugazhenthi, S. et al., "Regulation of heme oxygenase-1 expression by demethoxy curcuminoids through Nrf2 by a PI3-kinase/Akt-mediated pathway in mouse beta cells," Am. J. Physiol. Endocrinol. Metab. 293:645-655; 2007). The results of that study showed that p38MAPK and PKCδ were not involved in HO-1 induction by curcumin, whereas the Protandim®-mediated increase in HO-1 expression decreased by 50% in the presence of SB203580, an inhibitor of p38MAPK, and rottlerin, an inhibitor of PKCδ. Therefore, the components of Protandim® other than turmeric containing curcumin (i.e., *Bacopa*, milk thistle, ashwagandha, and green tea) could be contributing to HO-1 induction through the p38MAPK and PKCδ pathways. No significant effect on HO-1 induction by Protandim® was observed in the presence of U0126 or SP600125, suggesting that MEK/ERK and JNK may not play a significant role in Protandim®-stimulated HO-1 expression. These observations suggest that the synergy among the components of Protandim® in the induction of HO-1 through Nrf2 could be due to the involvement of multiple signaling pathways.

Elevation of Glutathione Content in Protandim®-Treated Cells

Figure 28A:
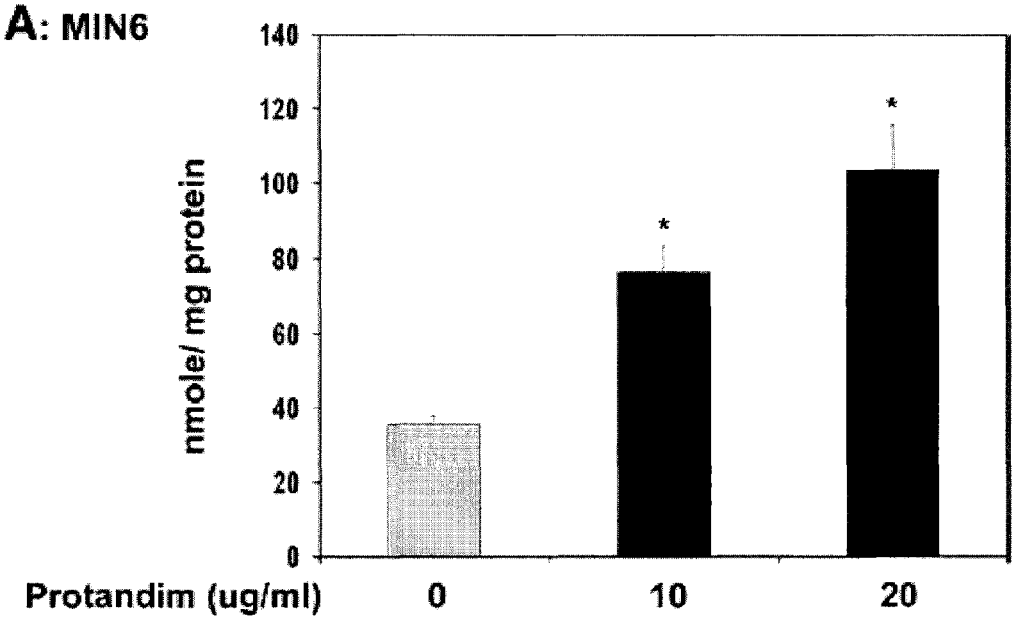
FIG. 28 shows graphs of glutathione content (nmole/mg protein) in MIN cells (FIG. 28A) and in SK-N-MC cells (FIG. 28B). *p<0.001 compared to untreated control.
Figure 28B:
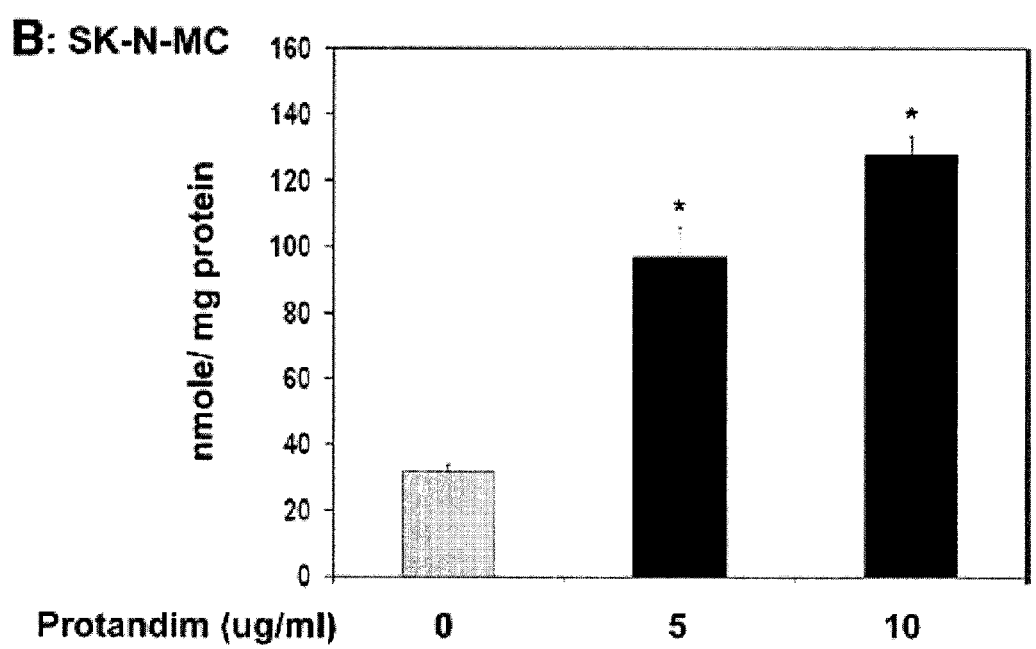

To determine the functional outcome of induction of an antioxidant enzyme by Protandim®, the cellular content of glutathione was examined. SK-N-MC cells cultured in 100-mm dishes to 70% confluence were exposed to the indicated concentrations of ethanolic extract of Protandim® for 24 h. Cell lysates were prepared for the assay of total glutathione. FIG. 28 shows graphs of glutathione content (nmole/mg protein) in MIN cells (FIG. 28A) and in SK-N-MC cells (FIG. 28B). *$p<0.001$ compared to untreated control.

This experimeny showed significant ($p<0.001$) increases in the levels of total glutathione after exposure to ethanolic extract of Protandim®. (FIG. 28). In MIN6 cells, a two-to threefold increase was observed after treatment with 10-20 μg/ml Protandim® ethanolic extract. SK-N-MC cells showed higher sensitivity to Protandim® ethanolic extract as in the case of HO-1. Elevation of glutathione content by two- to fourfold was observed in the presence of 5-10 μg/ml concentrations of the ethanolic extract of Protandim®.

Example 6

Synergistic Effect of Protandim® on Induction of Heme Oxygenase-1 (Ho-1) Using Sh-FY-5Y Cells The ability of Protandim® to activate the heme oxygenase (HO-1) promoter as a representative of the family of phase 2 enzymes was evaluated in an in vitro system of cultured human SH-FY-5Y cells transiently transfected with a genetic construct consisting of the human HO-1 promoter driving expression of Firefly luciferase. Transfection efficiency was controlled by simultaneous co-transfection with a construct constitutively expressing *Renilla* luciferase. The two luciferases may be differentially assayed in the same cell lysate by varying assay conditions. The HO-1 promoter/reporter construct was transiently transfected into human SH-FY-5Y cells and exposed to increasing concentrations of Protandim® (0, 10 μg, 20 μg, 30 μg, and 40 μg) for 16 hours. The Protandim® extract was prepared by mixing 100 mg of Protandim® powder with 5 ml of 95% ethanol in the cold for 30 min, then centrifuging at 5000 rpm to remove the undissolved solids.

Figure 29:
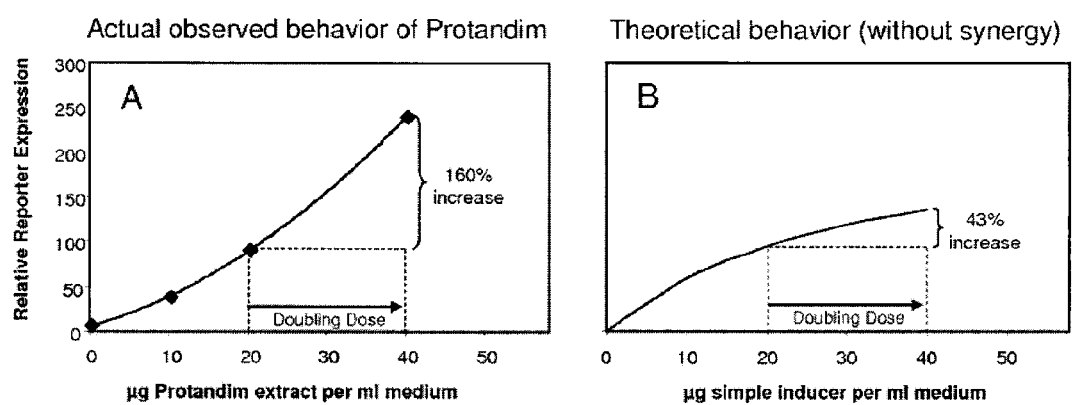
FIG. 29A shows dose-response curves evidencing synergistic induction of the HO-1 promoter compared to the expected theoretical behavior for non-synergistic induction.
FIG. 29B shows a theoretical rectangular hyperbolic curve with the same level of expression at the 20 µg/ml dose expected in the absence of any synergistic or cooperative effects.

FIG. 29A shows dose-response curves evidencing synergistic induction of the HO-1 promoter compared to the expected theoretical behavior for non-synergistic induction. FIG. 29A shows the HO-1 driven expression of the reporter gene at three concentrations of a 95% ethanol extract of Protandim®. The abscissa reflects the amount of Protandim® extracted per ml of culture medium, and the values are in the range of expected values for humans dosed orally with Protandim® at one 675 mg caplet per day. The presence of synergy is suggested by simple inspection of the plot, as evidenced by the upward curvature, and a greater-than-linear response to increases in concentration.

FIG. 29B shows a theoretical rectangular hyperbolic curve with the same level of expression at the 20 μg/ml dose expected in the absence of any synergistic or cooperative effects. If doubling the dosage produces a less-than-100% increase, the behavior is indicative of rectangular hyperbolic saturation. Doubling the concentration of Protandim® extract from 20 to 40 μg/ml caused a greater-than-double increase of reporter gene expression to 2.6-fold, whereas doubling the concentration of a non-synergistic inducer would increase reporter gene expression to only 1.43-fold.

Evidence for synergistic interactions among the Protandim® components is further suggested when the data are analyzed by the Median-Effect Plot described in Chou, T. C., "Theoretical basis, experimental design, and computerized simulation of synergism and antagonism in drug combination studies," Pharmacol. Rev. 58, pp. 621-681 (2006), the entire disclosure of which is incorporated herein by reference. The median-effect equation describes dose-effect relationships, where D is the dose (or concentration) of a drug (Protandim® in this case), $f_a$ is the fraction affected by D (i.e., percentage of maximal induction of the HO-1 promoter), and $f_u$ is the fraction unaffected (i.e., $f_u=1-f_a$). $D_m$ is the median-effect dose (e.g., $ED_{50}$) that induces the system under study 50%, and m is the coefficient signifying the shape of the dose-effect relationship, where m=1, 1, and <1 indicate hyperbolic, sigmoidal (synergistic), and flat sigmoidal (antagonistic) dose-effect curves, respectively. The median-effect equation is given here in a logarithmic form for plotting purposes in the form of the classic straight-line equation, y=mx+b: $\log(f_a/f_u)$=m log (D)−m $\log(D_m)$.

Figure 30:
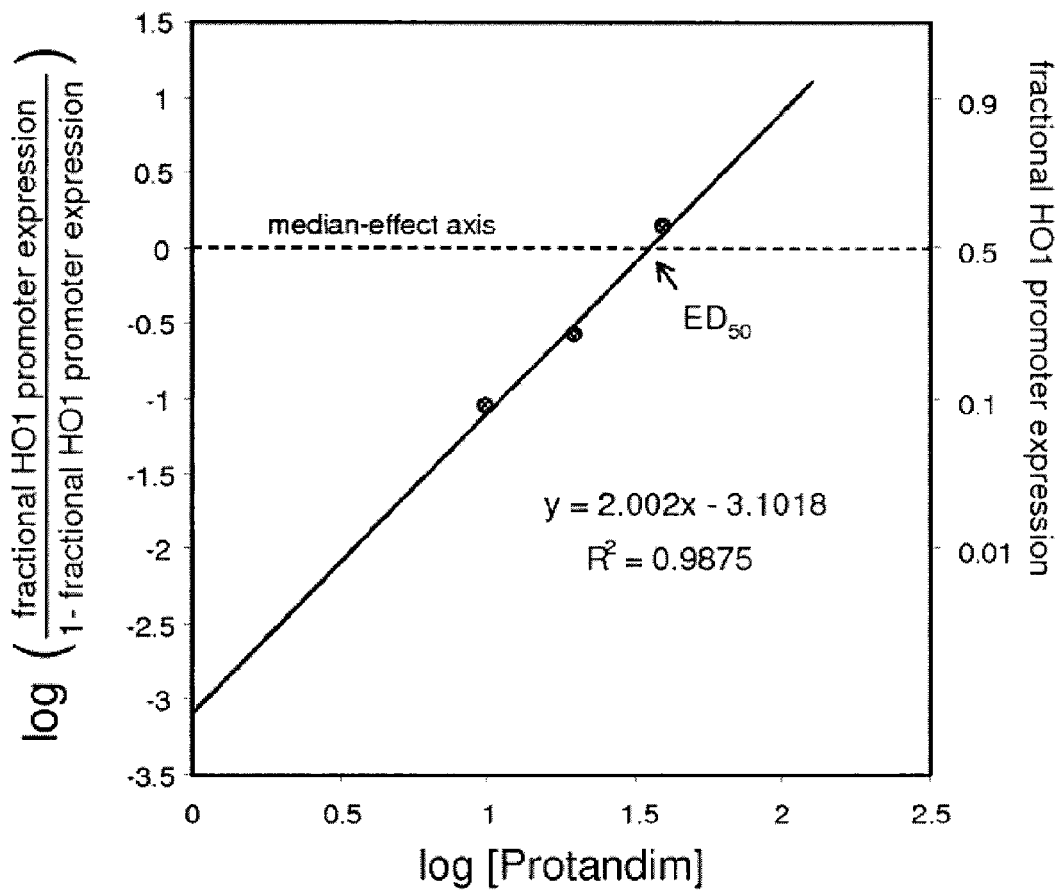
FIG. 30 shows the results of the Chou median effect plot for Protandim® concentrations (20 µg, 30 and 40 µg).

FIG. 30 shows the results of the Chou median effect plot for three Protandim® concentrations (20 μg, 30 μg, and 40 μg). The conformity of the data to the median-effect plot of the mass-action law can be manifested by the linear correlation coefficient (r) of the median-effect plot in which r=1 indicates perfect conformity. The correlation coefficient for our data is 0.9875. The use of the median-effect principle for a dose-effect analysis is a distinct departure from the conventional statistical approach in which an empirical curve is drawn to fit the scattering data points. However, in Chou's approach, the scattering data points are used to fit the median-effect principle of the mass-action law. The slope of the line is 2.0, indicating synergy among the ingredients in the composition Protandim®. A slope of 1 would indicate no synergy.

Figure 31:
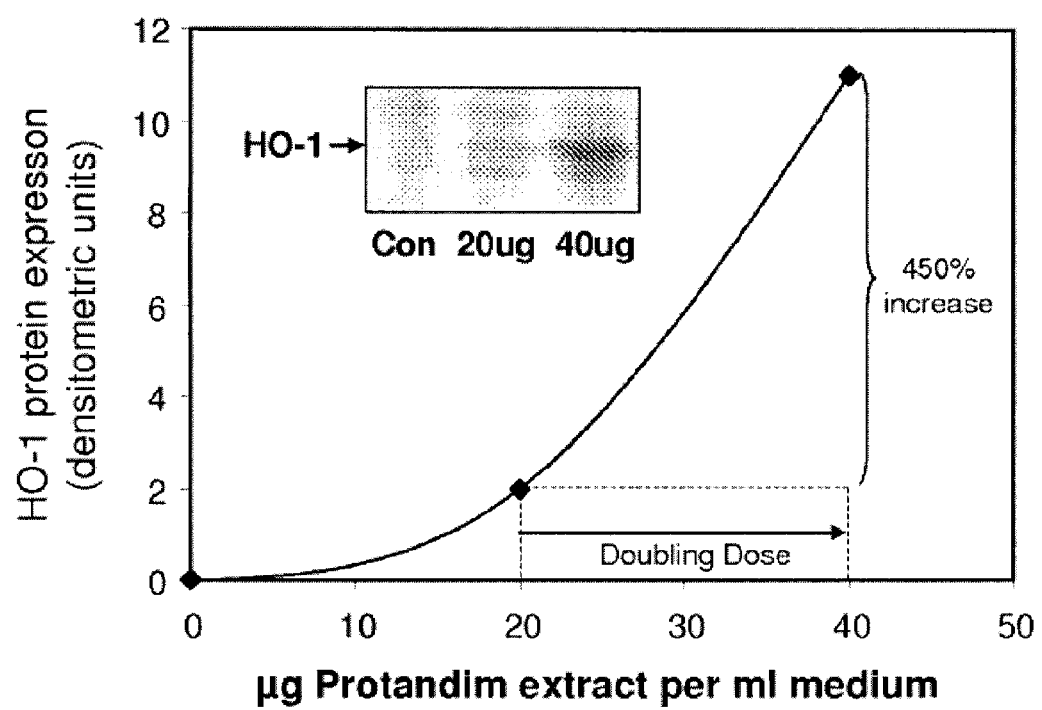
FIG. 31 shows dose response evidence for synergistic induction of HO-1 gene expression by Protandim® in human cell line SH-FY-5Y as measured by HO-1 expressed protein level determined by Western blots. The inset shows the Western blot results.

The ability of Protandim® to synergistically induce HO-1 was also shown by observing the induction of the endogenous HO-1 gene in SH-FY-5Y cells, with immunological detection of the natural gene product by Western analysis. SH-FY-5Y cells were exposed to increasing concentrations of Protandim® (0, 10 µg, 20 µg, 30 µg, and 40 µg) for 16 hours. HO-1 expression was determined by Western blotting and densitometric scanning. FIG. 31 shows dose response evidence for synergistic induction of HO-1 gene expression by Protandim® in human cell line SH-FY-5Y as measured by HO-1 expressed protein level determined by Western blots. The inset shows the Western blot results. This experiment showed that doubling the Protandim® dose produced a concentration of HO-1 equal to 5.5 times that at the lower dose (a 450% increase).

Figure 32:
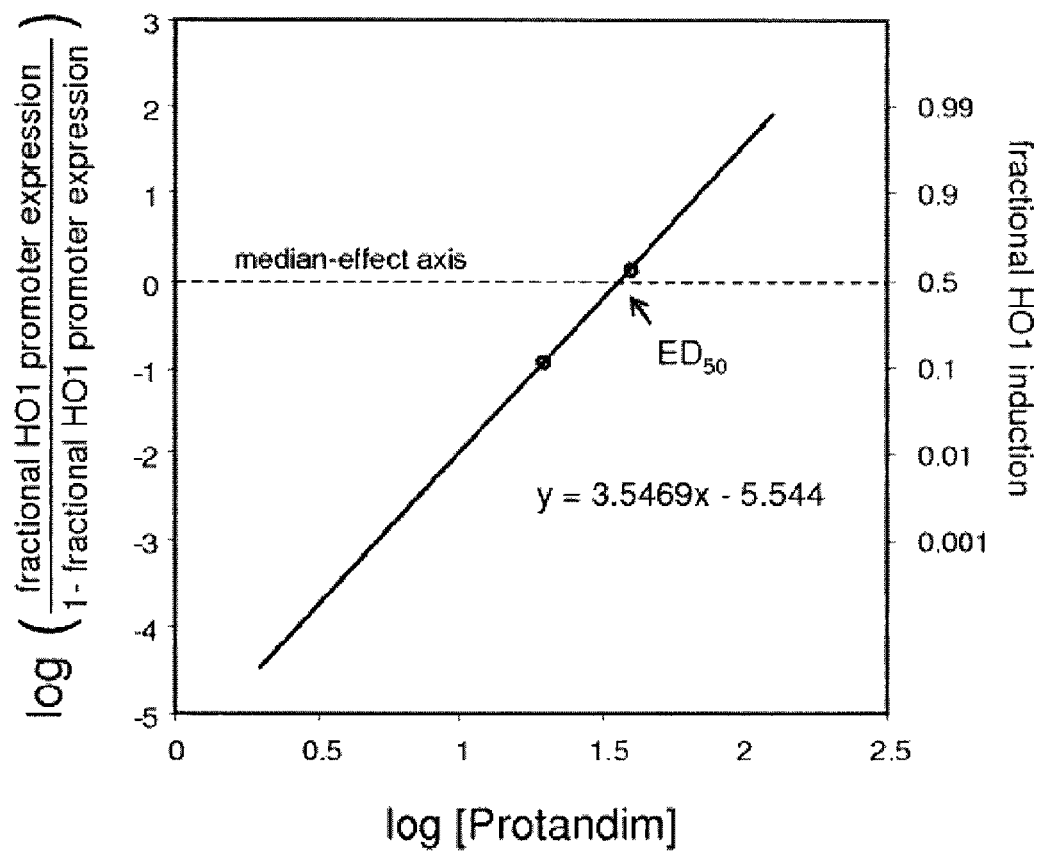
FIG. 32 shows a median-effect plot showing the ability of Protandim® to synergistically induce the expression of the HO-1 gene in a human SH-FY-5Y cells after 16 hours. The expression was relative to constitutively expressed *Renilla* luciferase, which was co-transfected to the control for transfection efficiency.

The Chou median-effect plot allows for the determination of synergy with the minimum of two experimental dose observations, unlike empirically determined analyses. Accordingly, the data in FIG. 31 may be plotted by the median-effect method. FIG. 32 shows a median-effect plot showing the ability of Protandim® to synergistically induce the expression of the HO-1 gene in a human SH-FY-5Y cells after 16 hours. The expression was relative to constitutively expressed *Renilla* luciferase, which was co-transfected to the control for transfection efficiency. FIG. 32 shows evidence of synergy (slope=3.55) when Protandim® acts on the HO-1 promoter in its natural context, driving the endogenous HO-1 gene.

Example 7

Bioassay for Nrf2 Activation

The assay for Nrf2 activation is based on the AREc32 cell line, developed by Dr. C. R. Wolf and colleagues of the University of Dundee, Scotland, as described in Wang, X. J. et al., "Generation of a stable antioxidant response element-driven reporter gene cell line and its use to show redoxdependent activation of Nrf2 by cancer chemotherapeutic agents," Cancer Res. 66, 10983-10994 (2006); Hybertson, B. M. et al., "Oxidative stress in health and disease: the therapeutic potential of Nrf2 activation," Molecular Aspects of Medicine, 32: 234-246 (2011), the entire disclosure of each of which is incorporated herein by reference. The AREc32 cell line is a stable transfectant derived from the MCF7 human breast cancer cell line. It contains a promoter with eight copies of the rat glutathione-S-transferase-A2 Antioxidant Response Element (ARE) and the SV40 promoter sequence upstream of a firefly luciferase reporter gene.

Briefly, AREc32 cells were grown in Opti-MEM (GIBCO, Carlsbad, Calif.) supplemented with 4% fetal bovine serum (FBS, GIBCO) and 1% Antibiotic-Antimycotic (GIBCO) at 37° C. and in a 10% CO 2-supplemented air atmosphere. The cells were seeded at 1% to 5% of confluent cell density in T75 tissue culture flasks and cultivated until they approached confluence. The medium was aspirated off and the adherent cells trypsinized with 1 ml of 1× Trypsin-EDTA solution (GIBCO) for 10 min. Ten milliliters of medium was added to the flask and the cells transferred to a 50 ml centrifuge tube and centrifuged at 1000 rpm for 5 min at room temperature. Cells were washed once with 10 ml of medium, then resuspended in 10 ml of medium. Cells were counted using a hemocytometer and diluted to a concentration of 50,000 cells/ml. Four hundred microliters of this cell suspension was seeded into each well of a 24-well plate (i.e. 20,000 cells/well). Seeded plates were then returned to the incubator for 24 h.

After 18-24 h the cells were reattached and growing, and ready for treatment with samples with putative Nrf2 activating activity. The test samples were added to the wells in an appropriate concentration range, in volumes ranging from 1 to 10 µl/well to about 20,000 cells/well: ethanolic extracts of Protandim® (0, 20 µg/ml, 40 µg/ml, 60 µg/ml and 80 µg/ml); Bardoxolone (0, 0.1 µM, 0.2 µM, 0.3 µM, 0.4 µM, 0.5 µM); dimethylfumarate (0, 20 µM, 40 µM, 60 µM, 80 µM and 100 µM); and sulforaphane (0, 2 µM, 4 µM, 6 µM, 8 µM, 10 µM). Vehicles used were aqueous or organic solvents such as ethanol or DMSO, and appropriate vehicle controls were included. The cells were then returned to the incubator for 18 h. All operations up to this point must be conducted under sterile conditions.

After 24 h the cells were checked under the microscope for any abnormalities or detachment. The medium was aspirated and the cells were washed with phosphate buffered saline, pH 7.4 (100 µl/well). Following aspiration of the wash solution, the cells were lysed by application of 0.1 M potassium phosphate buffer, pH 7.8, containing 1% Triton X-100, 2 mM dithiothreitol, 2 mM EDTA, 10% glycerol and 3.5 mM sodium pyrophosphate (100 µl/well). The plate was incubated at 4° C. for 20 min. Lysate (20 µl from each well in a new 12×75 mm glass test tube) was assayed for luciferase activity using a Monolight 3010 autoinject luminometer (Analytical Luminescence Laboratory, Ann Arbor, Mich.), automatically injecting 50 of Luciferase Assay Buffer after background measurement. Luciferase Assay Buffer was prepared by mixing 9 ml of Solution A (15 mM Tricine, pH 7.8, containing 1.5 mM ATP, 7.5 mM MgSO 4, and 5 mM dithiothreitol) with 1 ml of Solution B 10 mM D-luciferin). After a 4 delay following injection, luminescence was measured for 10 s. Relative Light Units (RLU) were recorded for the contents of each well. Fold Induction (FI) of luciferase activity was calculated by dividing the RLU obtained for the test well by the average RLU obtained for control wells (which received no putative Nrf2 activator). Each assay or control was performed in duplicate. Parameters noted were the concentration of test substance providing maximal fold induction of luciferase ($C_{max}$), and the maximal fold induction observed ($FI_{max}$).

Figure 33:
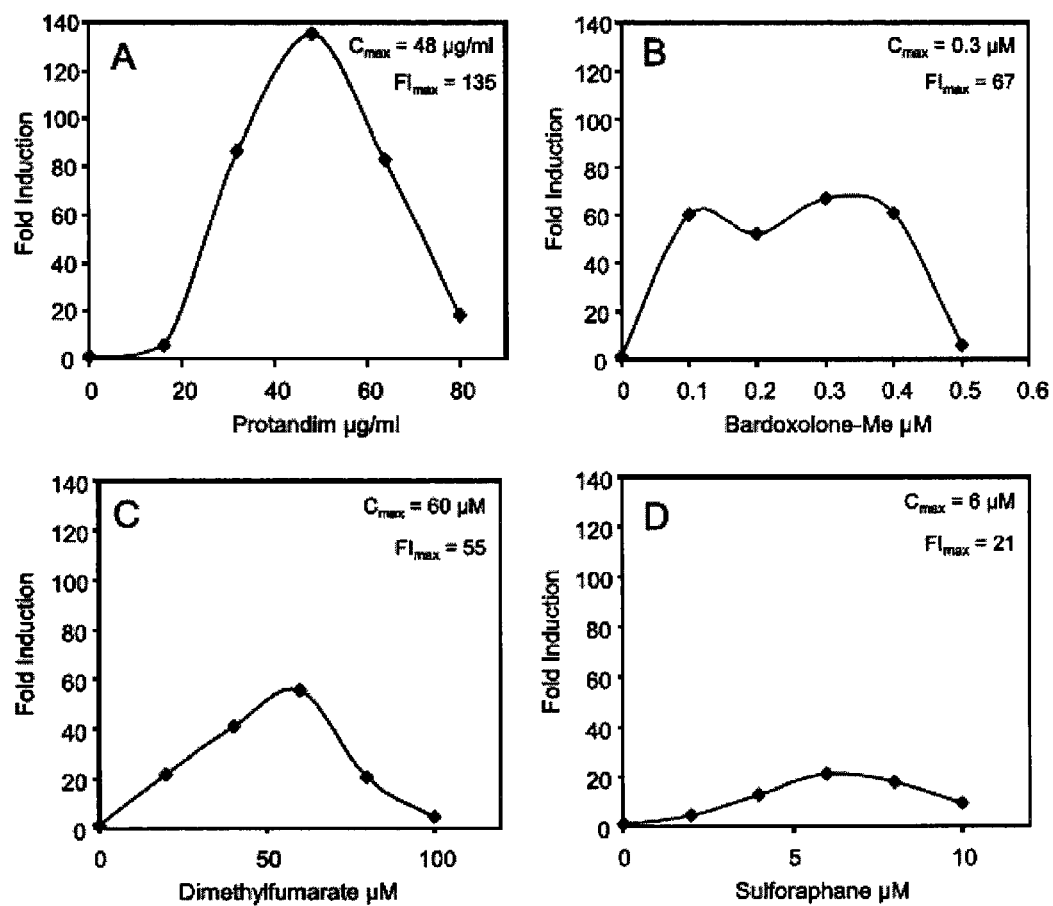
FIG. 33 shows plots of Nrf2 fold-induction (FI) vs. concentration of Nrf2 activator samples: Protandim® (FIG. 33A), bardoxolone (FIG. 33B), dimethylfumarate (FIG. 33C), and sulforaphane (FIG. 33D) as measured with the AREc32 based bioassay.

In these cells, luciferase activity was increased up to 50-fold following treatment with 50 µmol/L tert-butyl-hydroquinone. Luciferase activity is increased up to 100-fold by Protandim® at 30 µg/ml. Each assay or control was performed in duplicate. Parameters noted were the concentration of test substance providing maximal fold induction of luciferase ($C_{max}$), and the maximal fold induction observed ($FI_{max}$). FIG. 33 provides a comparison using the AREc32-based bioassay for Nrf2 activation among Protandim®, sulforaphane, bardoxolone methyl, and dimethyl fumarate. Sulforaphane is often considered a "gold standard" among naturally-occurring Nrf2 activators. (Agyeman et al., "Trascrimptomic and proteomic profiling of KEAP 1 disrupted and sulforaphane-treated human breast epithelial cells reveals common expression profiles," Breast Cancer Res. Treat., 132 (1): 175-187 (2011), the entire disclosure of which is incorporated herein by reference). FIG. 33 shows plots of Nrf2 fold-induction (FI) vs. concentration of Nrf2 activator samples: Protandim® (FIG. 33A), bardoxolone (FIG. 33B), dimethylfumarate (FIG. 33C), and sulforaphane (FIG. 33D) as measured with the AREc32 based bioassay. The greatest $FI_{max}$ was observed with the ethanolic extract of Protandim® at 135-fold, followed by bardoxolone methyl at 67-fold, dimethyl fumarate at 55-fold, and sulforaphane at 21-fold. Of the three pure compounds tested, bardoxolone methyl showed the lowest $C_{max}$ 0.3 µM, with sulforaphane at 6 and dimethyl fumarate 60 The ethanolic extract of Protandim®, a mixture of five active ingredients, showed $C_{max}$ of 48 µg/ml. This concentration of Protandim® would contain approximately 26 µM silybinin, 13.6 µM curcumin, 5 µM EGCG, 0.07 µM with aferin A, and 5 µM bacopasides. Bardoxolone methyl appeared to produce a biphasic induction, producing near maximal FI over a range of concentrations from less than 40 nM to 0.4

Example 8

Screening for Nrf2 Inducing Active Ingredient in Botanical Extracts

Figure 34:
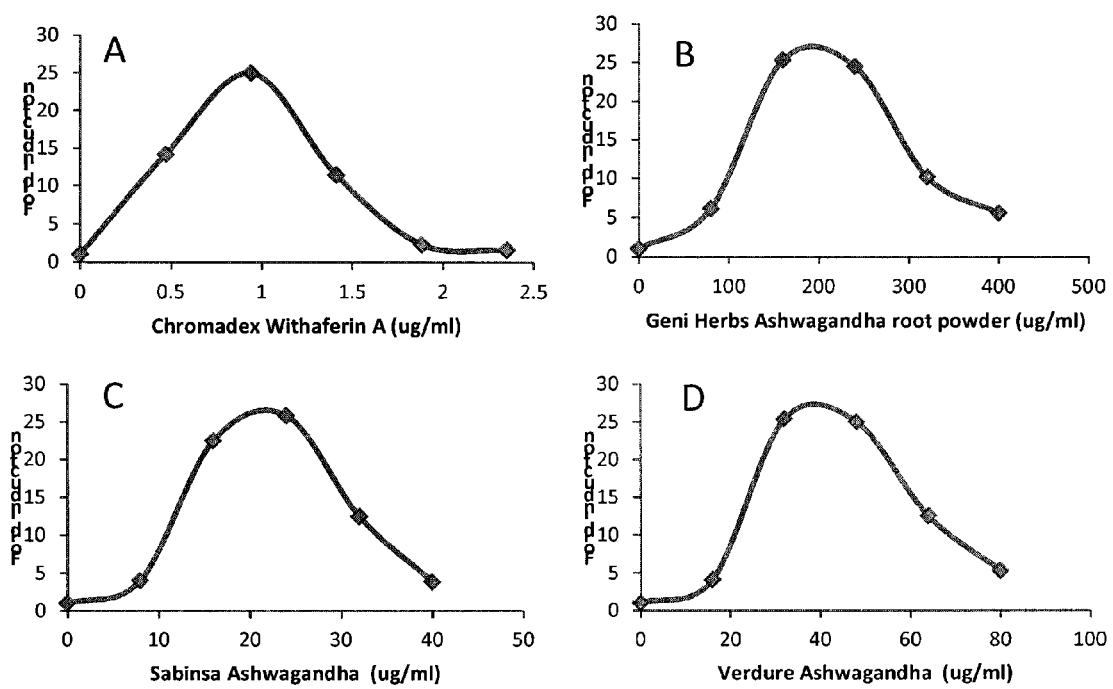
FIG. 34 shows plots of Nrf2 fold-induction (FI) vs. concentration of Nrf2 activator samples: Chromadex Withaferin A (FIG. 34A), Geni Herbs Ashwangandha root powder (FIG. 34B), Sabinsa Ashwangandha (FIG. 34C), and Verdure Ashwagandha (FIG. 34D) as measured with the AREc32 based bioassay.

The AREc32 bioassay described in Example 7 was used to identify the active ingredient in Ashwangandha extract that is capable of activating the expression of the ARE-driven reporter gene. The AREc32 cells were prepared as in Example 7. After 18-24 h the cells were reattached and growing, and ready for treatment with samples with putative Nrf2 activating activity. Test samples were added to the wells in an appropriate concentration range, in volumes ranging from 1 to 10 µl/well to about 20,000 cells/well: ethanolic extract of Chromadex withaferin A (0, 0.5 µg/ml, 1 µg/ml, 1.5 µg/ml, 2 µg/ml, and 2.5 µg/ml); ethanolic extract of Geni Herbs Ashwangandha root powder (0, 100 µg/ml, 200 µg/ml, 300 µg/ml, 400 µg/ml); ethanolic extract of Sabinsa Ashwagandha (0, 10 µg/ml, 15 µg/ml, 25 µg/ml, 30 µg/ml, and 40 µg/ml); and ethanolic extract of Verdure Ashwagandha (0, 20 µg/ml, 30 µg/ml, 40 µg/ml, 50 µg/ml, 60 µg/ml, and 80 µg/ml). Vehicles used were aqueous or organic solvents such as ethanol or DMSO, and appropriate vehicle controls were included. The cells were then returned to the incubator for 18 h. All operations up to this point were conducted under sterile conditions. After a 4 s delay following injection, luminescence was measured for 10 s. Relative Light Units (RLU) were recorded for the contents of each well. Fold Induction (FI) of luciferase activity was calculated by dividing the RLU obtained for the test well by the average RLU obtained for control wells (which received no putative Nrf2 activator). Each assay or control was performed in duplicate. Parameters noted were the concentration of test substance providing maximal fold induction of luciferase ($C_{max}$), and the maximal fold induction observed ($FI_{max}$). FIG. 34 shows plots of Nrf2 fold-induction (FI) vs. concentration of Nrf2 activator samples: alcoholic extract of Chromadex Withaferin A (FIG. 34A), alcoholic extract of Geni Herbs Ashwangandha root powder (FIG. 34B), alcoholic extract of Sabinsa Ashwagandha (FIG. 34C), and alcoholic extract of Verdure Ashwagandha (FIG. 34D) as measured with the AREc32 based bioassay.

Pure Withaferin A produced peak Nrf2 activation at a concentration of 1.0 µg/ml (or 2.1 µM), which is defined herein as $C_{max}$. The observed $C_{max}$ of root powder was 200 µg/ml indicating that the withaferin A content was 1/200, or 0.5% of the root powder. This method can be used to select extract fractions with maximal Nrf2 activating potential.

Equivalents

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A capsule, tablet or caplet for treating oxidative stress in a subject in need thereof consisting essentially of:
   (a) a *Bacopa monnieri* extract in a therapeutic amount from about 50 mg to about 3000 mg;
   (b) a *Silybum marianum* extract in a therapeutic amount from about 100 mg to about 3000 mg;
   (c) a *Withania somnifera* extract in a therapeutic amount from 10 mg to about 4000 mg;
   (d) a *Camellia sinensis* extract in a therapeutic amount from about 10 mg to about 1000 mg; and
   (e) a *Curcuma longa* extract in a therapeutic amount from about 10 mg to about 1000 mg.

* * * * *